(12) United States Patent
Ingber et al.

(10) Patent No.: US 12,187,997 B2
(45) Date of Patent: Jan. 7, 2025

(54) INTEGRATED HUMAN ORGAN-ON-CHIP MICROPHYSIOLOGICAL SYSTEMS

(71) Applicant: President and Fellows of Harvard College, Cambridge, MA (US)

(72) Inventors: Donald E. Ingber, Boston, MA (US); Anthony M. Bahinski, Wilmington, DE (US); Robert Cunningham, Cohasset, MA (US); Josue A. Goss, Somerville, MA (US); Geraldine A. Hamilton, Cambridge, MA (US); Christopher David Hinojosa, Cambridge, MA (US); Daniel Levner, Boston, MA (US); Kevin Kit Parker, Waitham, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 18/346,165

(22) Filed: Jun. 30, 2023

(65) Prior Publication Data
US 2023/0348831 A1    Nov. 2, 2023

Related U.S. Application Data

(63) Continuation of application No. 17/146,264, filed on Jan. 11, 2021, now Pat. No. 11,773,359, which is a
(Continued)

(51) Int. Cl.
*C12M 3/06*      (2006.01)
*A01N 1/02*     (2006.01)
(Continued)

(52) U.S. Cl.
CPC .............. *C12M 23/16* (2013.01); *A01N 1/02* (2013.01); *B01L 3/502715* (2013.01);
(Continued)

(58) Field of Classification Search
CPC ........ A01N 1/02; A01N 1/021; A01N 1/0247; A01N 1/0273; B01L 2200/0684;
(Continued)

(56) References Cited

U.S. PATENT DOCUMENTS

| | | |
|---|---|---|
| 3,300,386 A | 1/1967 | Aron-Brunetiere |
| 3,313,290 A | 4/1967 | Chance |

(Continued)

FOREIGN PATENT DOCUMENTS

| | | |
|---|---|---|
| DE | 2431918 | 1/1976 |
| EA | 008075 | 2/2007 |

(Continued)

OTHER PUBLICATIONS

Ball et al., "CMATRIX: Software For Physiologically Based Pharmacokinetic Modeling Using a Symbolic Matrix Representation System", Compu. Biol. Med., 24(4):269-276 (1994).
(Continued)

*Primary Examiner* — Jennifer Wecker
(74) *Attorney, Agent, or Firm* — NIXON PEABODY LLP

(57) ABSTRACT

The invention provides integrated Organ-on-Chip microphysiological systems representations of living Organs and support structures for such microphysiological systems.

12 Claims, 40 Drawing Sheets

Related U.S. Application Data continuation of application No. 16/134,746, filed on Sep. 18, 2018, now Pat. No. 10,954,482, which is a continuation of application No. 14/928,039, filed on Oct. 30, 2015, now abandoned, which is a continuation of application No. 14/362,841, filed as application No. PCT/US2012/068725 on Dec. 10, 2012, now Pat. No. 9,725,687.

(60) Provisional application No. 61/569,004, filed on Dec. 9, 2011.

(51) Int. Cl.
  B01L 3/00 (2006.01)
  B01L 9/00 (2006.01)
  C12M 1/00 (2006.01)
  C12M 1/34 (2006.01)
  C12M 1/42 (2006.01)
  C12M 3/00 (2006.01)
  G01N 33/50 (2006.01)

(52) U.S. Cl.
  CPC .............. *B01L 9/52* (2013.01); *C12M 21/08* (2013.01); *C12M 23/42* (2013.01); *C12M 29/10* (2013.01); *C12M 35/04* (2013.01); *C12M 35/08* (2013.01); *C12M 41/00* (2013.01); *G01N 33/5082* (2013.01); *G01N 33/5088* (2013.01); *A01N 1/021* (2013.01); *A01N 1/0247* (2013.01); *A01N 1/0273* (2013.01); *B01L 3/5027* (2013.01); *B01L 2200/0684* (2013.01); *B01L 2200/0689* (2013.01); *B01L 2200/146* (2013.01); *B01L 2200/147* (2013.01); *B01L 2300/044* (2013.01); *B01L 2300/0636* (2013.01); *B01L 2300/0654* (2013.01); *B01L 2300/0663* (2013.01); *B01L 2300/0867* (2013.01); *B01L 2300/0877* (2013.01); *B01L 2300/123* (2013.01); *B01L 2300/18* (2013.01); *B01L 2400/0487* (2013.01); *B01L 2400/0622* (2013.01); *B01L 2400/0644* (2013.01); *C12M 41/12* (2013.01); *C12M 41/46* (2013.01); *G01N 33/5005* (2013.01)

(58) Field of Classification Search
  CPC ....... B01L 2200/0689; B01L 2200/146; B01L 2200/147; B01L 2300/044; B01L 2300/0636; B01L 2300/0654; B01L 2300/0663; B01L 2300/0867; B01L 2300/0877; B01L 2300/123; B01L 2300/18; B01L 2400/0487; B01L 2400/0622; B01L 2400/0644; B01L 3/5027; B01L 3/502715; B01L 9/52; C12M 21/08; C12M 23/16; C12M 23/42; C12M 29/10; C12M 35/04; C12M 35/08; C12M 41/00; C12M 41/12; C12M 41/46; G01N 33/5005; G01N 33/5082; G01N 33/5088

See application file for complete search history.

(56) References Cited

U.S. PATENT DOCUMENTS

| | | |
|---|---|---|
| 3,722,504 A | 3/1973 | Sawyer |
| 3,941,662 A | 3/1976 | Munder |
| 3,948,732 A | 4/1976 | Haddad |
| 4,225,671 A | 9/1980 | Puchinger |
| 4,436,824 A | 3/1984 | Bishop |
| 4,446,229 A | 5/1984 | Indech |
| 4,537,860 A | 8/1985 | Tolbert |
| 4,610,878 A | 9/1986 | Wilson |
| 4,629,686 A | 12/1986 | Gruenberg |
| 4,650,766 A | 3/1987 | Harm |
| 4,673,650 A | 6/1987 | Braden |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer |
| 4,835,102 A | 5/1989 | Bell |
| 4,839,280 A | 6/1989 | Banes |
| 4,851,354 A | 7/1989 | Winston |
| 4,929,542 A | 5/1990 | Risley |
| 4,940,853 A | 7/1990 | Vandenburgh |
| 5,002,890 A | 3/1991 | Morrison |
| 5,043,260 A | 8/1991 | Jauregui |
| 5,108,926 A | 4/1992 | Klebe |
| 5,160,490 A | 11/1992 | Naughton |
| 5,217,899 A | 6/1993 | Shapiro |
| 5,290,684 A | 3/1994 | Kelly |
| 5,316,905 A | 5/1994 | Mori |
| 5,348,879 A | 9/1994 | Shapiro |
| 5,486,335 A | 1/1996 | Wilding |
| 5,496,697 A | 3/1996 | Parce |
| 5,498,392 A | 3/1996 | Wilding |
| 5,587,128 A | 12/1996 | Wilding |
| 5,612,188 A | 3/1997 | Shuler |
| 5,637,469 A | 6/1997 | Wilding |
| 5,726,026 A | 3/1998 | Wilding |
| 5,744,366 A | 4/1998 | Kricka |
| 5,750,329 A | 5/1998 | Quinn |
| 5,820,769 A | 10/1998 | Chou |
| 5,900,160 A | 5/1999 | Whitesides |
| 5,906,828 A | 5/1999 | Cima |
| 6,048,723 A | 4/2000 | Banes |
| 6,054,277 A | 4/2000 | Furcht |
| 6,133,030 A | 10/2000 | Bhatia |
| 6,197,575 B1 | 3/2001 | Griffith |
| 6,255,106 B1 | 7/2001 | Marx |
| 6,306,644 B1 | 10/2001 | Marx |
| 6,329,195 B1 | 12/2001 | Pfaller |
| 6,454,924 B2 | 9/2002 | Jedrzejewski |
| 6,472,202 B1 | 10/2002 | Banes |
| 6,498,010 B1 | 12/2002 | Fitzgerald |
| 6,530,370 B1 | 3/2003 | Heinonen |
| 6,562,616 B1 | 5/2003 | Toner |
| 6,586,235 B1 | 7/2003 | Banes |
| 6,630,801 B2 | 10/2003 | Schuurmans |
| 6,645,432 B1 | 11/2003 | Anderson |
| 6,645,759 B2 | 11/2003 | Banes |
| 6,653,124 B1 | 11/2003 | Freeman |
| 6,730,516 B2 | 5/2004 | Jedrzejewski |
| 6,921,253 B2 | 7/2005 | Shuler |
| 6,998,265 B2 | 2/2006 | Banes |
| 7,049,057 B2 | 5/2006 | Atala |
| 7,288,405 B2 | 10/2007 | Schuler |
| 7,314,718 B1 | 1/2008 | Dasgupta |
| 7,438,856 B2 | 10/2008 | Jedrzejewski |
| 7,745,209 B2 | 6/2010 | Martin |
| 7,763,456 B2 | 7/2010 | Li |
| 7,790,028 B1 | 9/2010 | Weinberg |
| 7,960,166 B2 | 6/2011 | Vacanti |
| 7,964,078 B2 | 6/2011 | Lee |
| 7,976,795 B2 | 7/2011 | Zhou |
| 7,977,089 B2 | 7/2011 | Wikswo |
| 7,985,336 B2 | 7/2011 | Weinberg |
| 8,030,061 B2 | 10/2011 | Schuler |
| 8,147,562 B2 | 4/2012 | Vacanti |
| 8,187,863 B2 | 5/2012 | Sim |
| 8,268,152 B2 | 9/2012 | Stelzle |
| 8,273,572 B2 | 9/2012 | Martin |
| 8,318,479 B2 | 11/2012 | Domansky |
| 8,343,740 B2 | 1/2013 | Gonda |
| 8,357,528 B2 | 1/2013 | Vacanti |
| 8,460,546 B2 | 6/2013 | Weinberg |
| 8,470,589 B2 | 6/2013 | Martin |
| 2002/0129813 A1 | 9/2002 | Litherland |
| 2002/0146817 A1 | 10/2002 | Cannon |
| 2002/0173033 A1 | 11/2002 | Hammerick |

(56) References Cited

U.S. PATENT DOCUMENTS

| | | |
|---|---|---|
| 2003/0021792 A1 | 1/2003 | Roben |
| 2003/0082795 A1 | 5/2003 | Shuler |
| 2003/0096405 A1 | 5/2003 | Takayama |
| 2003/0175824 A1 | 9/2003 | Pishko |
| 2004/0034435 A1 | 2/2004 | Atala |
| 2004/0132166 A1 | 7/2004 | Miller |
| 2004/0248318 A1 | 12/2004 | Weinberger |
| 2005/0032205 A1 | 2/2005 | Smith |
| 2005/0169962 A1 | 8/2005 | Bhatia |
| 2005/0221269 A1 | 10/2005 | Taylor |
| 2005/0266393 A1 | 12/2005 | Baxter |
| 2005/0273995 A1 | 12/2005 | Kanagasabapathi |
| 2006/0019326 A1 | 1/2006 | Vacanti |
| 2006/0099116 A1 | 5/2006 | Manger |
| 2006/0154361 A1 | 7/2006 | Wikswo |
| 2006/0263336 A1 | 11/2006 | Caplan |
| 2006/0270023 A1 | 11/2006 | Leduc |
| 2007/0015273 A1 | 1/2007 | Shuler |
| 2007/0015274 A1 | 1/2007 | Shuler |
| 2007/0015275 A1 | 1/2007 | Shuler |
| 2007/0020693 A1 | 1/2007 | Shuler |
| 2007/0026519 A1 | 2/2007 | Shuler |
| 2007/0037273 A1 | 2/2007 | Shuler |
| 2007/0037275 A1 | 2/2007 | Shuler |
| 2007/0037277 A1 | 2/2007 | Shuler |
| 2007/0048727 A1 | 3/2007 | Shuler |
| 2007/0122794 A1 | 5/2007 | Shuler |
| 2007/0122896 A1 | 5/2007 | Shuler |
| 2007/0144514 A1 | 6/2007 | Yeates |
| 2007/0172943 A1 | 7/2007 | Freedman |
| 2007/0207194 A1 | 9/2007 | Grayburn |
| 2007/0224677 A1 | 9/2007 | Neumann |
| 2007/0243627 A1 | 10/2007 | Takayama |
| 2007/0275435 A1 | 11/2007 | Kim |
| 2007/0275455 A1 | 11/2007 | Hung |
| 2007/0275882 A1 | 11/2007 | Meijer |
| 2007/0281353 A1 | 12/2007 | Vacanti |
| 2008/0032380 A1 | 2/2008 | Kleis |
| 2008/0064088 A1 | 3/2008 | Shuler |
| 2008/0166794 A1 | 7/2008 | Shuler |
| 2008/0166795 A1 | 7/2008 | Shuler |
| 2008/0200343 A1 | 8/2008 | Clemens |
| 2008/0233607 A1 | 9/2008 | Yu |
| 2008/0261288 A1 | 10/2008 | Gonda |
| 2008/0318334 A1 | 12/2008 | Robotti |
| 2009/0028755 A1 | 1/2009 | Jedrzejewski |
| 2009/0074623 A1 | 3/2009 | Park |
| 2009/0078614 A1 | 3/2009 | Varghese |
| 2009/0131858 A1 | 5/2009 | Fissell |
| 2009/0134235 A1 | 5/2009 | Ivri |
| 2009/0220932 A1 | 9/2009 | Ingber |
| 2010/0028850 A1 | 2/2010 | Brassil |
| 2010/0041128 A1 | 2/2010 | Banes |
| 2010/0043494 A1 | 2/2010 | Gascon |
| 2010/0129784 A1 | 5/2010 | Eichentopf |
| 2010/0267136 A1 | 10/2010 | Vacanti |
| 2010/0294986 A1 | 11/2010 | Sultana |
| 2010/0304355 A1 | 12/2010 | Shuler |
| 2010/0323439 A1 | 12/2010 | Takayama |
| 2011/0000482 A1 | 1/2011 | Gumaste |
| 2011/0027804 A1 | 2/2011 | Yarmush |
| 2011/0053207 A1 | 3/2011 | Hoganson |
| 2011/0071055 A1 | 3/2011 | Belgrader |
| 2011/0086382 A1* | 4/2011 | Marx .................... C12M 23/16 435/325 |
| 2011/0183312 A1 | 7/2011 | Huang |
| 2011/0229927 A1 | 9/2011 | Larsen |
| 2011/0250585 A1* | 10/2011 | Ingber .................. C12N 5/0606 977/773 |
| 2011/0269226 A1 | 11/2011 | Van Noort |
| 2011/0287469 A1 | 11/2011 | Guenther |
| 2012/0003732 A1 | 1/2012 | Hung |
| 2012/0088693 A1 | 4/2012 | Lee |
| 2012/0135446 A1 | 5/2012 | Collins |
| 2012/0135452 A1 | 5/2012 | Shuler |
| 2012/0199487 A1 | 8/2012 | Stelzle |
| 2012/0214189 A1 | 8/2012 | Shuler |
| 2012/0318726 A1 | 12/2012 | Charest |
| 2012/0322097 A1 | 12/2012 | Charest |
| 2013/0059322 A1 | 3/2013 | Hung |
| 2013/0109594 A1 | 5/2013 | Gonda |

FOREIGN PATENT DOCUMENTS

| | | |
|---|---|---|
| EA | 200601901 | 4/2007 |
| EP | 0539383 | 5/1993 |
| EP | 0637996 | 7/1997 |
| EP | 0823483 | 2/1998 |
| EP | 0637997 | 7/1998 |
| EP | 1820846 | 8/2007 |
| ES | 2287351 | 12/2007 |
| FR | 1598245 | 7/1970 |
| FR | 2786783 | 6/2000 |
| GB | 863707 | 3/1961 |
| JP | 2001521789 | 11/2001 |
| JP | 2005514971 | 5/2005 |
| JP | 2007501633 | 2/2007 |
| JP | 4152885 | 9/2008 |
| RU | 2168174 | 5/2001 |
| RU | 2301677 | 6/2007 |
| WO | 8203227 | 9/1982 |
| WO | 9102049 | 2/1991 |
| WO | 9216826 | 10/1992 |
| WO | 9311498 | 6/1993 |
| WO | 9922781 | 5/1999 |
| WO | 9947922 | 9/1999 |
| WO | 03027223 | 4/2003 |
| WO | 03037042 | 5/2003 |
| WO | 03043675 | 5/2003 |
| WO | 2003082145 | 10/2003 |
| WO | 2004101743 | 11/2004 |
| WO | 2005014175 | 2/2005 |
| WO | 2005100537 | 10/2005 |
| WO | 2005110408 | 11/2005 |
| WO | 2006047758 | 5/2006 |
| WO | 2007021343 | 2/2007 |
| WO | 2008040015 | 4/2008 |
| WO | 2008051265 | 5/2008 |
| WO | 2009089189 | 7/2009 |
| WO | 2010009307 | 1/2010 |
| WO | 2010062911 | 6/2010 |
| WO | 2010123594 | 10/2010 |
| WO | 2011014674 | 2/2011 |
| WO | 2012016711 | 2/2012 |
| WO | 2012118799 | 9/2012 |
| WO | 2012154729 | 11/2012 |
| WO | 2012154834 | 11/2012 |
| WO | 2013056019 | 4/2013 |

OTHER PUBLICATIONS

Baudoin et al., "Trends in the development of microfluidic cell biochips for in vitro hepatoxicity", Toxicology in Vitro, 21:535-544 (2007).
Buckpitt et al., "Hepatic and Pulmonary Microsomal Metabolism of Naphthalene to Glutathione Adducts: Factors Affecting the Relative Rates of Conjugate Formation", The Journal of Pharmacology and Experimental Therapeutics 231(2):291-300 (1984).
Camp et al., "Fabrication of a multiple-diameter branched network of microvascular channels with semi-circular cross-sections using xenon difluoride etching", Biomed Microdevices 10:179-186 (2008).
Chao et al., "Evaluation of a microfluidic based cell culture platform with primary human hepatocytes for the prediction of hepatic clearance in human", Biochemical Pharmacology 78:625-632 (2009).
Cheng et al. "A hydrogel-based microfluidic device for the studies of directed cell migration", Lab Chip 7:763-769 (2007).
Delraso, "In vitro methodologies for enhanced toxicity testing", Toxicology Letters 68:91-99 (1993).
D'Souza et al, "Physiological Model for Tissue Glutathione Depletion and Increased Resynthesis after Ethylene Dichloride Exposure", The Journal of Pharmacology and Experimental Therapeutics 245(2):563-568 (1988).

(56) References Cited

OTHER PUBLICATIONS

El-Ali et al., "Cells on chips", Nature 442:403-411 (2006).
Fernandes et al., "High-throughput cellular microarray platforms: applications in drug discovery, toxicology and stem cell research", Trends in Biotechnology 27(6):342-349 (2009).
Frampton et al., "Biomedical Technologies for In Vitro Screening and Controlled Delivery of Neuroactive Compounds", Central Nervous System Agents in Medicinal Chemistry 8:203-219 (2008).
Frampton et al., "Three-dimensional hydrogel cultures for modeling changes in tissue impedance around microfabricated neural probes", J. Neural Eng. 4:399-409 (2007).
Ghaemmaghami et al., "Biomimetic tissues on a chip for drug discovery", Drug Discovery Today 17(3/4):173-181 (2012).
Ghanem et al., "Characterization of a Perfusion Reactor Utilizing Mammalian Cells on Microcarrier Beads", Biotechnol. Prog., 16:471-479 (2000).
Ghanem et al., "Combining Cell Culture Analogue Reactor Designs and PBPK Models to Probe Mechanisms of Naphthalene Toxicity", Biotechnol. Prog. 16:334-345 (2000).
Haddad et al., "A methodology for solving physiologically based pharmacokinetic models without the use of simulation softwares", Toxicology Letters, 85:113-126 (1996).
Haies et al., "Morphometric Study of Rat Lung Cells. I. Numerical and Dimensional Characteristics of Parenchymal Cell Population", Am Rev Respir Dis 123:533-541 (1981).
Harris et al., "Development of a Physiologically Based In Vitro Model of the Blood-Brain Barrier", Bioengineering Conference, Apr. 20-21, 2002. Proceedings of the IEEE 28th Annual Northeast.
Harris et al., "Growth of Endothelial Cells on Microfabricated Silicon Nitride Membranes for an In Vitro Model of the Blood-brain Barrier", Biotechnology and Bioprocess Engineering 8:246-251 (2003).
Heuschkel et al., "Buried microchannels in photopolymer for delivering of solutions to neurons in a network", Sensors and Actuators B 48:356-361 (1998).
Hoang, "Physiologically based pharmacokinetic models: mathematical fundamentals and simulation implementations", Toxicology Letters 79:99-106 (1995).
Hodgson, "ADMET-turning chemicals into drugs", Nature Biotechnology 19:722-726 (2001).
Huh et al., "A Human Disease Model of Drug Toxicity-Induced Pulmonary Edema in a Lung-on-a-Chip Microdevice", Science Translational Medicine 4(159):159ra147 (2012).
Huh et al., "Reconstituting Organ-Level Lung Functions on a Chip", Science 328:1662-1668 (2010).
Huh et al., "Acoustically detectable cellular-level lung injury induced by fluid mechanical stresses in microfluidic airway systems", PNAS 104(48):18886-18891 (2007).
Hwang, "Ferredoxin reductase affects p53-dependent, 5-fluorouracil-induced apoptosis in colorectal cancer cells", Nature Medicine 7(10):1111-1117 (2001).
Ikeda et al., "Bioactivation of Tegafur to 5-Fluorouracil Is Catalyzed by Cytochrome P-450 2A6 in Human Liver Microsomes in Vitro", Clinical Cancer Research 6:4409-4415 (2000).
Jones et al., "Glowing jellyfish, luminescence and a molecule called coelenterazine", TIBTECH 17:477-481 (1999).
Kang et al., "Microfluidics for drug discovery and development: From target selection to product lifecycle management", Drug Discovery Today 13(1/2):1-13 (2008).
Khademhosseini et al., "Microscale technologies for tissue engineering and biology", PNAS 103(8):2480-2487 (2006).
Khetani et al., "Microscale culture of human liver cells for drug development", Nature Biotechnology 26(1):120-126 (2008).
Kim et al., "Human gut-on-a-chip inhabited by microbial flora that experiences intestinal peristalsis-like motions and flow", Lab Chip 12(12):2165-2174 (2012).
Kim et al., "Investigation of doxorubicin for multi-drug resistance using a fluorescent cytometric imaging system integrated onto cell culture analog devices", Optical Diagnostics and Sensing IV, Proceedings of SPIE 5325:122-127 (2004).
Kim et al., "Microfluidic biomechanical device for compressive cell stimulation and lysis", Sensors and Actuators B 128:108-116 (2007).
Knaak et al., "Development of partition coefficients, Vmax and Km values, and allometric relationships", Toxicology Letters 79:87-98 (1995).
Koebe et al., "In vitro toxicology in hepatocyte bioreactors-extracellular acidification rate (EAR) in a target cell line indicates hepato-activated transformation of substrates", Toxicology 154:31-44 (2000).
Kola, "The State of Innovation in Drug Development", Clinical Pharmacology & Therapeutics 83(2):227-230 (2008).
Komatsu et al., "Roles of Cytochromes P450 1A6, and 2C8 in 5-Fluorouracil Formation from Tegafur, an Anticancer Prodrug, in Human Liver Microsomes", Drug Metabolism and Disposition, 28(12):1457-1463 (2000).
Lee et al., "Hydrophilic electrospun polyurethane nanofiber matrices for hMSC culture in a microfluidic cell chip", J Biomed Mater Res 90A:619-628 (2009).
Lehmann et al., "Bubble-Free Reactors and Their Development for Continuous Culture with Cell Recycle". Animal Cell Biotechnology 3:221-237 (1988).
Li et al., "Single-Step Procedure for Labeling DNA Strand Breaks With Fluorescein- or BODIPY-Conjugated Deoxynucleotides: Detection of Apoptosis and Bromodeoxyuridine Incorporation", Cytometry 20:172-180 (1995).
Ma et al., "An endothelial and astrocyte co-culture model of the blood-brain barrier utilizing an ultra-thin, nanofabricated silicon nitride membrane", Lab Chip 5:74-85 (2005).
Ma et al., "Characterization of drug metabolites and cytotoxicity assay simultaneously using an integrated microfluidic device", Lab Chip 9:232-238 (2009).
Maguire et al., "Design and Application of Microfluidic Systems for In Vitro Pharmacokinetic Evaluation of Drug Candidates", Current Drug Metabolism 10:1192-1199 (2009).
Mahler et al., "Characterization of a Gastrointestinal Tract Microscale Cell Culture Analog Used to Predict Drug Toxicity", Biotechnology and Bioengineering 104(1):193-205 (2009).
Matsuda et al., "Microfabricated Surface Designs for Cell Culture and Diagnosis", ASAIO Journal 40:M594-M597 (1994).
Mcauliffe et al., "Development of a gastrointestinal tract microscale cell culture analog to predict drug transport", Mol Cell Biomech, 5(2):119-132 Abstract only (2008).
Meyvantsson et al., "Cell Culture Models in Microfluidic Systems", Annu. Rev. Anal. Chem. 1:423-449 (2008).
Moraes et al., "Organs-on-a-Chip: A Focus on Compartmentalized Microdevices", Annals of Biomedical Engineering 40(6):1211-1227 (2012).
Munos, "Lessons from 60 years of pharmaceutical innovation", Nature Reviews Drug Discovery 8:959-968 (2009).
Oh et al., "Real-Time Fluorescence Detection of Multiple Microscale Cell Culture Analog Devices In Situ", Cytometry Part A 71A:857-865 (2007).
Ong et al., "A gel-free 3D microfluidic cell culture system", Biomaterials 29:3237-3244 (2008).
Park et al., "Integration of Cell Culture and Microfabrication Technology", Biotechnol. Prog. 19:243-253 (2003).
Poulin et al., "A Priori Prediction of Tissue: Plasma Partition Coefficients of Drugs to Facilitate the Use of Physiologically-Based Pharmacokinetic Models in Drug Discovery", Journal of Pharmaceutical Sciences, 89(1):16-35 (2000).
Powers et al., "A Microfabricated Array Bioreactor for Perfused 3D Liver Culture", Biotechnol Bioeng, 78:257-269 (2002).
Powers et al., "Functional Behavior of Primary Rat Liver Cells in a Three-Dimensional Perfused Microarray Bioreactor", Tissue Engineering 8(3):499-513 (2002).
Qi et al., "Miniature inhalation therapy platform using surface acoustic wave microfluidic atomization", Lab Chip 9:2184-2193 (2009).
Riley et al., "Bioactivation of dapsone to a cytotoxic metabolite: in vitro use of a novel two compartment system which contains human tissues", Br. J. din. Pharmac. 30:417-426 (1990).

(56) References Cited

OTHER PUBLICATIONS

Rodriguez-Antona et al., "Bioactivation of dapsone to a cytotoxic metabolite: in vitro use of a novel two compartment system which contains human tissues", Archives of Biochemistry and Biophysics 376(1):109-116 (2000).
Segelken, "Impact of biotechnology will be examined Oct. 11 at Cornell symposium", Cornell Chronicle Sep. 21, 1999.
Sheridan et al., "Initial experience with a composite autologous skin substitute", Burns 27:421-424 (2001).
Shin et al.' "Endothelialized Networks with a Vascular Geometry in Microfabricated Poly(dimethyl siloxane)", Biomedical Microdevices 6(4):269-278 (2004).
Shuler et al., "A Self-Regulating Cell Culture Analog Device to Mimic Animal and Human Toxicological Responses", Biotechnology and Bioengineering 52:45-60 (1996).
Sin et al., "A Self-Priming Microfluidic Diaphragm Pump Capable of Recirculation Fabricated by Combining Soft Lithography and Traditional Machining", Biotechnol Bioeng. 85(3):359-363 (2004).
Sin et al., "Animal on a chip: A Microscale Cell Culture Analog Device for evaluating Toxicological and Pharmacological", Proceedings of SPIE 4560:98-101 (2001).
Sin et al., "The Design and Fabrication of Three-Chamber Microscale Cell Culture Analog Devices with Integrated Dissolved Oxygen Sensors", Biotechnol. Prog. 20:338-345 (2004).
Slob et al., "Structural Identifiability of PBPK Models: Practical Consequences for Modeling Strategies and Study Designs", Critical Reviews in Toxicology 27(2):261-272 (1997).
Smyth et al., "Markers of Apoptosis: Methods for Elucidating the Mechanism of Apoptotic Cell Death from the Nervous System", BioTechniques 32:648-665 (2002).
Song et al., "Computer-Controlled Microcirculatory Support System for Endothelial Cell Culture and Shearing", Anal. Chem. 77:3993-3999 (2005).
Sung et al., "A micro cell culture analogy (pCCA) with 3-D hydrogel culture of multiple cell lines to assess metabolism-dependent cytotoxicity of anti-cancer drugs", Lap Chip 9:1385-1394 (2009).
Sung et al., "Prevention of air bubble formation in a microfluidic perfusion cell culture system using a microscale bubble trap", Biomed Microdevices 11:731-738 (2009).
Sweeney et al., "A Cell Culture Analogue of Rodent Physiology: Application to Naphthalene Toxicology", Toxic. in Vitro 9(3):307-316 (1995).
Tatosian et al., "A Novel System for Evaluation of Drug Mixtures for Potential Efficacy in Treating Multidrug Resistant Cancers", Biotechnology and Bioengineering 103(1):187-198 (2009).
Viravaidya et al., "Development of a Microscale Cell Culture Analog to Probe Napthalene Toxicity", Biotechnol. Prog. 20:316-323 (2004).
Viravaidya et al., "Incorporation of 3T3-L1 Cells To Mimic Bioaccumulation in a Microscale Cell Culture Analog Device for Toxicity Studies", Biotechnol. Prog. 20:590-597 (2004).
Warnke et al., "Growth and transplantation of a custom vascularised bone graft in a man", Lancet 364:766-770 (2004).
Whitesides, "The origins and the future of microfluidics", Nature 442(27):368-373 (2006).
Williamson et al., "Phosphatidylserine Exposure and Phagocytosis of Apoptotic Cells", Methods in Cell Biology, 66:339-364 (2001).
Wronski et al., "Two-Color, Fluorescence-Based Microplate Assay for Apoptosis Detection", BioTechniques, 32:666-668 (2002).
Yamazaki et al., "Rat Cytochrome P450 1A and 3A Enzymes Involved in Bioactivation of Tegafur to 5-Fluorouracil and Autoinduced by Tegafur in Liver Microsomes", Drug Metabolism and Disposition 29(6):794-797 (2001).
Yao e al., "Targeting Pancreatic Islets with Phage Display Assisted by Laser Pressure Catapult Microdissection", American Journal of Pathology 166(2):625-636 (2005).
Yung et al., "Micromagnetic-microfluidic blood cleansing device", Lab Chip 9:1171-1177 (2009).
Zhang et al., "Towards a human-on-chip: Culturing multiple cell types on a chip with compartmentalized microenvironments", Lab Chip 9:3185-3192 (2009).

\* cited by examiner

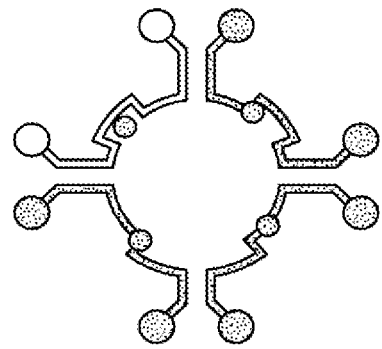
Fig. 12C
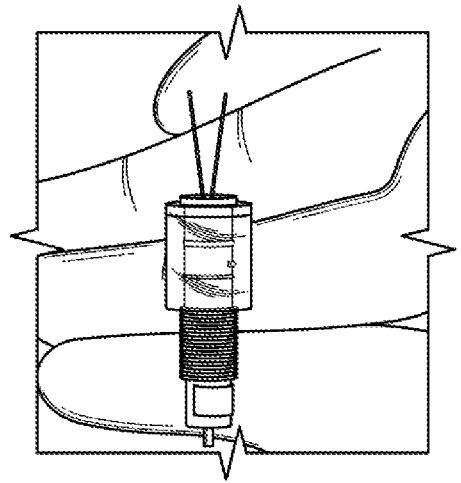
Fig. 12B
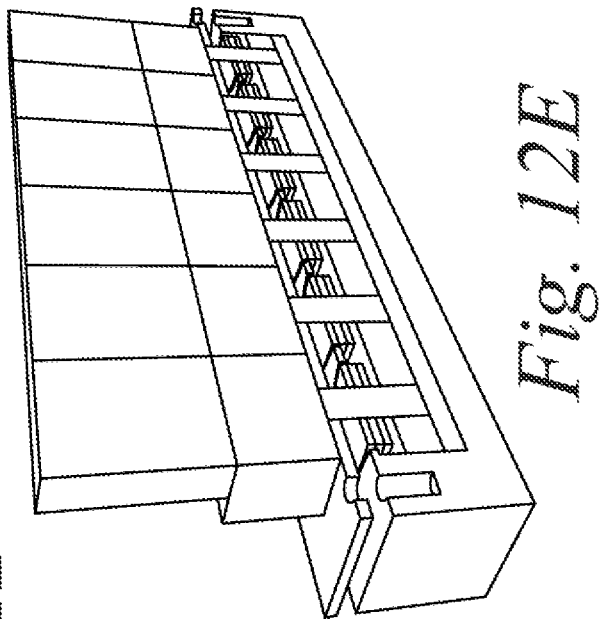
Fig. 12E
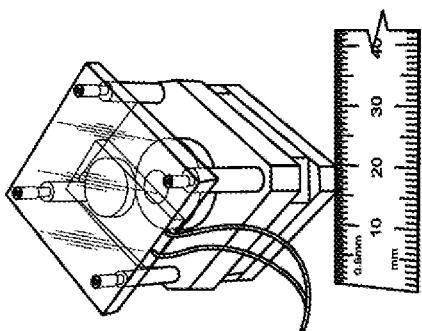
Fig. 12A
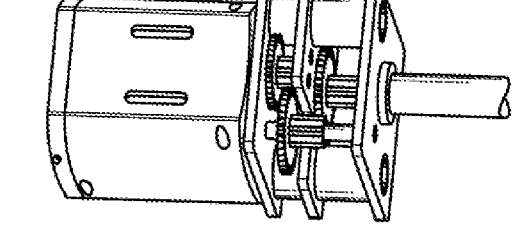
Fig. 12D
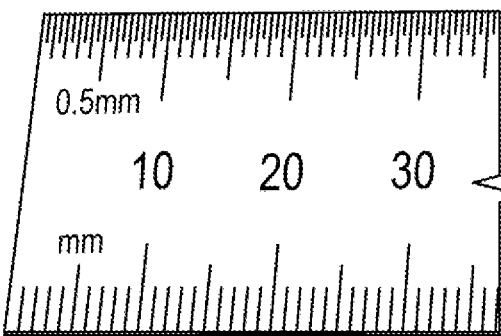

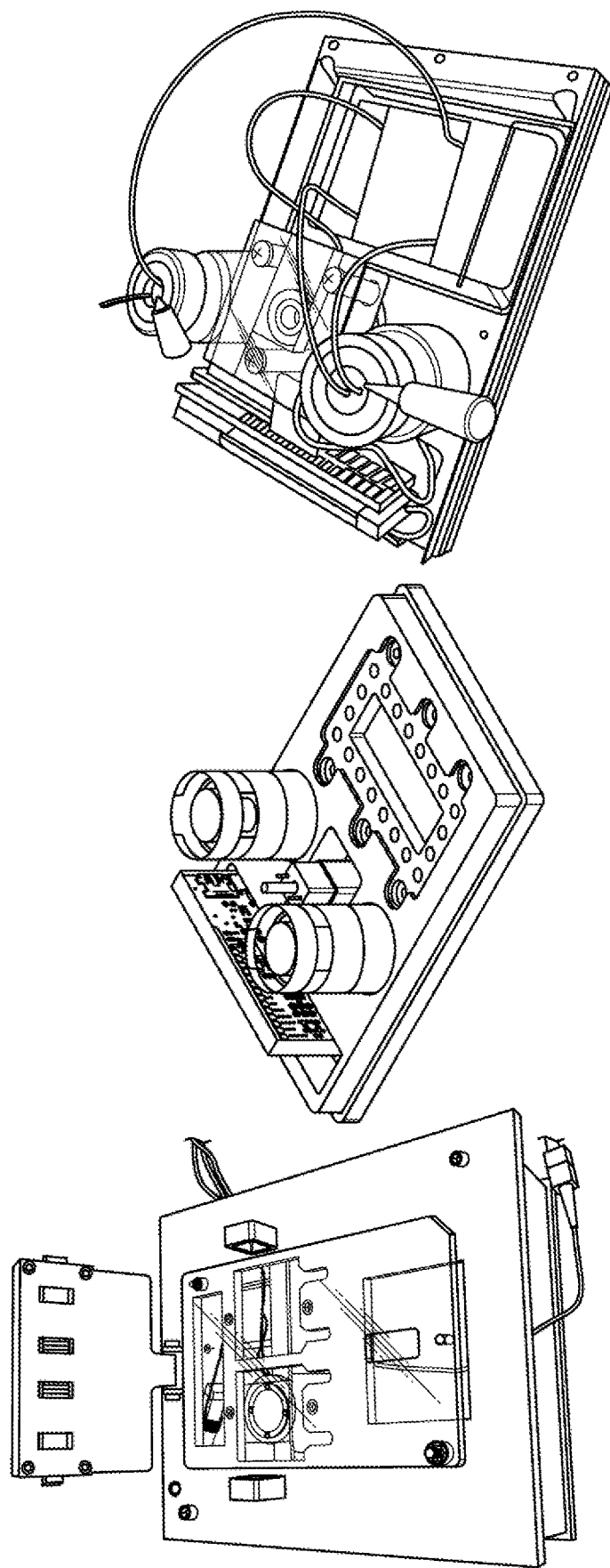

Iteration 3.0

INTEGRATED HUMAN ORGAN-ON-CHIP MICROPHYSIOLOGICAL SYSTEMS

CROSS-REFERENCE TO RELATED APPLICATIONS

This application is a continuation of U.S. Non-Provisional application Ser. No. 17/146,264, filed Jan. 11, 2021, now allowed, which is a continuation of U.S. Non-Provisional application Ser. No. 16/134,746, filed Sep. 18, 2018, now U.S. Pat. No. 10,954,482, issued Mar. 23, 2021, which is a continuation of U.S. Non Provisional application Ser. No. 14/928,039, filed Oct. 30, 2015, abandoned, which is a continuation of U.S. Non-Provisional application Ser. No. 14/362,841, filed Jun. 4, 2014, now U.S. Pat. No. 9,725,687, issued Aug. 8, 2017, which is a National Stage Entry of PCT/US2012/068725, filed Dec. 10, 2012, which claims the benefit under 35 U.S.C. § 119(e) of U.S. Provisional Application No. 61/569,004, filed Dec. 9, 2011, the contents of each of which are incorporated herein by reference in their entireties.

GOVERNMENT SUPPORT

This invention was made with government support under grant no. 5RC2DA028981-02 awarded by the National Institutes of Health, grant no. DTRA HDTRAI-09-1-0013 awarded by the Department of Defense, and grant no. W911NF-12-2-0036 awarded by the Defense Advanced Research Projects Agency (DARPA). The government has certain rights in the invention.

FIELD OF THE INVENTION

The invention relates to an integrated microphysiological system and components thereof. The invention also covers methods for the analysis of drug efficacy, toxicity, pharmacokinetics, and pharmacodynamics using the integrated microphysiological system instrumentation that consisting of multiple individual Organ Chips coupled together microfluidically.

BACKGROUND OF THE INVENTION

There is a crucial need for alternatives to animal studies for development of novel pharmaceuticals and countermeasures against biothreats for national defense, as highlighted in a recent study by the National Academy of Sciences (1). Provided herein are different human "Organ-on-a-Chip" systems containing living human cells cultured within microfluidic devices that recapitulate the three-dimensional (3D) tissue-tissue interfaces, mechanically active microenvironments, electrical stimulation, chemical conditions and complex Organ-level functions, for instance, breathing lung, beating heart, metabolic liver, flowing kidney, peristalsing gut, reactive airway, contracting skeletal muscle, skin barrier, blood-brain barrier, reproductive/endocrine testis and self-renewing bone marrow, as well as instrumentation for linking these Organ Chips microfluidically for physiological and pharmacological analysis. These integrated microphysiological systems can shorten the drug development timeline, save animal lives, reduce failure rates, inform regulatory decision-making, and accelerate development of new therapeutics in the face of emerging infectious diseases, as well as chemical or biological attack.

SUMMARY OF THE INVENTION

In one aspect provided herein is architecture of support structures for microphysiological representations of living Organs, herein referred to as Organ Chips. Organ Chips are microfluidic devices that comprise living human cells cultured within the microfluidic devices and mimic the three-dimensional tissue-tissue interfaces, mechanically active microenvironments, electrical stimulation, chemical conditions and complex Organ-level functions of living Organs, such as a breathing lung, beating heart, metabolic liver, flowing kidney, peristalsing gut, reactive airway, contracting skeletal muscle, skin barrier, blood-brain barrier, reproductive/endocrine testis and self-renewing bone marrow.

Another aspect provided herein is an Organ Cartridge that acts as an interface to at least one Organ Chip. The Cartridge comprises a base substrate which provides: (a) a holder and connections for at least one Organ Chip or one port adapted for the Organ Chip disposed thereon; and (b) at least one fluidic circuit having an inlet and an outlet, in connection with the at least one Organ Chip or the corresponding port. In some embodiments, the Organ Chip disposed on the Organ Cartridge is integrated into the Organ Cartridge, i.e., the Organ Chip is part of the Organ Cartridge itself.

In some embodiments, Organ Cartridges reside in a Cartridge Dock that can be part of an Organ Farm instrument, e.g., for further long-term culture, or an Organ Interrogator, e.g., for long-term culture and/or analysis.

In some embodiments, the Organ Cartridge comprises an on-board thermal control. Without wishing to be bound by a theory, this allows use of the Organ Cartridge as a stand-alone Organ Farm for long-term culturing of cells on an Organ Chip disposed on the Organ Cartridge.

The Organ Cartridges can be interfaced to an Organ Farm or Organ Interrogator directly or by means of a Cartridge Dock. The Cartridge Dock can mechanically support and provide fluidic connection for at least one Organ Cartridge. A Cartridge Dock can be used to interface one or more Organ Cartridges to an instrument, e.g. and Organ Farm or Organ Interrogator. In some embodiments, the Cartridge Dock provides a "plug-and-play" interface, which can allow Organ Cartridges to be attached and detached with little effort.

The Organ Cartridges can be perfused, fluidically recirculated or linked together either independently, through the use of a Cartridge Dock, which can provide additional fluidic routing of the Organ Chips present or disposed on the Organ Cartridge or provide an interface to an instrument that provides such additional fluidic routing. In some embodiments, Cartridge-docks comprises afferent, and efferent fluidic channels and controls. Cartridge-docks can also support a common medium through two or more connected Organ Chips. In some embodiments, an Organ Chip can be connected to the Cartridge Dock directly without the Organ Cartridge.

Cells can be plated, cultured, and/or maintained on an Organ Chip in an instrument or system referred to as an Organ Farm herein. An Organ Farm is a device, an instrument or a system that supports long term culturing of cells on one or more Organ Chips, i.e., the Organ Farm provides means for culturing and maintaining living cells within an Organ Chip that is present in the Organ Farm. In some embodiments, the Organ Farm can also provide for plating cells on the Organ Chip. Thus, the Organ Farm is a device, an instrument or a system that cultures (or support viability of) a one or more Organ Chips.

Generally, the Organ Farm comprises a control system for regulation of temperature, carbon dioxide, and/or moisture. In some embodiments, the Organ Farm is a device that comprises: (a) an apparatus for perfusing Organ Chips in the Organ Farm with appropriate biological media using prescribed conditions; (b) an apparatus for controlling the temperature of (and optionally gas mixture provided to) said Organ Chips; and (c) a plurality of interfaces for attaching and detaching said Organ Chips to the Organ Farm. The Organ Chip can be connected to the Organ Farm either directly, by an Organ Cartridge having the Organ Chip disposed thereon, or through a Cartridge Dock having the Organ Chip disposed thereon (either directly or via an Organ Cartridge).

In some embodiments, the Organ Farm can further comprise a means of monitoring state and progress of cells on the Organ Chips disposed therein. In some embodiments, the means for monitoring of cells is a microscope or other optical means for imaging or analyzing cell morphology.

In some embodiments, the Organ Farm can further comprise a means of actuating mechanical or electrical function in the Organ Chips disposed therein.

In some embodiments, the Organ Farm also comprises at least one valve or port that allows media sample to be withdrawn from at least one of the Organ Chips in the device.

In some embodiments, the Organ Farm can further provide one or more reservoirs to hold media and waste. This can be useful for unattended operation of the Organ Farm.

In another aspect, provided herein is an Organ-Interrogator device or system. The Organ-Interrogator can be used for assessing cell viability and function in situ on each Organ Chip, and can contain a network of valves and ports that allow media samples to be withdrawn from the system to allow off-Chip assays of cell products (e.g., using LC/MS, nESI IM-MS, UPLC-IM-MS or other conventional analytical methodologies). An Interrogator device can be used to determine biological effects (e.g., but not limited to, toxicity, and/or immune response) of active agents one or more Organs.

Generally, the Organ Interrogator is an Organ Farm having a plurality of Organ Chips, which are interconnected. In some embodiments, the Organ-Interrogator is a device that comprises: (a) a plurality of Organ Chips which are interconnected; (b) an apparatus for perfusing Organ Chips in the Organ Farm with appropriate biological media, the fluid originating at the outlet of one or more Organ Chips (including recirculation), and/or one or more challenge agents using prescribed conditions; (c) an apparatus for controlling the temperature of (and optionally gas mixture provided to) said Organ Chips; (d) a plurality of interfaces for attaching and detaching said Organ Chips to the Organ Interrogator; and (e) at least one valve or port that allows media sample to be withdrawn from at least one of the Organ Chips.

As in the Organ Farm, the Organ Chip can be connected to the Organ Interrogator either directly, by an Organ Cartridge having the Organ Chip disposed thereon, or through a Cartridge Dock having the Organ Chip disposed thereon (either directly or via an Organ Cartridge).

In some embodiments, the Organ Interrogator comprises: (a) at least one Cartridge Dock; (b) at least one fluidic circuit having an inlet and an outlet, in connection with the at least one Cartridge Dock; and (c) at least one sensor or monitor adapted for monitoring at least one environment variable when connected to an Organ Cartridge that holds an Organ Chip.

Various devices and systems described herein can be integrated into a single platform. Thus, provided herein is also integrated instrumentation for an Organ-on-Chip Microphysiological Platform system. In some embodiments, the system comprises one or more Organ Farms and one or more Organ Interrogator devices.

BRIEF DESCRIPTION OF THE FIGURES

FIG. 5A is a depiction of the heart-on-a-Chip that contains an electrophysiological (EPhys) chamber and an Muscular Thin Films (MTFs) contractility chamber fed by a single medium stream introduced through an underlying endothelium-lined microvascular channel (not shown). FIG. 5B shows that the EPhys chamber allows ECG recordings on a monolayer of muscle cells in a low fluid volume with microelectrodes embedded in the bottom of the chamber. FIG. 5C shows that a larger chamber situated next to the EPhys chamber allows high throughput contractility optical measurements using an MTF array.

FIG. 8A represents the gut in vivo, FIG. 8B illustrates the gut-on-a-Chip, in a similar Organ Chip design to the lung-on-a-Chip. FIGS. 8C and 8D depict the relaxed and elongated gut Organ Chip. FIG. 8E shows the Organ Chip implemented in PDMS.

FIGS. 12A-12E show Rotary Planar Peristaltic Micropump (RPPM) and Rotary Planar Valve (RPV) technology as described in PCT WO 2012/048261 A2, content of which is incorporated herein by reference in its entirety. FIG. 12A shows a stand-alone peristaltic pump whose stepping motor and microcontroller cost $190, and a pump Cartridge costing $10. FIG. 12B shows a miniature gearhead stepping motor ($200) connected to a miniature RPPM. FIG. 12C is a schematic representation of the channel layout for a RPV that can select one of four channels by a 15° rotation. FIG. 12D shows a $17 DC gearhead motor.

FIG. 12E is a schematic of an array of six RPPMs or RPVs that can be mounted on or adjacent to a single Organ Cartridge for the purpose of controlling fluid flows as required in support of the Organ.

FIG. 13A shows three pumps with different sized stepping motors. FIG. 13B shows a microcontroller module capable of controlling four stepping motors. FIG. 13C shows the graphical user interface for controlling four pumps. FIG. 13D shows a system capable of calibrating four pumps simultaneously. FIG. 13E shows a pump calibrator that can not only determine the follow rate as a function of motor speed, but also the flow rate of the pump as a function of backpressure applied to the pump.

FIG. 15A is a schematic representation of the system, with two syringe pumps to provide continuous perfusion of the Organ, two pumps for drugs, a pump for cell loading as required for the Perfusion Controller, and three pumps for calibration solutions for the MicroClinical Analyzer. Various computer-controlled valves implement the various functions of the Organ Cartridge. FIG. 15B shows an embodiment of the Organ Cartridge using LABSMITH® commercially available pumps, valves, and microfluidic components mounted on a custom Organ Cartridge breadboard. FIG. 15C shows the Organ Cartridge folded to fit onto the stage of a conventional inverted fluorescence microscope. FIG. 15D shows a closeup of the Organ Cartridge containing a Lymph-Node Organ Chip. FIG. 15E shows a closeup of the microfabricated traps that comprise the Lymph-Node Organ Chip. FIG. 15E shows a closeup of Jurkat cells in the Lymph-Node Organ Chip being visualized in the setup shown in FIGS. 15D and 15E.

FIGS. 16A-16E depict additional embodiments of Organ Cartridges, showing smaller Organ Cartridge designs with disposable Organ Chip microfluidics. FIG. 16A shows an embodiment of the Organ Cartridge that has the microfluidic channels in a standard well-plate footprint and the capability of having fluids pumped by a rotary peristaltic pump that is located beneath the disposable microfluidic system. FIGS. 16B and 16C are schematic representations of an embodiment of a simple Organ Cartridge where the pump and reservoirs required for Organ Chip perfusion are self-contained in a well-plate format device that includes a microcontroller, battery, and wireless connection to control the pump during long-term perfusion. FIGS. 16D and 16E are schematic representations of an embodiment of a Organ Cartridge that has three motors driving one rotary planar peristaltic micropump and two rotary planar valves as required for the Perfusion Controller that maintains the Organ Chip, which has totally self-contained and disposable microfluidics.

FIG. 24A is an photograph showing one embodiment of Cartridge Dock comprising at least two Cartridge bays with one Organ Cartridge engaged in the bay.

FIG. 24B is a set of photographs showing different embodiments of a Cartridge Dock.

FIG. 28A is a photograph of one embodiment of an Organ Farm described herein. FIG. 28B is a photograph of one embodiment of a module of an Organ Farm described herein.

DETAILED DESCRIPTION

There is a crucial need for alternatives to animal studies for development of novel pharmaceuticals and countermeasures against biothreats for national defense, as highlighted in a recent study by the National Academy of Sciences (1). Accordingly, provided herein are different human "Organ-on-a-Chip" systems containing living mammalian (e.g., human) cells cultured within microfluidic devices that recapitulate the three-dimensional (3D) tissue-tissue interfaces, mechanically active microenvironments, electrical stimulation, chemical conditions and complex Organ-level functions, for instance, breathing lung, beating heart, metabolic liver, flowing kidney, peristalsing gut, reactive airway, contracting skeletal muscle, skin barrier, blood-brain barrier, reproductive/endocrine testis and self-renewing bone marrow. These integrated microphysiological systems can shorten the drug development timeline, save animal lives, reduce failure rates, inform regulatory decision-making, and accelerate development of new therapeutics in the face of emerging infectious diseases, as well as chemical or biological attack.

One advantage of the systems described herein is that they provide in-vivo like Organ functionalities by reconstituting natural 3D interfaces between parenchmycal and vascular tissues, providing microfluidic flows (e.g., liquid medium and air), and mimicking the Organ's dynamic mechanical microenvironment.

Organ Chip

As used herein, the term "Organ Chip" refers to a microfluidic device which at least one physiological function of at least one mammalian (e.g., human) Organ. While the Organ Chips are discussed herein as mimicking a physiological function of a mammalian organ, it is to be understood that Organ Chips can be designed that can mimic the functionality of any living organ from humans or other organisms (e.g., animals, insects, plants). Thus, as used herein, the term Organ Chip in not limited to just those that mimic a mammalian organ, but includes Organ Chips which can mimic the functionality of any living organ from any organism including mammals, non-mammals, insects, and plants. AS such, the systems, devices, and instruments described herein can be used to model or study mammalian as well as non-mammalian (e.g., insects, plants, etc.) organs and physiological systems and effect of active agents on such organs and physiological systems.

In some embodiments, an Organ Chip can be a microfluidic device which can mimic at least one physiological function of one mammalian (e.g., human) Organ. In some embodiments, an Organ Chip can be a microfluidic device which can mimic physiological function of at least one (including 1, 2, 3, 4, 5, 6, 7 or more) mammalian (e.g., human) Organs. In some embodiments where the Organ Chips mimic physiological functions of more than one mammalian (e.g., human) Organs, the Organ Chips can comprise individual sub-units, each of which can mimic physiological function of one specific mammalian (e.g., human) Organ.

Figure 1:
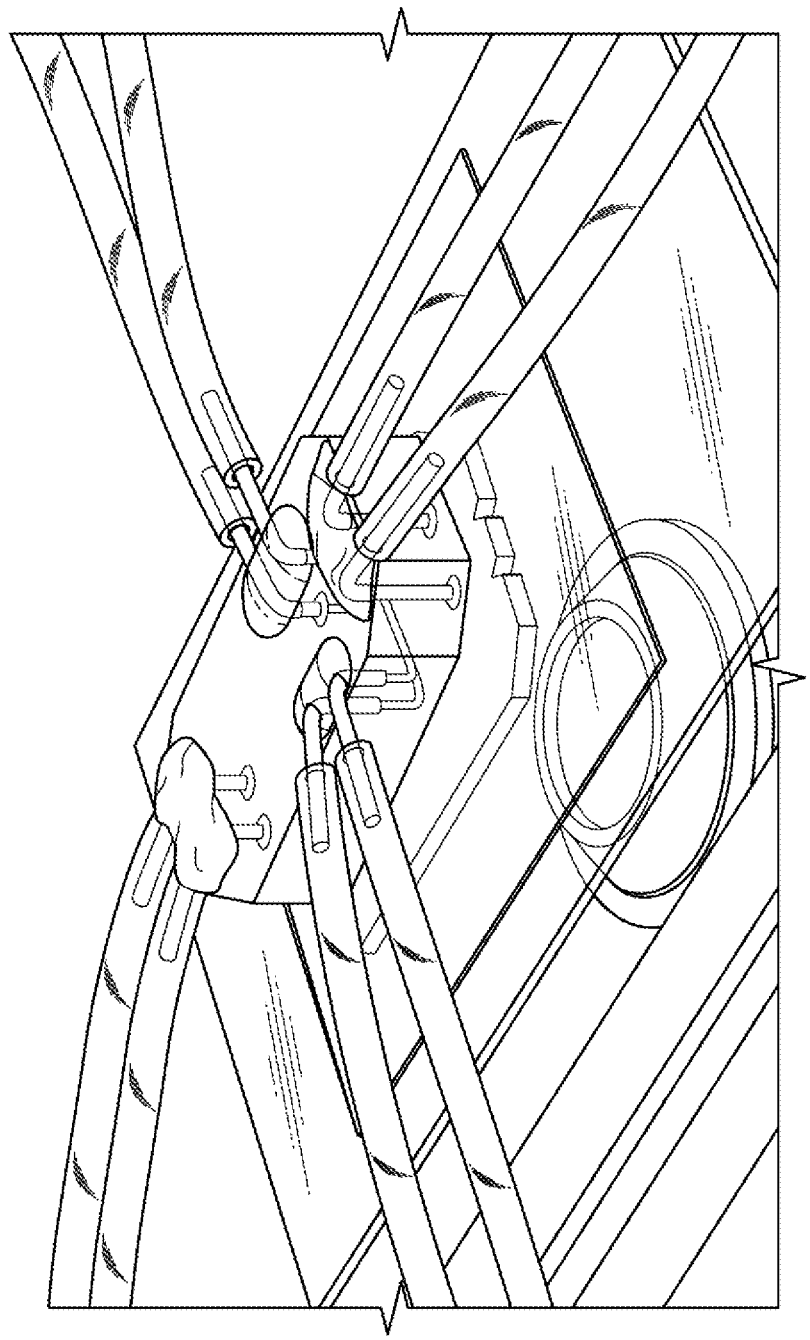
FIG. 1 is a photograph of a typical Organ Chip.
Figure 2:
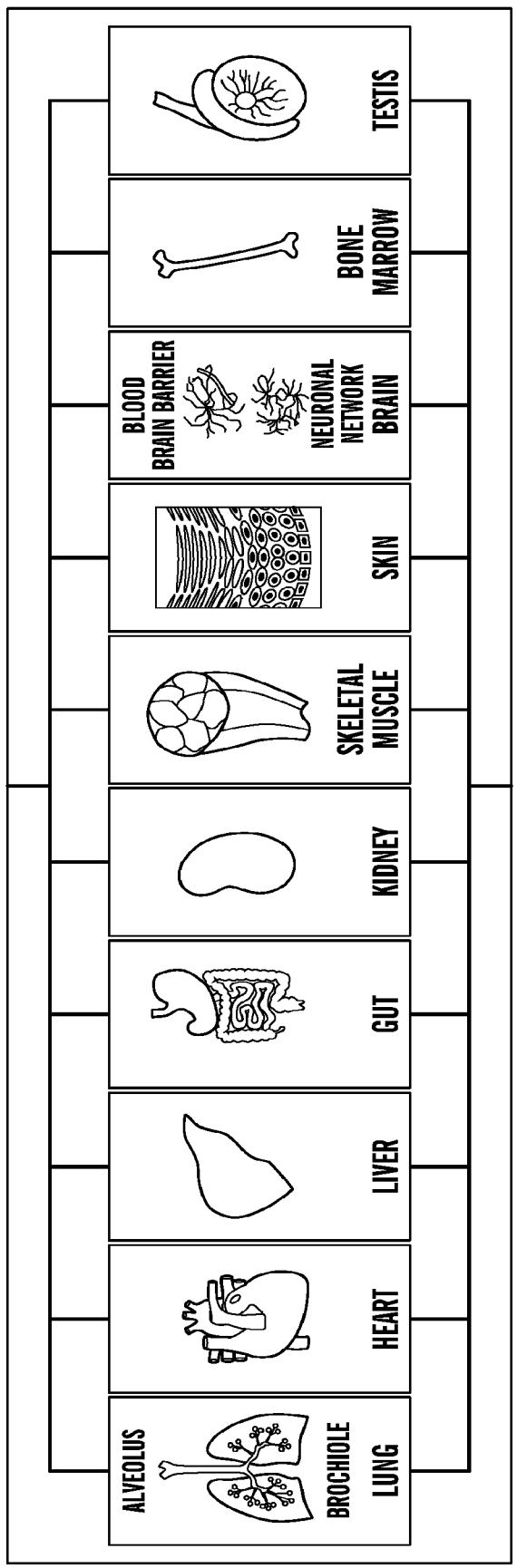
FIG. 2 is a schematic representation of a human-on-a-Chip concept according to an embodiment of the invention.

Organ Chips are also referred to as Organ Mimic Devices in the art. Generally, the Organ Chips comprise a substrate and at least one (e.g., one, two, three, four, six, seven, eight, nine, ten, or more) microfluidic channels disposed therein. The number and dimension of channels in an Organ Chip can vary depending on the design, dimension and/or function of the Organ Chip. In some embodiments, an Organ Chip can comprise at least one (e.g., one, two, three, four, six, seven, eight, nine, ten, or more) microfluidic channels for the purpose of replenishing nutrients to the biological material contained within the Organ Chip. An at least partially porous and at least partially flexible membrane is positioned along a plan within at least one of the channels, wherein the membrane is configured to separate said channel to form two sub-channels, wherein one side of the membrane can be seeded with vascular endothelial cells, and the other side of the membrane can be seeded with at least one type of Organ-specific parenchymal cells. An exemplary Organ Chip is shown in FIG. 1, and multiple Organ Chips can be used to represent a human-on-a-Chip (FIG. 2) or a portion thereof.

Without limitations, Organ Chips can comprise additional cell types, e.g., immune, stromal, neurons, lymphatic, adipose, and microbiome in gut, based on the goal of the application as described in the U. S. Provisional No.: U.S. 61,470,987, the content of which is incorporated here by reference in its entirety. By way of example only, if inflammatory response is desired to be studied in a gut or liver model, immune cells can be incorporated into the gut or liver Chip accordingly.

In some embodiments, an Organ Chip can comprise a plurality of channels (e.g., at least two, at least three, at least four, at least five, at least six, at least seven, at least eight, at least nine, at least ten or more channels). One of skill in the art will readily be able to design and determine optimum number and/or dimension of channels required to achieve a certain application. For example, if assessment of reproducibility and/or comparison of at least two experimental conditions are desirable, an Organ Chip can be constructed to comprise at least two, at least three, at least four, at least five identical channels. This can provide for a number of read-outs per Chip, e.g., allowing assessment of reproducibility and/or for validation and implementation of the technology. For example, each channel can run a different condition (e.g., culturing normal (healthy) cells vs. diseased cells in different channels, or applying different dosages of the same drug to different channels, or applying different drugs at the same dosage to different channels). In some embodiments, an Organ Chip can comprise at least two parallel (e.g., 2, 3, 4, 5, 6, 7, 8, 9, 10, or more) channels. In one embodiment, an Organ Chip comprises four parallel channels, e.g., four identical parallel channels. Without wishing to be bound by theory, this configuration can provide quadruplicate readouts per Chip.

The dimensions of the channels in the Organ Chips can each independently vary, e.g., depending on the channel function (e.g., as a conduit for fluid transfer or as a chamber for cell culture, e.g., for subsequent monitoring of cellular response), flow conditions, tissue microenvironment to be simulated, and/or methods for detecting cellular response. Thus, the cross-sectional dimensions of the channels can vary from about 10 μm to about 1 cm or from about 100 μm to about 0.5 cm.

In some embodiments, the Organ Chips disposed on the Organ Cartridge can perform the same and/or a different Organ-level function. Examples of Organ-level functions include, but are not limited to, functions of lung, gut, kidney, liver, skin, skeletal muscle, brain, bone marrow, spleen, and reproductive system (e.g., testis).

As an Organ Chip is designed to mimic the respective function of an Organ, the design of each Organ Chip can be different according to its respective physiological properties and functions. For example, the Organ Chips can differ in cell populations (e.g., cell types and/or initial cell seeding density), internal design, microarchitecture, dimensions, fluidic control, mechanical and electrical control and read-outs depending on the Organ type (e.g., Lung Chip versus Heart Chip).

Figure 3B:
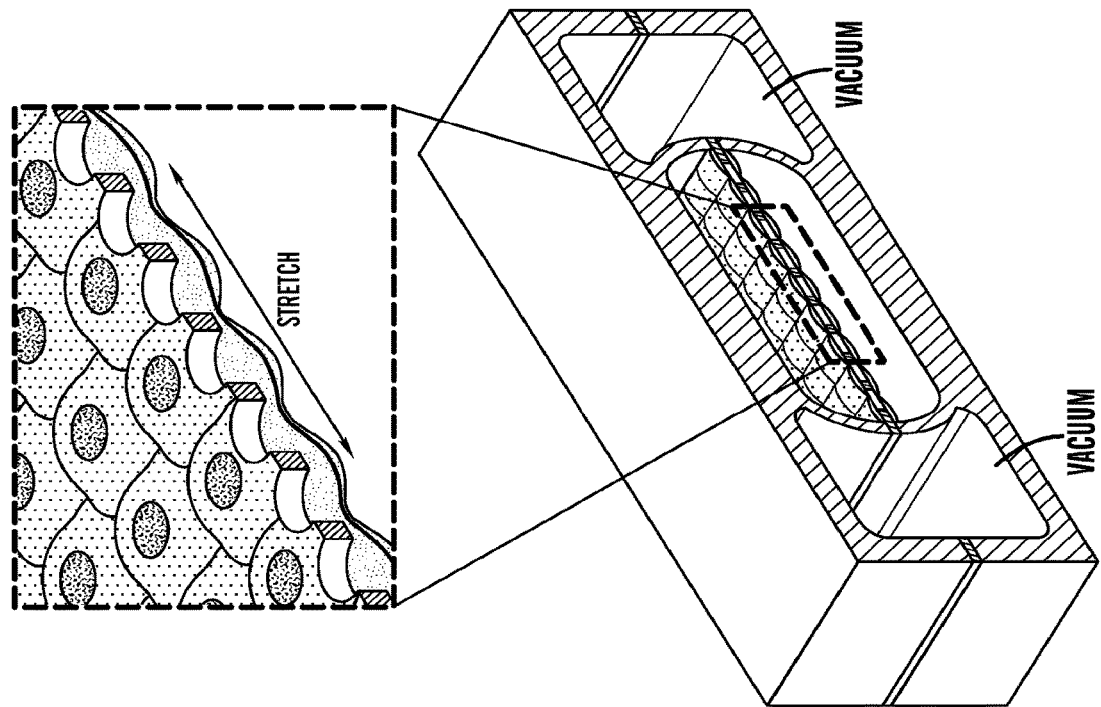
FIG. 3B is a schematic representation of an embodiment of the lung-on-a-Chip while the Organ is inspiring.
Figure 3A:
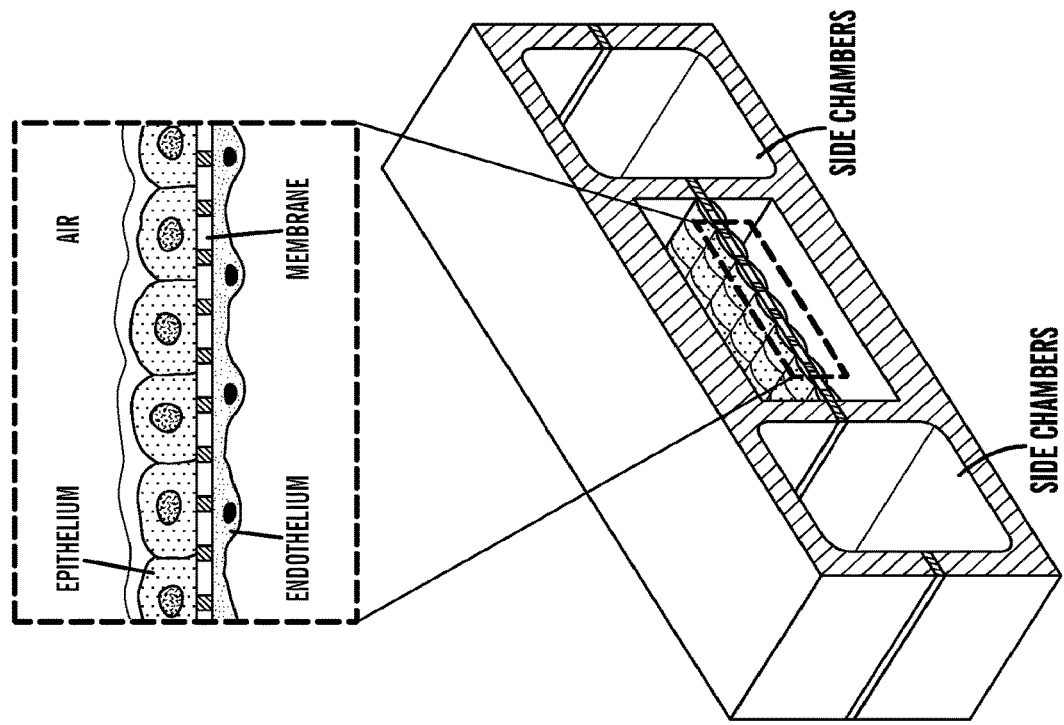
FIG. 3A is a schematic representation of an embodiment of the lung-on-a-Chip.

FIGS. 3A-3B shows diagrammatic views of a lung-on-a-Chip in accordance with one embodiment described herein. The lung Chip can comprise a body 302 having a central microchannel 304 therein; and an at least partially porous and at least partially flexible membrane 306 positioned within the central microchannel 304 and along a plane. The membrane 306 is configured to separate the central microchannel 304 to form a first central microchannel 308 and a second central microchannel 310, wherein a first fluid is applied through the first central microchannel 308 and a second fluid is applied through the second central microchannel 310. There is at least one operating channel (312A, 312B) separated from the first 308 and second 310 central microchannels by a first microchannel wall 314. The membrane 306 is mounted to the first microchannel wall 314, and when a pressure is applied to the operating channel (312A and/or 312B), it can cause the membrane to expand or contract along the plane within the first 308 and the second 310 central microchannels.

In some embodiments, one side of the membrane 306 can be seeded with alveolar epithelial cells to mimic an epithelial layer while another side of the membrane 306 can be seeded with lung microvascular endothelial cells to mimic capillary vessels. Accordingly, lung Chips, in some embodiments can be used to mimic an alveolar-capillary unit, which plays a vital role in the maintenance of normal physiological function of the lung as well as in the pathogenesis and progression of various pulmonary diseases.

In such embodiments, a gaseous fluid, e.g., air and/or aerosol, can flow through the first central microchannel 308 in which the alveolar epithelial cells are resided, while a liquid fluid, e.g., culture medium, buffered solution and/or blood, can flow through the second central microchannel 310 (Microvascular channel) in which the microvascular endothelial cells are resided.

Exemplary Organ Chips amenable to the present disclosure are described, for example, in U.S. Provisional Application No. 61/470,987, filed Apr. 1, 2011; No. 61/492,609, filed Jun. 2, 2011; No. 61/447,540, filed Feb. 28, 2011; Ser. No. 6/449,925, filed Mar. 7, 2011; and No. 61/569,029, filed on Dec. 9, 2011, in U.S. patent application Ser. No. 13/054,095, filed Jul. 16, 2008, and in International Application No. PCT/US2009/050830, filed Jul. 16, 2009 and PCT/US2010/021195, filed Jan. 15, 2010, content of all of which is incorporated herein by reference in their entirety. Muscle Organ Chips are described, for example, in U.S. Provisional Patent Application Ser. No. 61/569,028, filed on Dec. 9, 2011, U.S. Provisional Patent Application Ser. No. 61/697,121, filed on Sep. 5, 2012, and PCT patent application titled "Muscle Chips and Methods of Use Thereof," filed on Dec. 10, 2012 and which claims priority to the U.S. provisional application No. 61/569,028, filed on Dec. 9, 2011, U.S. Provisional Patent Application Ser. No. 61/697,121, the entire contents of all of which are incorporated herein by reference.

Without limitations, the Organ Chips can have any desired shape. In some embodiments, the Organ Chips can be designed to have a common shape and have positioned inlets and outlets for delivery of fluids to the Microvascular and Interstitial fluid channels lined by human endothelium and Organ-specific parenchymal cells (e.g., alveolar epithelium, heart muscle, hepatocytes, airway smooth muscle cells, astrocytes, fibroblasts), respectively.

One of skill in the art can design and determine optimum number and dimension of channels required to achieve a certain application. For example, an Organ Chip can be constructed to comprise at least two (e.g., two, four, six, eight, ten or more) identical channels. This configuration can provide multiple read-outs per Chip, which allows assessment of reproducibility for validation of this new technology. This can be useful for the culture of biological material and/or assessing reproducibility. In some embodiments, an Organ Chip can comprise four identical channels, which can provide quadruplicate readout per Chips. The channels can be configured in a parallel, i.e., substantially parallel configuration.

In some embodiments, outflow of a channel on an Organ Chip can be routed into another. Without wishing to be bound by a theory, this allows mimicking the interconnection of various Organs. For example, outflow of one Organ Chip's Interstitial Channel can be routed into another. This allows mimicking the interconnection of various Organs. For example, outflow from a Blood-Brain Barrier Chip can be provide the inflow for a Brain Neurons Chip.

In some embodiments, outflow of one Organ Chip's Microvascular Channel can be routed into a Microvascular Channel of another Organ Chip. This allows mimicking the vascular interconnection of various Organs. For example, outflow from the Microvascular Channel of a lung Chip in which aerosolized drug has been introduced into the air space of the Interstitial Channel can provide the inflow for a Heart Chip to determine cardiotoxicity of the drug after absorption across the alveolar-capillary interface in vitro.

In some embodiments, outflow of one Organ Chip's Interstitial Channel can be routed into the Microvascular Channel of another Organ Chip or vice versa.

Accordingly, an integrated network can be developed, in accordance with various applications, by using different combinations of Organ Chips and/or Organ Cartridges having one or more Organ Chips disposed thereon. In some embodiments, the Organ Chip can comprise an integrated network of different Organ mimics representatives of the circulatory (heart muscle, vascular endothelium, bone marrow), endocrine (testis), gastrointestinal (liver, gut), immune (bone marrow), integumentary (skin), musculoskeletal (skeletal muscle), nervous (BBB with astrocytes, neuronal networks), reproductive (testis), respiratory (lung alveolus, airway smooth muscle) and/or urinary (kidney) microphysiological systems. Multiple subsets of these could also be studied independently, e.g. multiple sets of heart, lung, and liver.

In some embodiments, the Organ Chip comprises a fluid control element. Without limitations, any fluid control elements can be incorporated into the Organ Chips described herein to modulate the fluid flow. For instance, a pump or a valve microchannel to control microcirculation within the Organ Chip, between Organ Chips, or for sample extraction for analysis.

Cells on the Organ Chips can be oxygenated using On-Organ-Chip, on-Organ-Cartridge, on-Cartridge Dock, on-instrument (e.g. on-Organ Farm or On-Organ Interrogator), or systemic gas exchange membranes, either through a porous material used in the construction of any of the preceding (e.g., PDMS) or using gas exchange membranes. Excess carbon dioxide can be removed similarly.

In some embodiments, the Organ Chip comprises a means for monitoring an environmental variable and/or response of cells to the surrounding conditions. For example, the Organ Chip can comprise one or more sensors for monitoring the response of cells to the surrounding conditions.

The Organ Chips can also have control ports for application of mechanical deformation (e.g., side chambers to apply cyclic vacuum, as in the Lung Chip described in the PCT Application No.: PCT/US2009/050830) and electrical connections (e.g., for electrophysiological analysis of muscle and nerve conduction).

A similar approach of producing the Lung Chips with or without aerosol delivery capabilities as described, e.g., in the PCT Application No.: PCT/US2009/050830 and U.S. Provisional Application Nos.: 61,483,837 and 61,541,876, the contents of which are incorporated herein by reference in their entirety, can be extended to produce other Organ Chips, e.g., heart Chips and liver Chips.

In some embodiments, Organ Chips can be fabricated from any biocompatible materials. Examples of biocompatible materials include, but are not limited to, glass, silicon, silicones, polyurethanes, rubber, molded plastic, polymethylmethacrylate (PMMA), polycarbonate, polytetrafluoroethylene (TEFLON™), polyvinylchloride (PVC), polydimethylsiloxane (PDMS), and polysulfone. In one embodiment, Organ Chips can be fabricated from PDMS (poly-dimethylsiloxane).

Without limitations, Organ Chips can be disposable, either in their entirety or as subcomponents.

In some embodiments, the Organ Chip can comprise one or more integrated pumps, valves (e.g. rotary or pneumatic), bubble traps, oxygenators, gas-exchangers (e.g., to remove carbon dioxide), and in-line microanalytical functions. Without limitations, using such Organ Chips can provide enhanced perfusion control and permits much finer fluidic control and real-time metabolic sensing functions (e.g., $O_2$, pH, glucose, lactate), as well as feedback control capabilities as required to adjust the physical and chemical conditions of the Organ Chip.

In some embodiments, the Organ Chip can comprise one or more bubble traps to minimize the effects of any bubbles that may form in the pumps, valves, sensors, connectors, or tubing. These bubble traps can either be self-venting, manually vented, or vented under computer control. In some embodiments, the bubble trap can be a membrane based bubble trap as described in U.S. Provisional Application No. 61/696,997, filed Sep. 5, 2012, and U.S. Provisional Application No. 61/735,215 titled "Cartridge Manifold and Membrane Based-Microfluidic Bubble Trap," filed on filed on Dec. 10, 2012, the contents of both of which are incorporated herein by reference in their entireties.

As described in U.S. Provisional Application No. 61/696, 997, filed Sep. 5, 2012, the bubble trap works by replacing a part of a surface (e.g., the top surface) of a fluid channel with a gas permeable membrane. While the gas permeable membrane can be made of any material, the gas permeable membrane is generally liquid impermeable. The membrane allows gas permeation without letting fluid through. In some embodiments the gas permeable membrane can be hydrophobic. In some embodiments, the gas permeable membrane is a PTFE membrane.

When an air bubble in the fluid channel comes into contact with the gas permeable membrane, the liquid in the channel wets the membrane surface, which is in contact with the flow channel, and fluid pressure forces the air bubble through the membrane to the other side of the membrane, which can be an air channel. The trap requires sufficient fluid pressure to push the bubble through the membrane. In some embodiments, this pressure can be generated upstream of the fluid channel. For example, the pressure generated upstream of a microfluidic channel comprising a bubble trap in an Organ Chip, Organ Cartridge, Cartridge Dock, Organ Farm, or Organ Interrogator during cell culture perfusion can be sufficient to force a bubble through the membrane.

Figure 29:
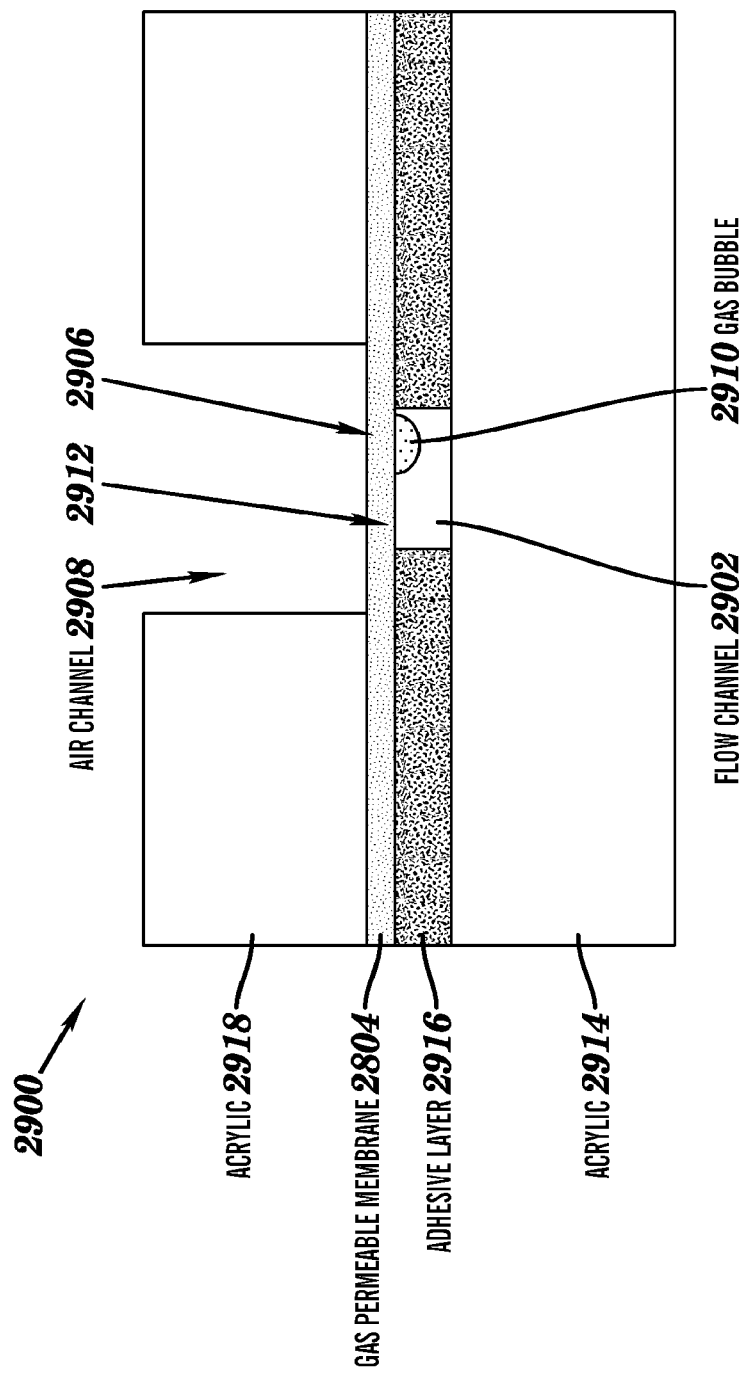
FIG. 29 is a schematic representation of a cross-sectional view of a bubble trap according to an embodiment described herein.

An exemplary embodiment of the bubble trap is shown in FIG. 29. As shown in FIG. 29, in one embodiment, the bubble trap (2900) comprises a flow channel (2902) wherein a part of a surface (e.g., the top surface) of the fluid channel (2902) is a gas permeable membrane (2904). The opposing side/surface (2906) of the gas permeable membrane can be in contact with a second channel (2908) which can be open to air. While the exemplary bubble trap is shown with an air channel (2908), it is to be understood that the air channel (2908) may or may not be necessary as long as the opposing side/surface (2906) of the membrane (2904) is in contact with air or some other gaseous material. When an air bubble (2910) in the fluid channel (2902) comes into contact with the gas permeable membrane (2904), the liquid in the channel wets the membrane surface (2912), which is in contact with the flow channel (2902), and fluid pressure forces the air bubble (2910) through the membrane (2904) to the opposing side/surface (2906) of the membrane (2904), which can be an air channel (2908).

In some embodiments, the bubble trap can be made by layering a base material (2914) (e.g. acrylic), with two-sided adhesive tape (2916), and a gas permeable membrane (2904) (e.g., PTFE). The fluidic channel (2902) is cut into the adhesive layer (2916) with a laser cutter, which is can then be used to attach the gas permeable membrane ((2904) and top (2918) and bottom (29014) layers of the base material (e.g. acrylic).

Exemplary Organ Chips

The presence of the endothelium and its basement membrane lining the Microvascular Channel on the opposite side of the membrane, plus the ability to perfuse different media compositions through the Interstitial versus Microvascular Channels, is crucial for correct microphysiological representation of different Organ Chips.

Parenchymal cells are generally the distinct cells of an Organ contained in and supported by the connective tissue framework. The parenchymal cells typically perform a differentiated function that is unique to the particular Organ. In some embodiments, the term "parenchymal" can exclude cells that are common to many Organs and tissues such as fibroblasts and endothelial cells within blood vessels.

The design of other Organ Chips can be developed based on the basic designs of the Lung or Heart Chips as described herein. For example, without being limited, Gut Chips, Kidney Chips, Liver Chips, Skin Chips and Testis Chips can be developed based on the basic design of the Lung Chips, while Skeletal Muscle Chips and Airways Smooth Muscle Chips can be developed based on the design of the Heart Chips. Depending on different Organs, each Organ Chip can then be incorporated with respective tissue-specific human parenchymal cell layers within the Interstitial Channel (as described earlier) exposed to their physiological microenvironment (e.g., alveolar epithelium and skin epidermis exposed to air, gut epithelium facing a fluid-filled lumen, etc.) on one surface of the ECM-coated porous membrane, with human vascular endothelium on the opposite side lining the Microvascular Channel. The vascular endothelium cells do not have to be Organ-specific. Organ-specific differences in the mechanical microenvironment can also be mimicked by altering control parameters, such as flow rates, fluid shear stresses, cyclic mechanical strain, ECM composition, and compartment dimensions.

Lung Organ Chips

In the parenchyma of lung, the parenchymal cells can include the epithelial cells, mucus cells, goblet cells, and alveolar cells. The methods, multichanneled architecture and ability of the human Lung Chip (FIGS. 3 & 4) to mimic, at least in part, the normal physiology (e.g., normal breathing), immune responses to infection, and inflammatory response to nanoparticulate toxins have been previously described in the art (2), and in the PCT Application No.: PCT/US2009/050830 and U.S. Provisional Application Nos.: 61,483,837 and 61,541, 876, the contents of which are incorporated herein by reference in their entirety.

Figure 4:
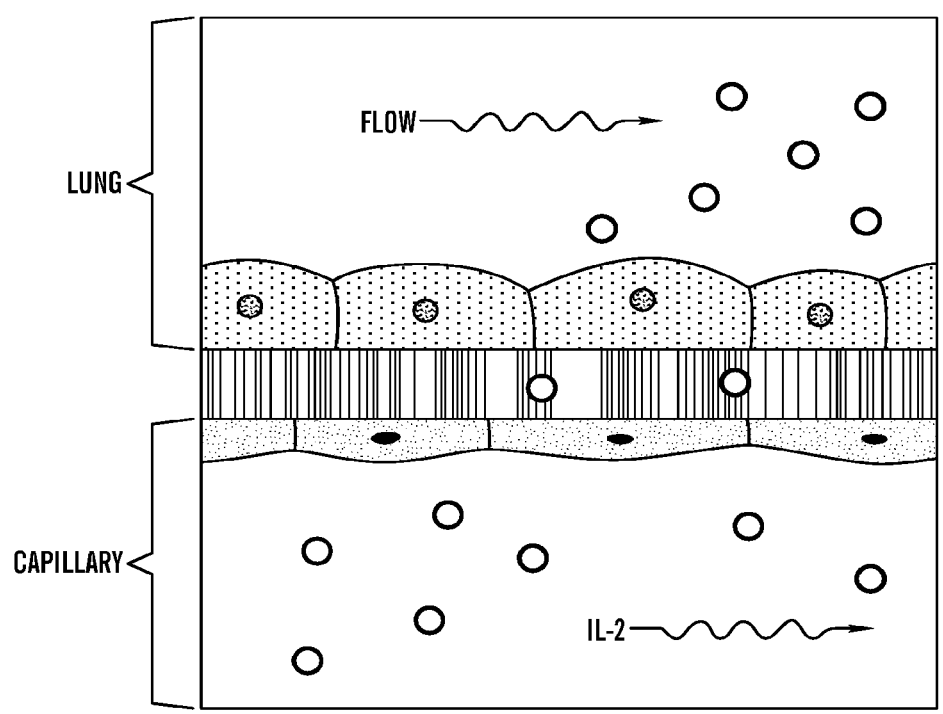
FIG. 4 shows that a human lung-on-a-Chip can predict IL-2 chemotherapy toxicity (vascular leakage) responses based on mimicry of the lung's dynamic mechanically active (breathing) microenvironment.
Figure 4:
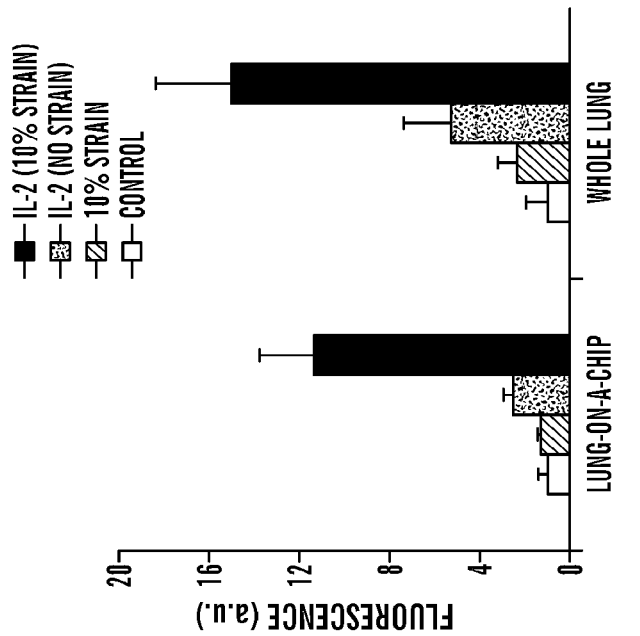
Figure 4:
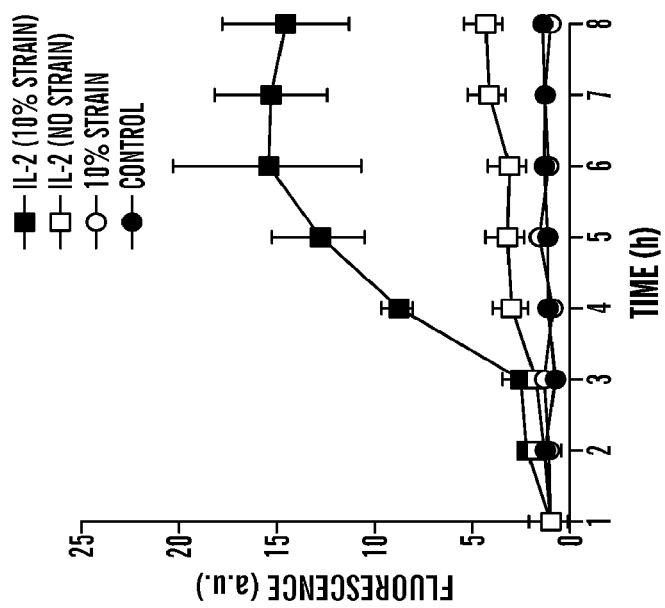

The inventors have demonstrated that the lung Chips that mimic the lung's dynamic mechanically active (breathing) microenvironment (e.g., using the device described in the PCT Application No.: PCT/US2009/050830 which has side channels to allow modulation of pressure to cause cyclic movement of the membrane on which the cells are seeded) can also effectively predict lung toxicity responses to the chemotherapeutic cytokine IL-2, which has a dose-limiting toxicity due to vascular leakage leading to pulmonary edema in humans. Using the lung-on-a-Chip with fluorescent-insulin as a marker of vascular permeability (fluid shifts), the IL-2 produces a small but significant increase in pulmonary vascular leakage into the air channel of the lung Chip under static conditions. However, with physiological breathing motions akin to normal breathing motions (10% cyclic strain), this response increases by more than 3-fold (and it was accompanied by blood clot formation as seen in humans), and the critical physiological importance of providing this correct mechanical microenvironment was demonstrated in studies in a mouse ex vivo ventilation-perfusion model that demonstrated a similar dependency of pulmonary edema induction by IL2 on breathing motions (FIG. 4). Using the lung-Chips, various kinds of drugs can be tested to determine what would be the effective treatment. In fact, the IL2-induced pulmonary toxicity in the Lung Chip can be pharmaceutically suppressed in vitro, and this device has been used to identify a TRPV4 inhibitor drug as a new suppressor of pulmonary edema (Huh et al., A Human Disease Model of Drug Toxicity-Induced Pulmonary Edema in a Lung-on-a-Chip Microdevice. Sci Transl Med. 2012 Nov. 7; 4(159):159ra147. doi: 10.1126/scitranslmed.3004249. PMID: 23136042 [PubMed—in process], content of which is incorporated herein by reference in its entirety. These results provide proof-of-principle for Organ Chips lined by human cells (e.g., Organ-specific parenchymal cells) as a means to predict clinically relevant toxicity responses in humans, as well as to identify new disease-preventing drug activities. Taken together with similar findings in relation to the toxicities of nanoparticles using the same Lung Chips (2), these data indicate that some clinically important Organ toxicities cannot be mimicked in vitro without providing the correct mechanical microenvironment, which is lacking from most current model systems.

Lung Airway Smooth Muscle Chips

Figure 5A:
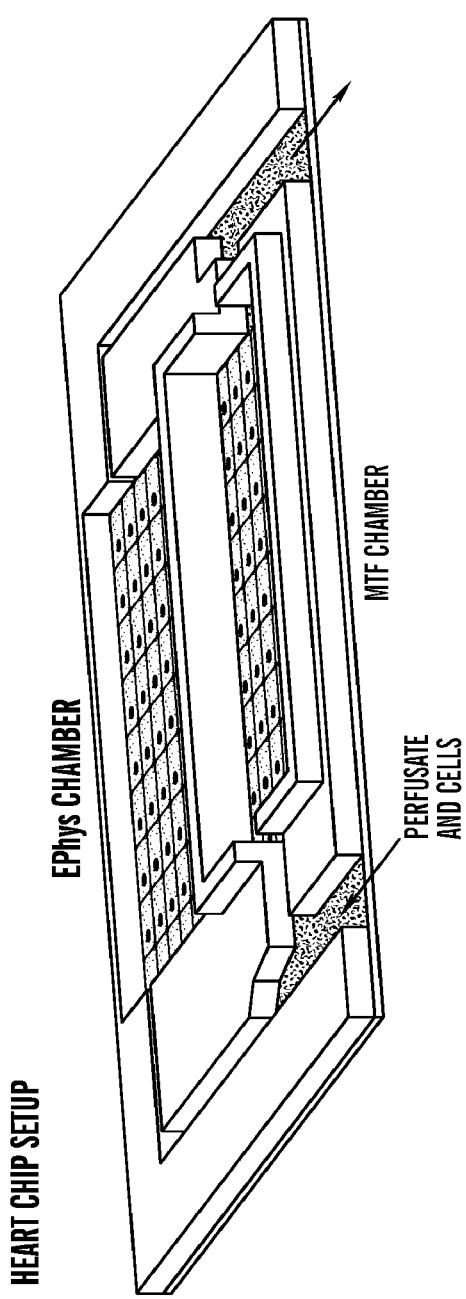
FIGS. 5A-5C are schematic representations of a heart-on-a-Chip.
Figure 5C:
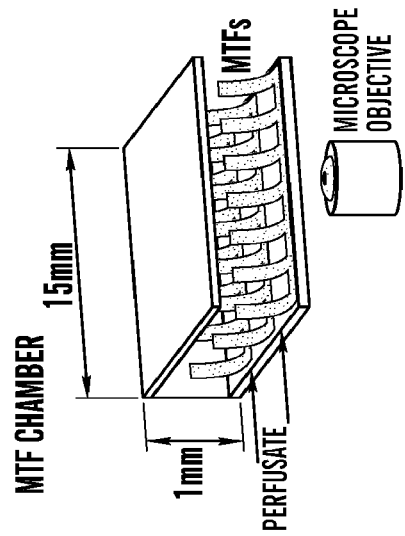
Figure 5B:
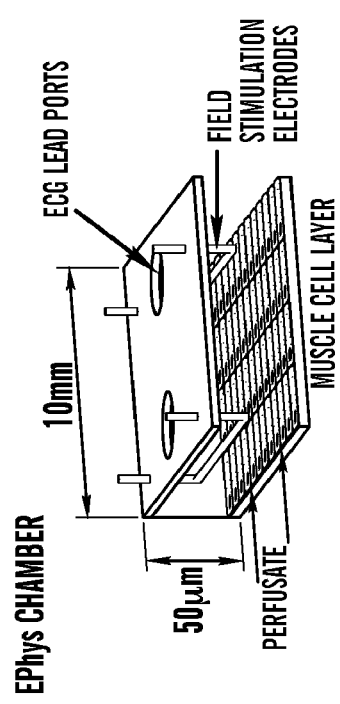
Figure 6A:
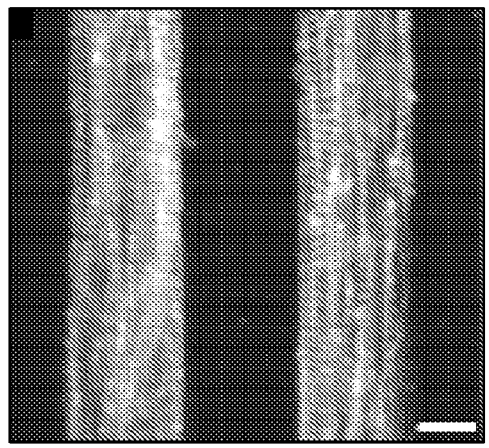
FIGS. 6A-6D show a contractile heart (muscle) Chip (FIG. 6A) that mimics the tissue Organization in a multiplexed array of muscular thin films (MTFs) (FIGS. 6B and 6C), which can be used to quantitate contractile stress in real-time (FIG. 6D).
Figure 6B:
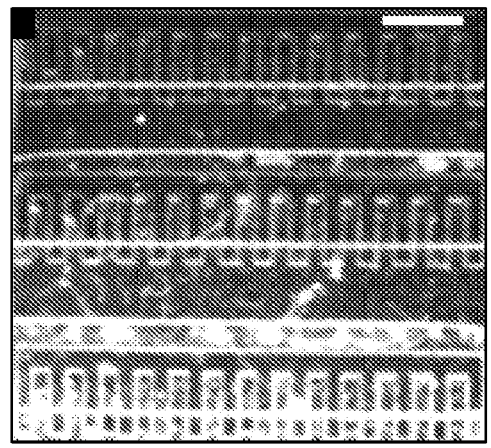
Figure 6C:
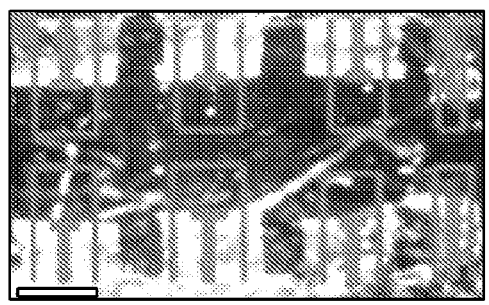
Figure 6D:
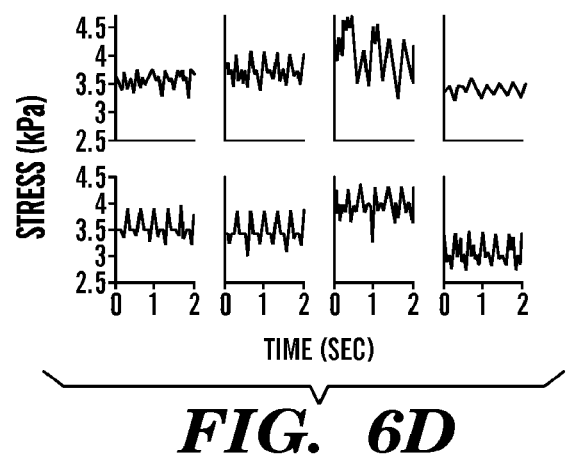
Figure 7:
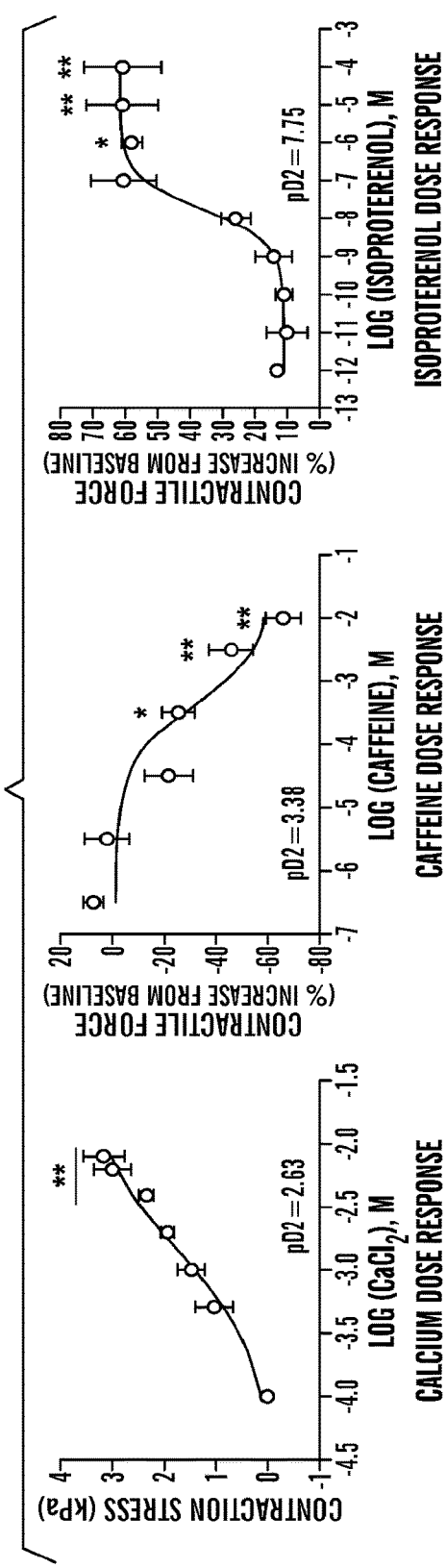
FIG. 7 depicts line graphs showing MTFs mimic of whole heart tissue drug responses. The top row shows the dose response of engineered neonatal rat ventricular tissues in the form of muscular thin films on the heart Chip, treated with calcium (left), caffeine (middle), and isoproterenol (right). The bottom row shows the response of adult rat ventricular strips.
Figure 7:
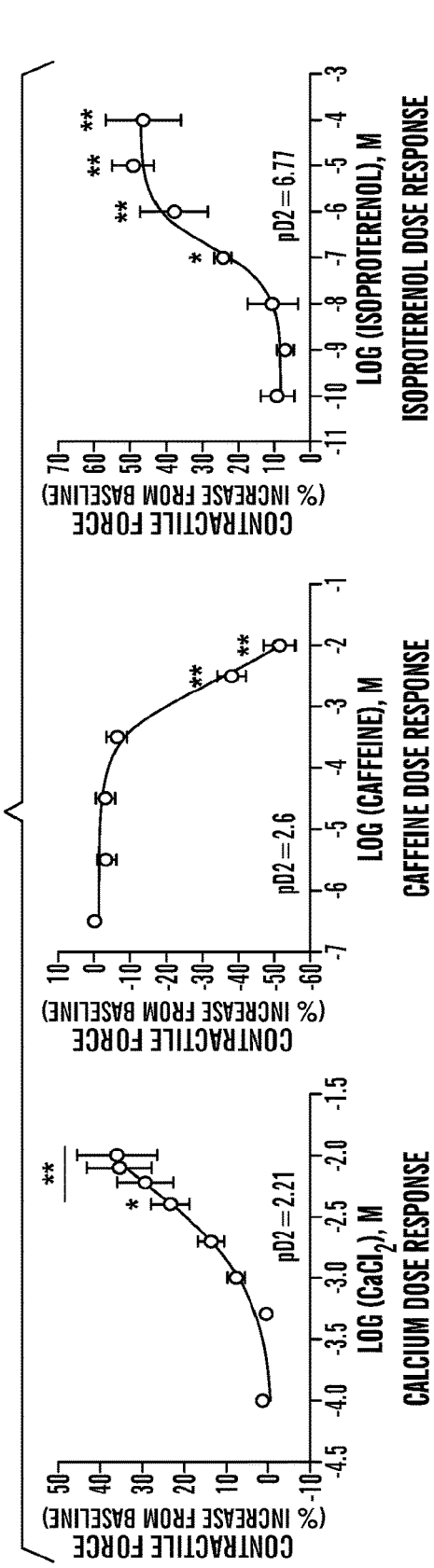
Figure 8A:
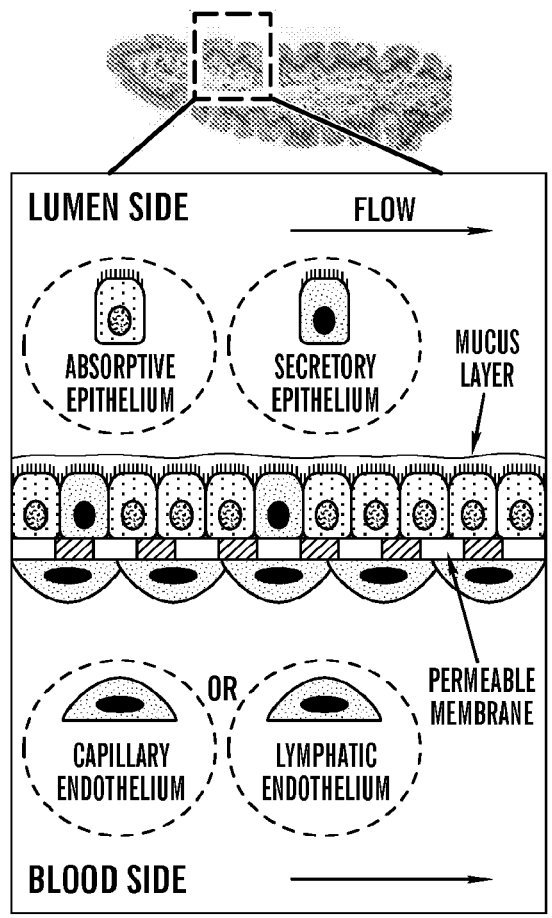
FIGS. 8A-8E depict gut-on-a-Chip functionality.
Figure 8B:
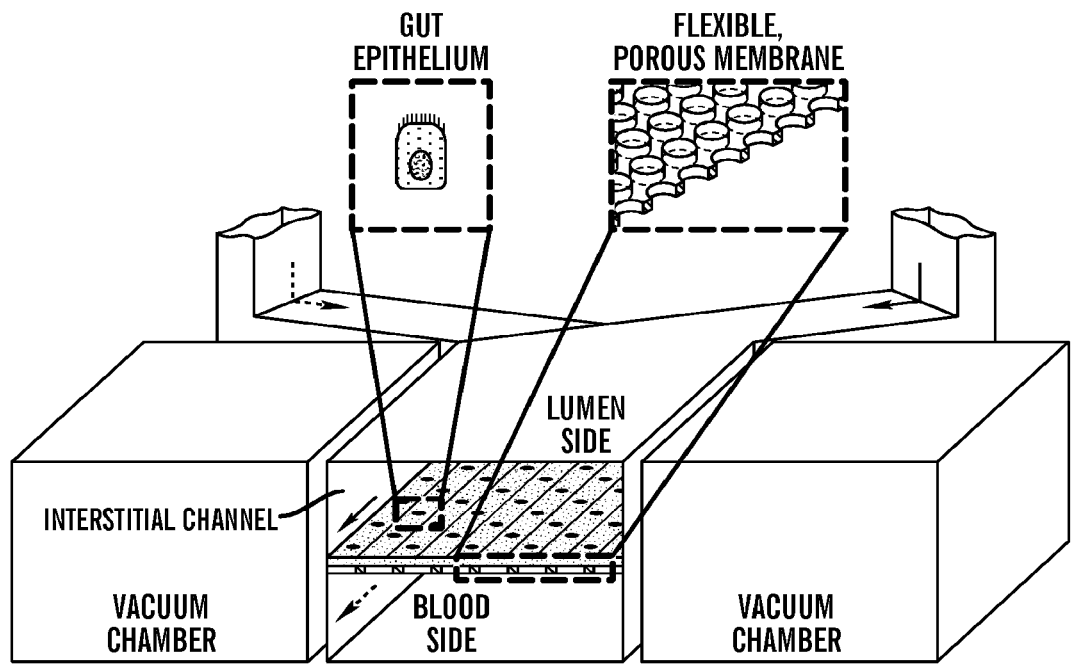
Figures 8C, 8D:
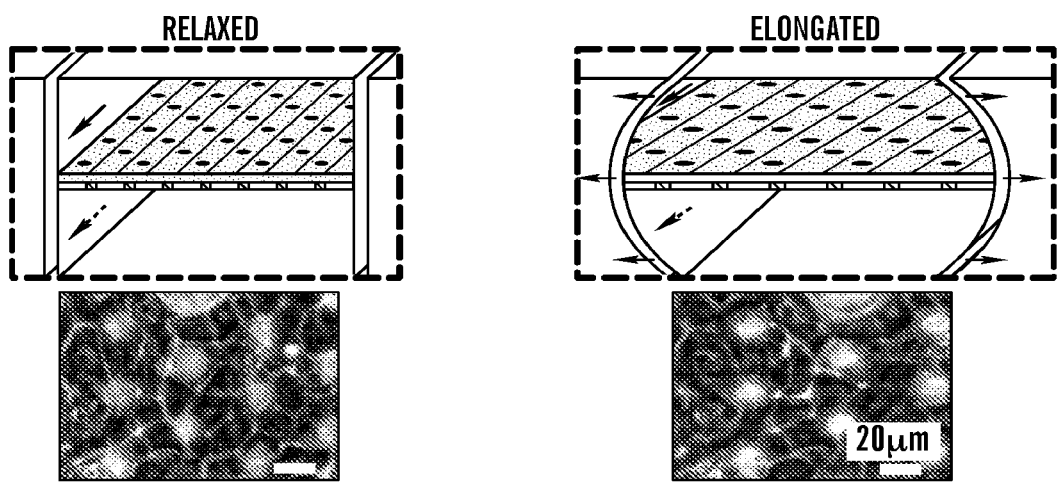
Figure 8E:
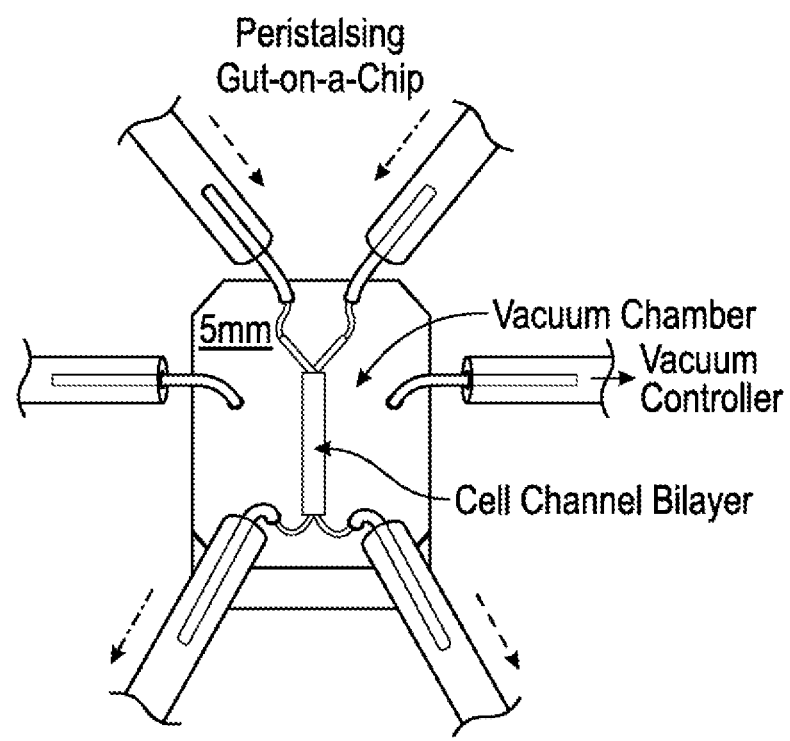

Without limitations, in some embodiments, the lung airway smooth muscle Chips can be developed based on the design of the Heart Chip (e.g., as shown FIGS. 5A-5C). In some embodiments, the lung airway smooth muscle Chips can be connected to the lung Chip to function as an integral Organ Chip. In some embodiments, the design of the lung airway smooth muscle can be incorporated into the lung Chip design.

Heart Organ Chips

In cardiac muscle, the parenchymal cells can include the myocardium, also known as cardiac muscle fibers or cardiac muscle cells, and the cells of the impulse connecting system, such as those that constitute the sinoatrial node, atrioventricular node, and atrioventricular bundle.

To fabricate heart Chips, in some embodiments, functional heart tissues are fabricated first and then multiplexed in a single microfluidic device. For example, functional heart tissues can be fabricated by culturing neonatal rat ventricular cardiomyocytes on elastomeric polymer thin films micropatterned with ECM proteins to promote spatially ordered, two-dimensional myogenesis and create "muscular thin films" (MTFs) as described previously in the literature (3,4). These heart tissue constructs are electrically functional and actively contractile, generating stresses comparable to those produced by whole papillary muscle, and the MTFs can be used to measure effects on heart cell contractile function in vitro during electrical and pharmacological stimulation (4). The MTFs can then be multiplexed, e.g., in an array, within a microfluidic Chip (FIGS. 5 and 6).

In another embodiment, multi-layered Heart Chips can be constructed. For example, a multi-layered Heart Chip can contain a Microvascular Channel lined by human endothelium adherent to a porous membrane that separates it from the MTF-lined "Interstitial Channel," such as similar to the configuration of the lung Chip (FIG. 3). The inventors have demonstrated that microengineered MTFs effectively mimic pharmacological responses of adult rat papillary muscle strips (FIGS. 5A-5C), which are commonly used to screen cardiac tissue responses to drugs by the pharmaceutical industry.

In some embodiments, the heart Chips can further comprise heart-specific parenchymal cells, e.g., cardiomyocytes, to further mimic the physiological environment and/or function of the heart. The cardiomyocytes can be isolated from a tissue or obtained from a commercial source, or by differentiating stems cells to cardiomyocytes, e.g., induced pluripotent stem cell-derived cardiomyocytes.

In particular embodiments, the heart Chips can be modified for various analyses. For example, the Heart Chips can have at least one set of MTF-lined Interstitial Channels for optical imaging and contractility analysis. Additionally, the heart Chips can have at least one parallel set of larger Interstitial Channels lined by one or a plurality of electrodes (e.g., platinum electrodes) as an "Electrophysiological Chamber" for electrical pacing and analysis of changes in cardiac electrical potential with a lead electrocardiogram (FIGS. 5A-5C). Without wishing to be bound by theory, in some embodiments, both the Interstitial Channels and Electrophysiological Chambers can be fed by single medium stream introduced through an underlying endothelium-lined microvascular channel, e.g., in a configuration similar to the lung Chips (see, for example, FIG. 3). Exemplary heart Chips are described, for example in U.S. Provisional Patent Application Ser. No. 61/569,028, filed on Dec. 9, 2011, U.S. Provisional Patent Application Ser. No. 61/697,121, filed on Sep. 5, 2012, and PCT patent application titled "Muscle Chips and Methods of Use Thereof," filed on Dec. 10, 2012 and which claims priority to the U.S. provisional application No. 61/569,028, filed on Dec. 9, 2011, U.S. Provisional Patent Application Ser. No. 61/697,121, the entire contents of all of which are incorporated herein by reference.

Skeletal Muscle Organ Chips

In striated muscle, the parenchymal cells can include myoblasts, satellite cells, myotubules, and myofibers. Without limitations, in some embodiments, the skeletal muscle Chips can be developed based on the design of the Heart Chip or Muscle Chip as described herein and as shown FIGS. 5A-5C.

Liver Organ Chips

In a liver Organ, the parenchymal cells include hepatocytes, Kupffer cells, and the epithelial cells that line the biliary tract and bile ductules. The major constituent of the liver parenchyma are polyhedral hepatocytes (also known as hepatic cells) that present at least one side to an hepatic sinusoid and opposed sides to a bile canaliculus. Liver cells that are not parenchymal cells include cells within the blood vessels such as the endothelial cells or fibroblast cells.

In some embodiments, the human Liver Chip can be modified from the basic Lung Chip multichannel design (e.g., as shown in FIG. 3). For example, commercially available human hepatocytes (e.g., from Invitrogen) or patient-specific hepatocytes (isolated from a tissue) can be placed on one side of the ECM (e.g., laminin, type IV collagen or Matrigel)-coated membrane, and human microvascular endothelial cells on the other side. Without wishing to be bound by theory, the porous membrane, basement membrane and cell-cell junctions of the endothelium can facilitate physiologically relevant mass transport while protecting hepatocytes from fluid shear stress and serum components in the Microvascular Channel.

In some embodiments, the liver Chips can further comprise other parenchymal cells, such as Kupffer cells (resident macrophages of the liver) under the endothelium in the Liver Chip.

Without wishing to be bound by theory, oxygen gradients are essential determinants of normal liver physiology and function, as well as key contributors to acute and chronic hepatoxicity. Accordingly, in some embodiments, oxygen gradients found in vivo can be incorporated in the liver Chips. By way of example only, oxygen gradients can be generated in a liver Chip (e.g., made of a gas-permeable material, e.g., PDMS, which is permeable to gases) by flowing oxygen at different concentrations through the two side channels. Other microengineering methods, for example, as described in Adler M. et al. *Lab Chip* 2010; 10(3): 388-389 and Chen Y-A et al., *Lab Chip* 2011; 11: 3626-3633, can also be used to develop oxygen gradients within the Organ Chips.

In some embodiments, bile canalicular networks in pre-determined patterns can be integrated into liver Chips, such that they can be coupled with microscale sampling ports in the liver Chips. Such configuration can be used to determine intrinsic biliary clearance. This approach can be used to facilitate analysis of interplay between drug transporters and drug metabolizing enzymes, which is a key determinant of drug PK properties and toxicity profiles in humans.

Gut Organ Chips

In some embodiments, the gut Chips as shown in FIGS. 8A-8E can use a porous membrane (e.g., PDMS membrane) coated with ECM (e.g., Collagen I+Matrigel) that is lined by human intestinal epithelial cells and cultured under flow conditions to produce a physiological shear stress (~0.02 dyne/cm$^2$) while simultaneously exerting cyclic mechanical strain (10% elongation, 0.15 Hz). Human CaCo2 cells cultured under these conditions can differentiate by changing their entire transcriptome (measured using gene microarrays) and form 3D villus structures that match the height of the microfluidic Interstitial Channel (FIGS. 8A-8E). In addition, the physiologically relevant conditions recreated in the Gut Chip can enable one to culture living gut bacteria (e.g., human gut-derived *Lactobacillus* GG or a mixture of other human gut microflora) directly on top of the living human villus gut epithelium, and hence open the possibility to interrogate the influence of gut microbiome on drug absorption and metabolism using the gut Chips.

In the parenchyma of the gastrointestinal tract such as the esophagus, stomach, and intestines, the parenchymal cells can include epithelial cells, glandular cells, basal, and goblet cells.

Other gut Chips, e.g., as described in the Provisional Application No.: U.S. 61/447,540, can also be used in the various aspects and embodiments described herein. For example, the gut Chips as described, for example, in Provisional Application No.: U.S. 61/447,540 can be used in the Organ Cartridge, the Organ Farm and/or the Organ Interrogator to facilitate nutrient exchange between the gut and other Organs.

Kidney Organ Chips

Without limitations, in some embodiments, the kidney Chips can be developed based on the lung Chips as shown in FIG. 3 or described in the PCT Application No.: PCT/US2009/050830. In such embodiments, the kidney Chips can use a porous membrane (e.g., a PDMS membrane) coated with ECM (e.g., type IV collagen) that is lined by primary human proximal tubular epithelial cells (e.g., obtained from Biopredic) and cultured under flow conditions to produce a physiological shear stress (~0.02 dyne/cm$^2$).

Using such kidney Chips, the in vivo toxicity observed with cisplatin and its inhibition by cimetidine can be recapitulated and clinically relevant endpoints, such as KIM-1, can be measured.

In the kidney, parenchymal cells can include cells of collecting tubules and the proximal and distal tubular cells.

Other kidney Chips, e.g., as described in the Provisional Application No.: U.S. 61,449,925, the content of which is incorporated herein by reference in its entirety, can also be used in the Organ C Cartridge, the Organ Farm and/or the Organ Interrogator.

Skin Organ Chips

In the skin, the parenchymal cells can include the epithelial cells of the epidermis, melanocytes, cells of the sweat glands, and cells of the hair root.

In some embodiments, the cells seeded in the skin Chips can be further induced to differentiate into a stratified epithelium with basal, spinous and cornified layers, e.g., by passing air through the "Interstitial Channel" in a similar fashion as operated in the lung Chip, and creating an air-liquid interface.

Without limitations, in some embodiments, the skin Chips can be developed based on the lung Chips as shown in FIG. 3 or described in the PCT Application No.: PCT/US2009/050830. An exemplary Skin Organ Chip that recreates the functional human skin model is previously described in ref. (9). In some embodiments, human foreskin fibroblasts can be plated in a collagen gel on one side of the membrane, and human dermal endothelial cells on the other side of the membrane; human keratinocytes from foreskin can then be plated on top of the collagen gel layer.

Brain Organ Chips

Figure 9:
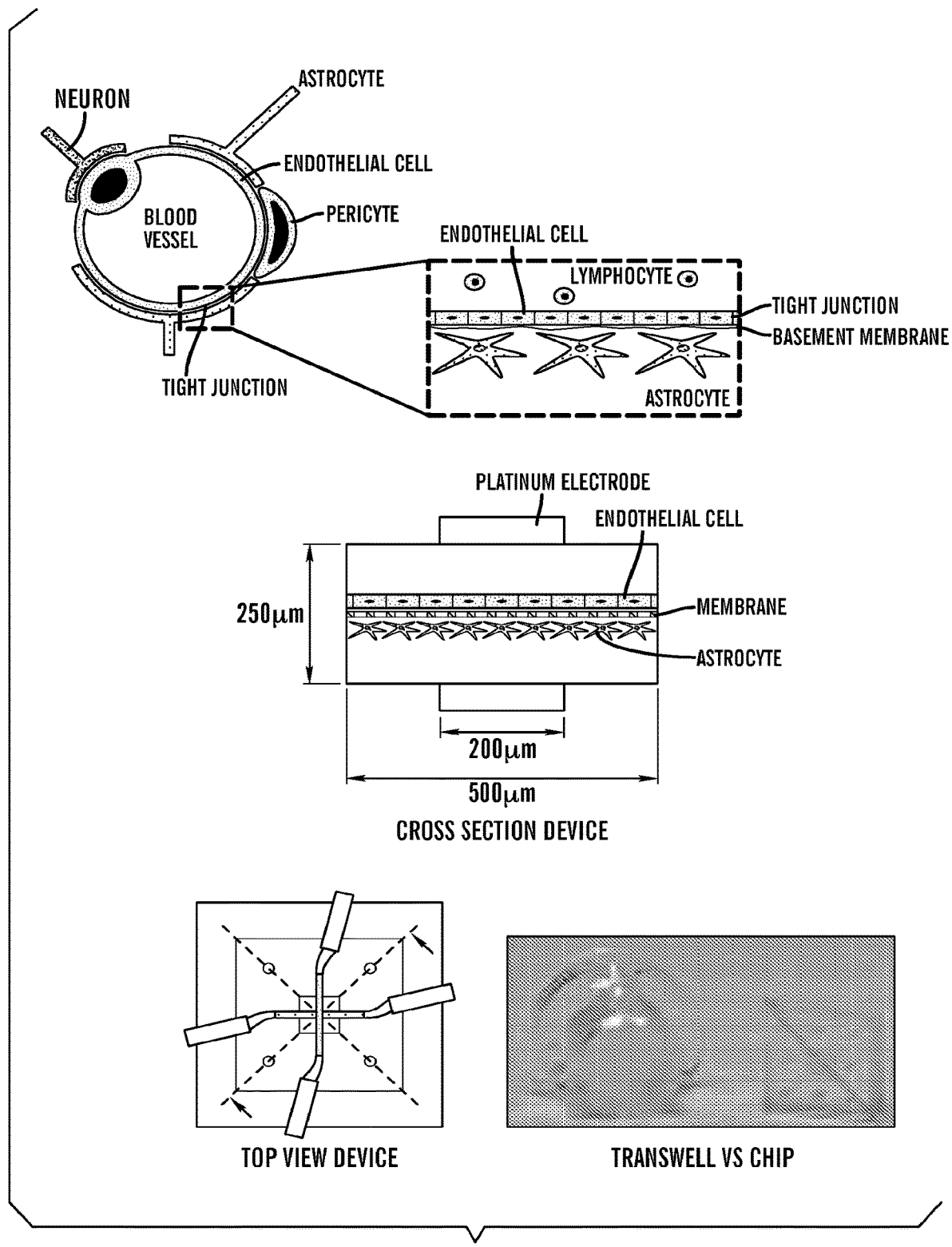
FIG. 9 shows the architecture of the human blood-brain barrier. The normal architecture of the Human Blood Brain Barrier (top) is mimicked by culturing human endothelium on one side of a porous membrane and human astrocytes on the other within a microfluidic channel with embedded platinum electrodes within an Organ Chip (bottom).

Without limitations, in some embodiments, the brain Chips can be developed based on the lung Chips as shown in FIG. 3 or described in the PCT Application No.: PCT/US2009/050830. For example, a brain Chip can be constructed by first creating a Blood-Brain Barrier (BBB) in which human astrocytes are cultured on one side of a porous ECM-coated membrane and human endothelial cells on the other side of the porous membrane. The inventors have demonstrated generation of an effective permeability barrier, as measured by transepithelial resistance using this approach (FIG. 9).

In alternative embodiments, the brain Chips can be developed based on the design of the Heart Chip (e.g., as shown FIGS. 5A-5C). Such brain Chips can be constructed, e.g., by placing the BBB in one set of channels and then linking the outflow of its Interstitial Channel to a second electrophysiological chamber where human brain neuronal networks can be cultured to measure effects on nerve cell toxicity and electrical signaling. Without limitations, these brain Chips can be also used as a Traumatic Brain Injury (TBI) model to develop new therapies.

Testis Organ Chips

Without limitations, in some embodiments, the Testis Chip can employ the Lung Chip design as described earlier (e.g., FIG. 3) with human Sertoli and Leydig cells being cultured on one side of the porous ECM-coated membrane and endothelium on the other side of the coated membrane. This Testis Chip design can maintain enhanced differentiated testicular functions when the two parenchymal cell types are combined in this manner (10).

Bone Marrow Organ Chips

Figure 10:
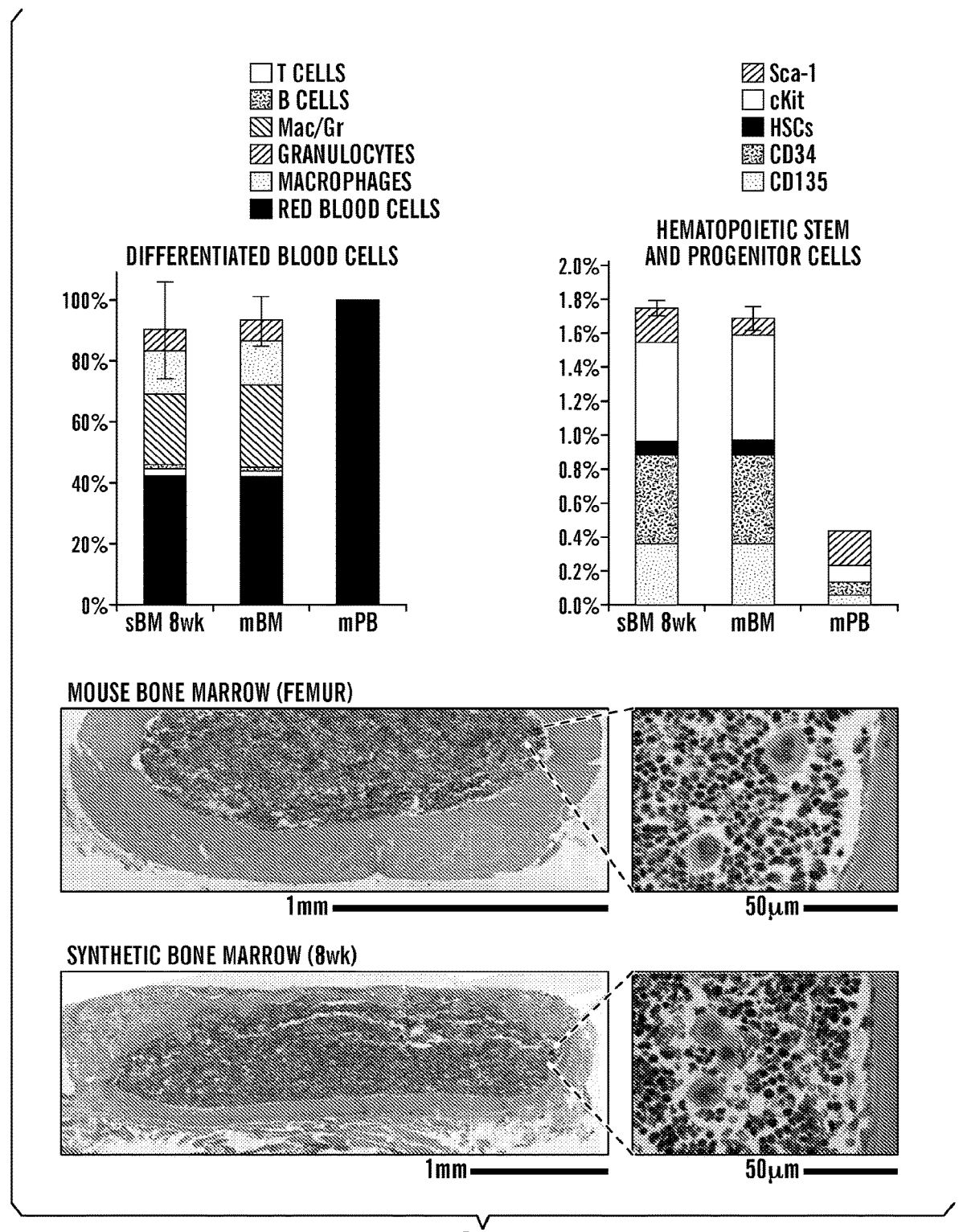
FIG. 10 shows that Synthetic Bone Marrow (sBM) fully recapitulates natural mouse bone marrow (mBM) and not peripheral blood (mPB) 8 weeks after implanting DMP/BMPs subcutaneously. Similar functionality is maintained in vitro by culturing removed sBM in a microfluidic device.

To construct a Bone Marrow Chip, fully functional bone containing a central marrow can be formed in vivo first by implanting demineralized bone powder and BMPs ⅔ subcutaneously above a muscle layer within a polymer mold (e.g., PDMS mold and culturing it for about 4-8 weeks in vivo. Additional details of the bone marrow Chips and methods of making the same can be found in the U.S. Provisional Application No.: U.S. 61,492,609, the content of which is incorporated herein by reference in its entirety. The bones that form in these implanted devices can take the cylindrical shape of the flexible mold, and contain a fully developed bone marrow with normal morphology and cellular composition (hematopoietic stem cells, progenitor cells, various differentiated blood cell types), when compared to normal mouse bone marrow versus peripheral blood (FIG. 10). The formed marrow can be maintained by placing the formed implant within microfluidic channels, as evidenced by cells isolated from this marrow after 4 days in culture being able to regenerate a functional marrow and reconstitute whole blood formation in gamma-irradiated mice.

Alternatively, simultaneously reconstituting the mouse's injured marrow and forming new marrow in the microfluidic implants can be carried out by irradiating immuno-compromised mice, implanting the demineralized bone powder with BMPs subcutaneously, and then injecting human bone marrow. Once removed and maintained in microfluidic systems, the human marrow can then be used to generate all types of blood cells, which can circulate throughout the entire linked Organ Chip circuit, e.g., for studies on inflammation and its relation to drug toxicity.

Additional Organ Chips

Without limitations, additional Organ Chips corresponding to other Organs, e.g., spleen Chips for filtration of fluid, e.g., blood, as described into the U. S. Provisional No.: U.S. 61,470,987, the content of which is incorporated here by reference in its entirety can also be used.

In spleen, thymus, lymph nodes and bone marrow, the parenchymal cells can include reticular cells and blood cells (or precursors to blood cells) such as lymphocytes, monocytes, plasma cells and macrophages.

In a pancreas, the parenchymal cells can include cells within the acini such as zymogenic cells, centroacinar cells, and basal or basket cells and cells within the islets of Langerhans such as alpha and beta cells.

In the prostate, the parenchyma can include epithelial cells.

In glandular tissues and Organs, the parenchymal cells can include cells that produce hormones. In the parathyroid glands, the parenchymal cells can include the principal cells (chief cells) and oxyphilic cells. In the thyroid gland, the parenchymal cells can include follicular epithelial cells and parafollicular cells. In the adrenal glands, the parenchymal cells can include the epithelial cells within the adrenal cortex and the polyhedral cells within the adrenal medulla.

Functional Assessments of Organ Chips

The viability and function of all tissues can be assessed morphologically, e.g., with optical imaging. In addition, the alveolar-capillary interface function of the Lung Chip can be measured, e.g., by quantifying permeability barrier function (e.g., using TEER and molecular exclusion), measuring surfactant production, and demonstrating physiological relevant responses to cytokines (e.g., ICAM1 expression in response to TNFα). See ref (2). Heart muscle function can be characterized, e.g., using force-frequency curves, measuring increases in peak contraction stress as a function of increasing field stimulation frequency, and analyzing electrocardiogram results during the same protocol to ensure that the tissues are functioning electrically. See ref (4). Functionality of the Liver Chip can be assessed, e.g., via multiple well-established assays including albumin secretion, transporter expression and function (efflux and uptake transporters), and CYP450 expression. Specific CYP450 enzymes can be determined by incubation with FDA-approved probe substrates (1), and specific metabolite formation for each CYP450 isoform can be measured and validated using LC/MS. Response of hepatocytes to prototypical CYP450 inducers (i.e., Rifampacin for CYP3A4) can be assessed. Organ Chips that can be opened for inspection at the end of an experiment can have their cells studied for protein expression by laser capture microdissection or matrix-assistance laser ablation ionization (MALDI) mass spectrometry.

Based on the functional assessments, one of skill in the art can adjust the condition of the Organ Chips, e.g., by modulating the flow rate of fluid (fluid shear stress), nutrient level, degree of oxygenation or acidification, addition of specific metabolites to adjust intracellular signaling levels, mechanical stimulation, cell seeding density on the membranes, cell types, ECM composition on the membrane, dimension and/or shapes of the channels, oxygen gradient and any combinations thereof, to modulate the functional outcome of the Organ Chips. The Perfusion Controller and MicroClinical Analyzer in FIGS. 12 and 18 and the Microscope Blade in FIG. 21 and the Organ Interrogator in FIG. 22 can enable the sensing and control required to adjust the condition of the Organ Chips.

Human Cell Sources

The cells used in the Organ Chips can be isolated from a tissue or a fluid using any methods known in the art, or differentiated from stems cells, e.g., embryonic stem cells, or induced pluripotent stem cells (iPSC), or directly differentiated from somatic cells. Alternatively, the cells used in the Organ Chips can be obtained from commercial sources, e.g., Cellular Dynamics International, Axiogenesis, Gigacyte, Biopredic, InVitrogen, Lonza, Clonetics, C D I, and Millipore, etc.).

In some embodiments, the cells used in the Organ Chips can be differentiated from the "established" cell lines that commonly exhibit poor differentiated properties (e.g., A549, CaCo2, HT29, etc.). These "established" cell lines can exhibit high levels of differentiation if presented with the relevant physical microenvironment (e.g., air-liquid interface and cyclic strain in lung, flow and cyclic strain in gut, etc.), e.g., in some embodiments of the Organ Chips.

Organ Cartridge

One aspect provided herein relates to Organ Cartridges. Organ Cartridges can be used as stand-alone microphysiological system or can act as an interface between at least one Organ Chip disposed thereon and a Cartridge Dock, an Organ Farm or an Organ-Interrogator device. Organ Cartridges can be designed for use in either an Organ Farm instrument, e.g., for establishing long-term culture, or in an Organ Interrogator, e.g., for further culture and/or analysis. In some other embodiments, the Organ Cartridges comprise a thermal controller and can be used as Organ Farm without needing an external incubator. Some exemplary Organ Cartridges are shown in FIGS. 12-17.

Figure 11:
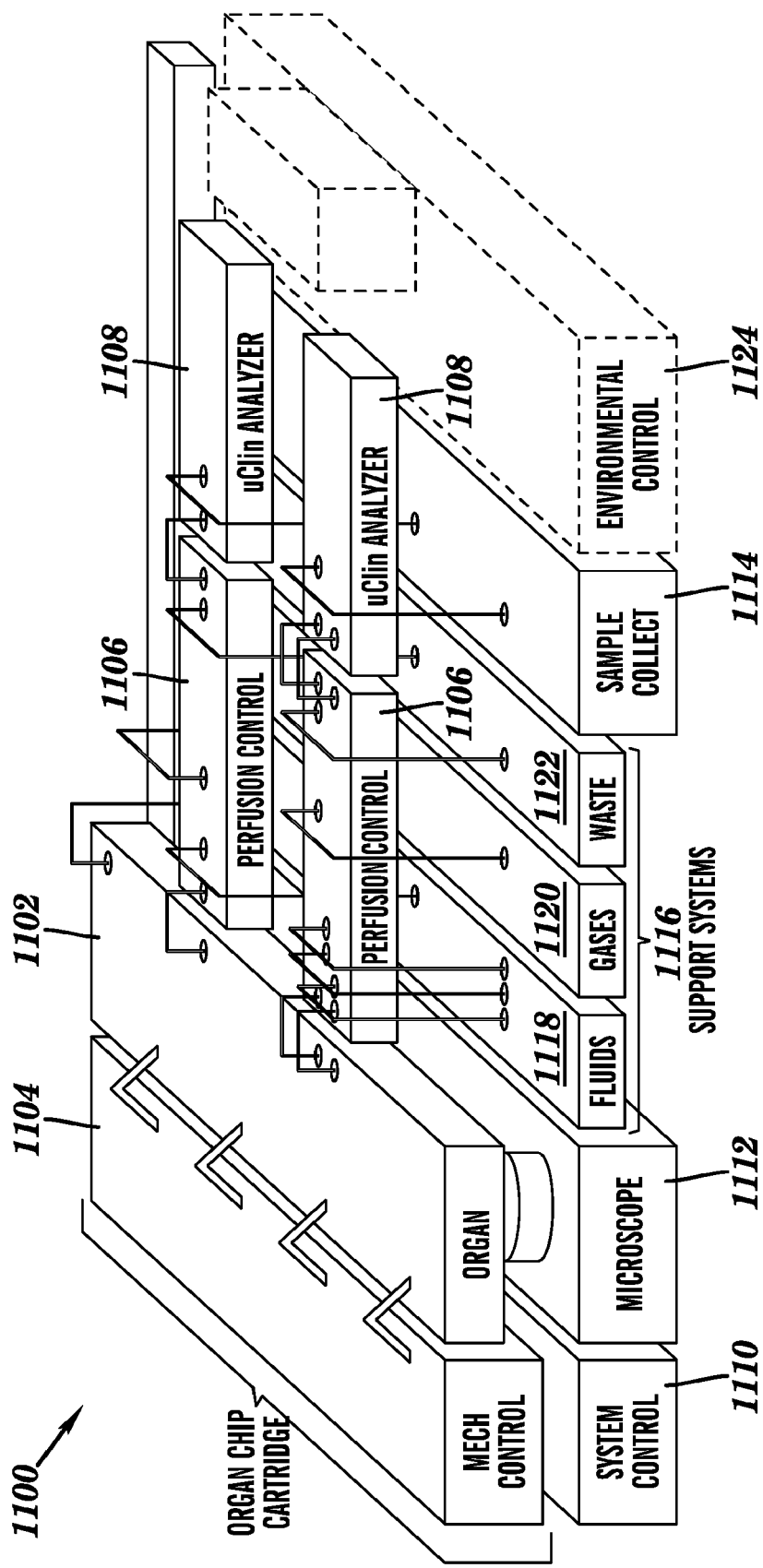
FIG. 11 is a schematic representation of a Organ Cartridge according to an embodiment of the invention. The Organ Cartridge is shown with mechanical, electrical, fluidic, and pneumatic control of the Organ Chip, including, for example, a separate perfusion controller and a microclincal analyzer for each compartment of an Organ that has two compartments separated by a membrane, e.g. the interstitial and microvascular compartments.
Figure 13B:
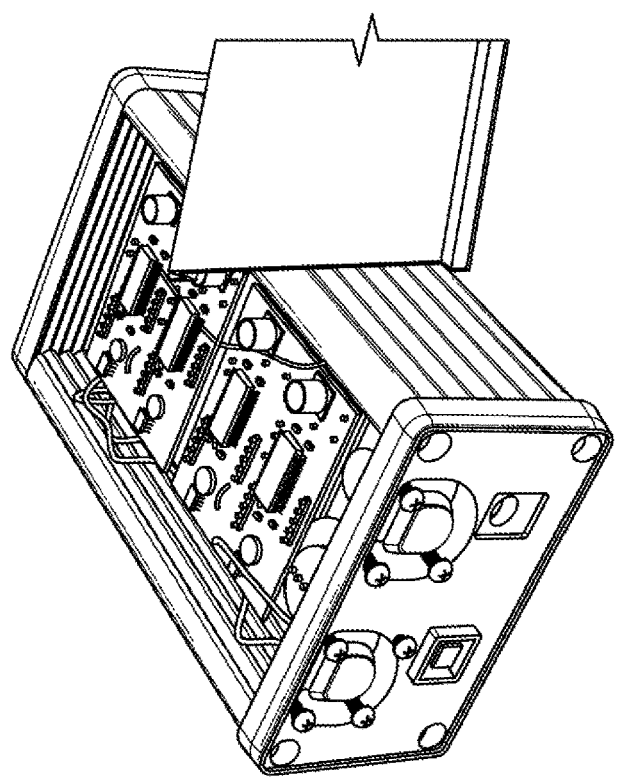
FIGS. 13A-13E show another embodiment of the RPPM technology developed with smaller motor architecture, automated pump testers, and control software.
Figure 13A:
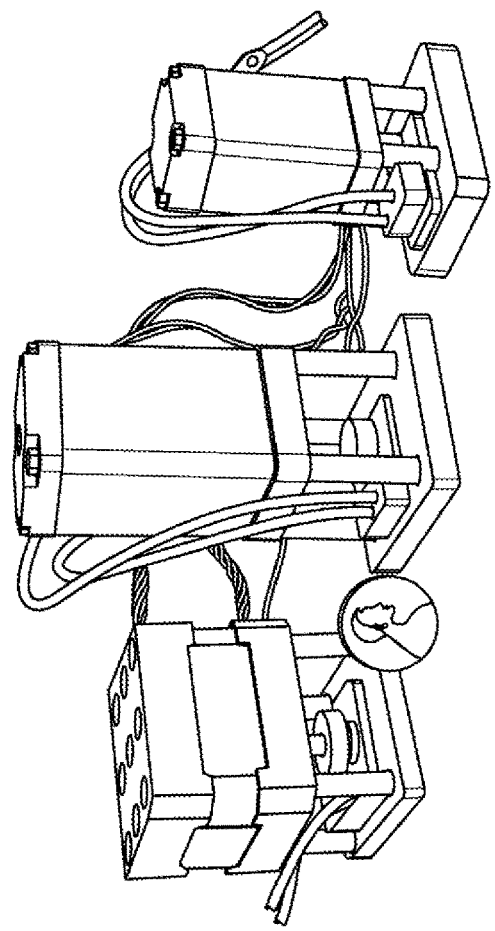
Figure 13C:
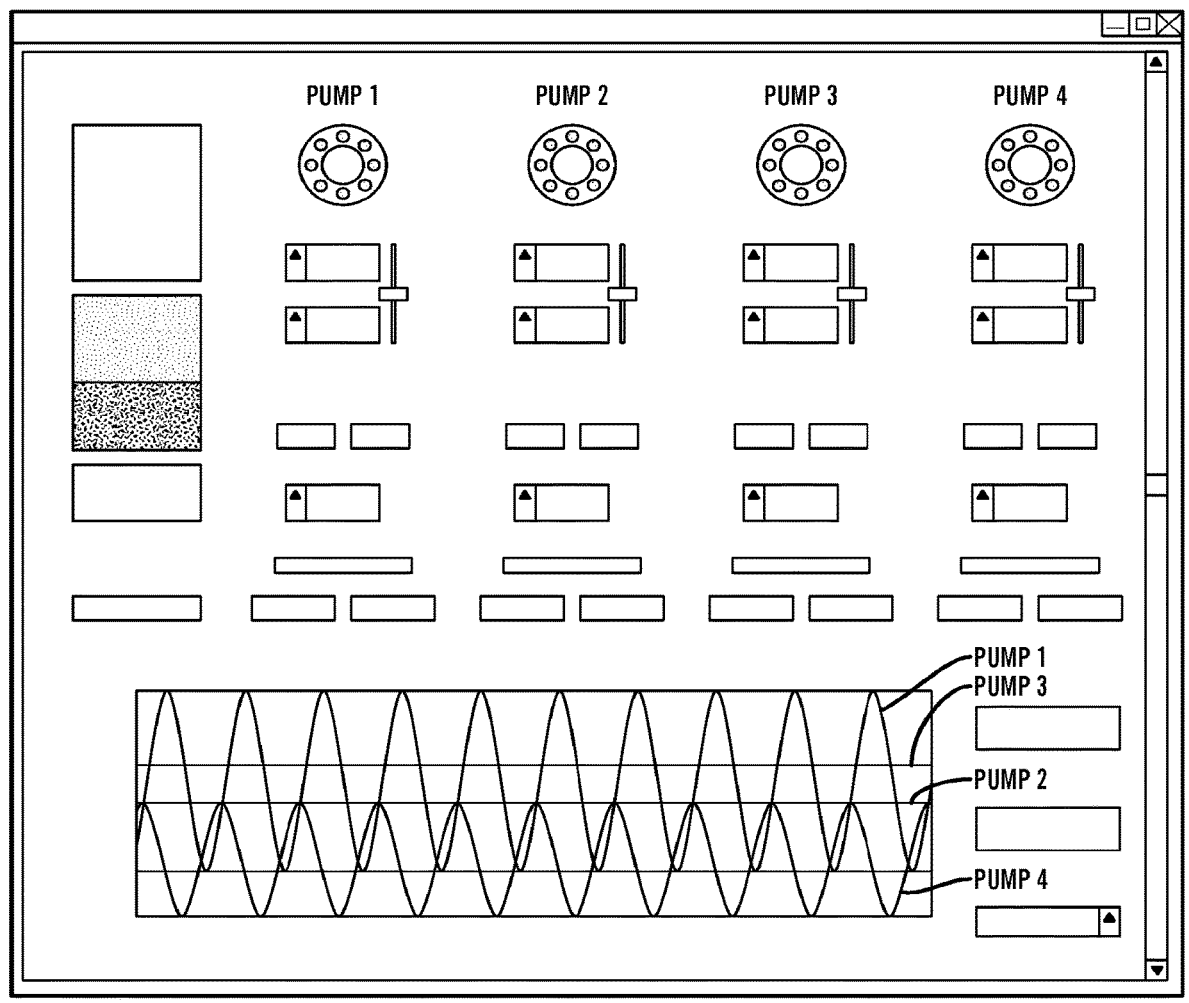
Figure 13E:
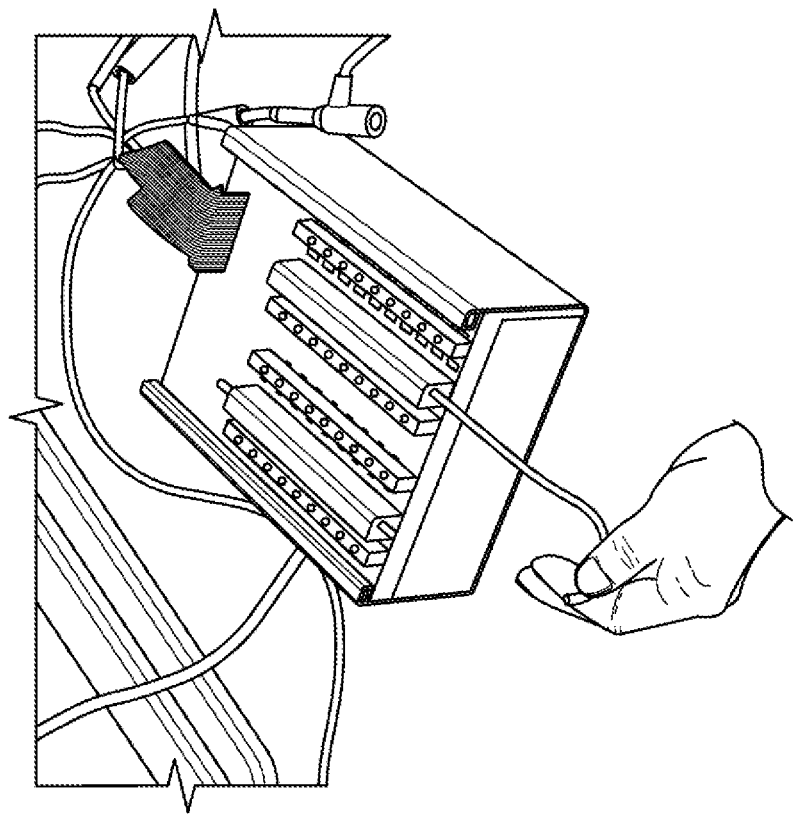
Figure 13D:
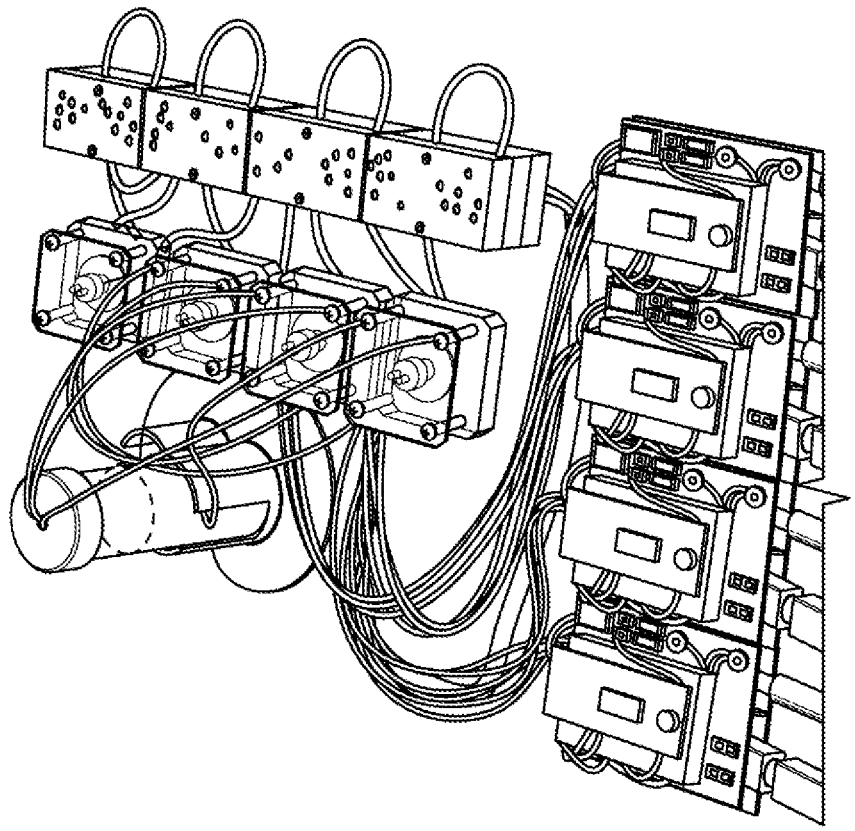

Generally, an Organ Cartridge comprises a base substrate. The base substrate provides (a) a holder and microfluidic connections for at least one Organ Chip or a port adapted for the Organ Chip disposed thereon; and (b) at least one fluidic circuit having an inlet and an outlet, in connection with the at least one Organ Chip or the corresponding port. In some embodiments, the fluidic circuit can further allow fluid communication between the Organ Chips disposed on the Organ Cartridge and/or between the Organ Cartridges (FIG. 11).

In some embodiments, the Organ Chip disposed on the Organ Cartridge is integrated into the Organ Cartridge, i.e., the Organ Chip is part of the Organ Cartridge itself.

In some embodiments, one Organ Chip disposed on each Organ Cartridge can function as a whole Organ, and thus a plurality of the Organ Cartridges, each representing a different Organ, can be connected together to function as an integrated Microphysiological System or network. In some embodiments, two or more Organ Chips that each function as a different Organ can be disposed on the same Organ Cartridge, and thus the Organ Cartridge by itself can function as an integrated microphysiological network.

In some embodiments, two or more (e.g., two, three four, five, six, seven, eight, nine, ten or more) Organ Chips can be interconnected to form different aspects of the same Organ. For example, different Organ Chips can be interconnected to form lung alveoli and lung small airways. Without limitations, Organ Chips forming the different aspects of the same Organ can be present on different Organ Cartridges or on the same Cartridge.

In some embodiments, the Organ Chips disposed on the Organ Cartridge can perform the same and/or a different Organ-level function. Examples of Organ-level functions include, but are not limited to, functions of lung, gut, kidney, liver, skin, skeletal muscle, brain, bone marrow, spleen, and reproductive system (e.g., testis). Different parts of the same Organ also can be represented by different Organ Chips, such as one lung Chip that models the air sac or alveolar-capillary interface and another that mimics the small lung airway lined epithelium and surrounded by smooth muscle and endothelium.

In one embodiment, the microfluidic connections for the Organ Chip or the port adapted for the Organ Chip disposed on the Cartridge can be located toward the outer edge of the Organ Cartridges. It is to be understood that use of an Organ Cartridge is not necessary and Organ Chips can be used without the Organ Cartridge.

In some embodiments, an Organ Chip can be integrated into the Organ Cartridge as a single integral unit. In other embodiments, the Organ Chips can be separated from the Organ Cartridges and loaded onto the Organ Cartridges prior to use.

Organ Cartridge(s) can reside in a Cartridge Dock. The Cartridge Dock can be thermally regulated by an Organ Farm instrument, e.g., for further long-term culture, or an Organ-Interrogator, e.g., for further long-term culture and/or analysis. The Organ Cartridge can also be thermally regulated by an on-board thermal control.

Without limitations, the Organ Cartridge can have a holding capacity and connections/ports for one-or more (e.g., one, two, three, four, five, six, seven, eight, nine, ten, eleven, twelve, thirteen, fourteen, fifteen, twenty or more) Organ Chips. Accordingly, in some embodiments, the Organ Cartridges can comprise one or more (e.g., one, two, three, four, five, six, seven, eight, nine, ten, eleven, twelve, thirteen, fourteen, fifteen, twenty or more) Organ Chips disposed thereon.

In accordance with the invention, the Organ Cartridge can comprise at least one (e.g., one, two, three, four, five, six, seven, eight, nine, ten, eleven, twelve, thirteen, fourteen, fifteen, twenty or more) Organ Chips. In some embodiments, the Organ Chips disposed on the Organ Cartridge can function as a whole Organ, and thus a plurality of the Organ Cartridges, each representing a different Organ, can be connected together to function as an integrated Microphysiological System or network. In some other embodiments, the Organ Cartridge can comprise a plurality of Organ Chips, wherein different Organ Chips disposed on the Organ Cartridge can each function as a different Organ, and thus the Organ Cartridge by itself can function as an integrated microphysiological network.

In some embodiments, different Organ Chips disposed on the Organ Cartridge can perform the same and/or a different Organ-level function. Examples of Organ-level functions include, but are not limited to, functions of lung, gut, kidney, liver, skin, skeletal muscle, brain, bone marrow, spleen, and reproductive system (e.g., testis).

In some embodiments, at least a portion of the fluidic circuit can be in-Cartridge, i.e., integrated with the base substrate of the Organ Cartridge. In other embodiments, a portion of the fluidic circuit can be incorporated into the support device, e.g., the Organ Farm and/or the Organ-Interrogator.

In some embodiments, one or more of the fluid control elements can be in-Cartridge fluid control elements. In other embodiments, one or more of the fluid control elements can be external control elements that are adaptably connected to the Organ Cartridge.

Figure 17:
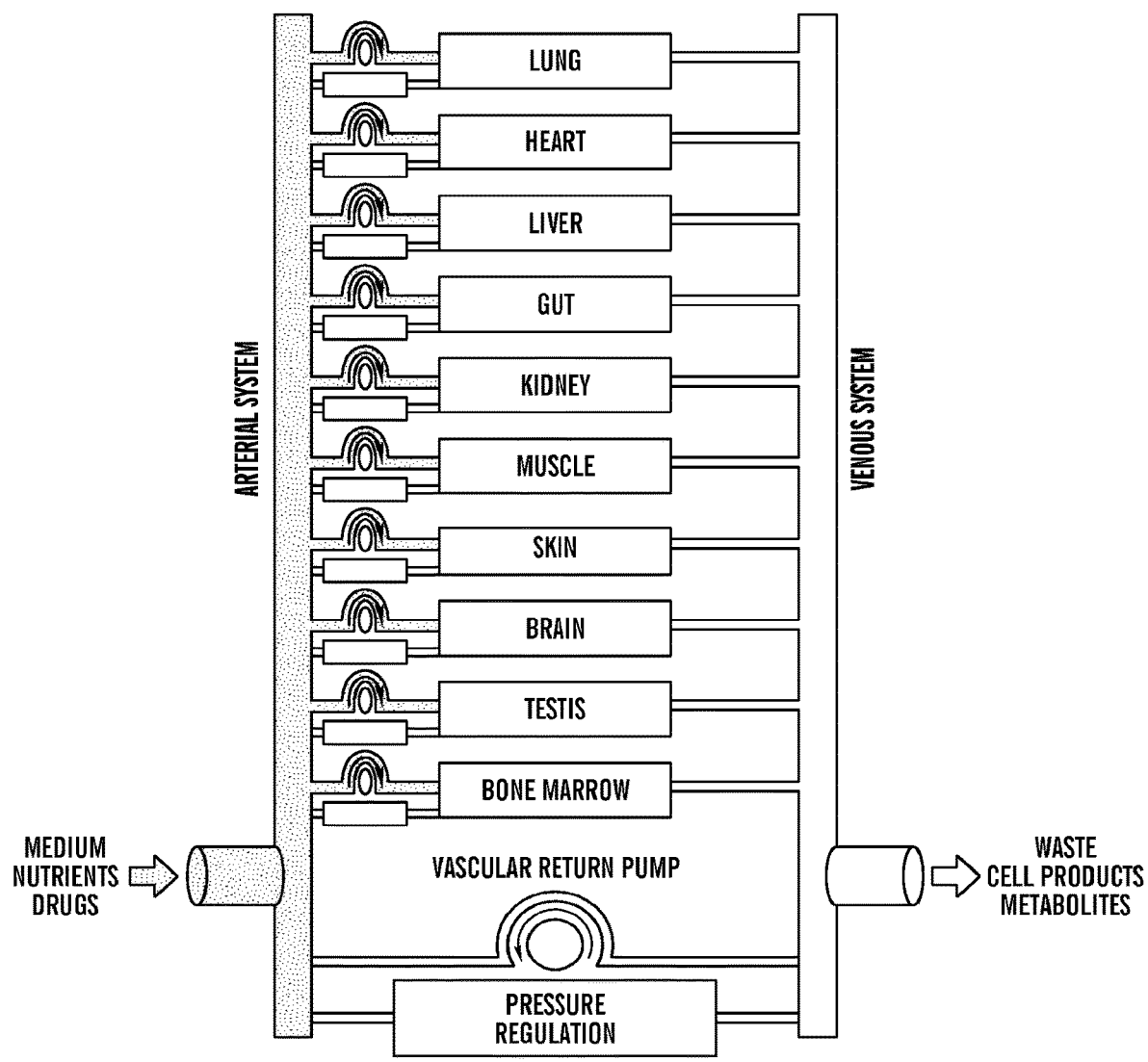
FIG. 17 is a schematic representation of showing interconnection of various Organ Chips according to an embodiment of the Organ Interrogator. As shown, the Interrogator comprises 10 independent Organ Chips that are connected together to create a Microphysiological System.

Without limitations, Organ Chips can be arranged on the Organ Cartridge in any configuration, depending on the designs and/or connections of the fluidic circuits, and/or the port configuration. Without wishing to be bound by a theory, this can allow the Organ Chips to be connected in serial configurations, parallel configurations or any combinations thereof, and/or any recirculation configurations involving one or more Organ Chips. For example, this can allow certain Organ Chips to be in series, e.g. intestine and liver; or right heart, lung, and left heart. Other Organ Chips could be configured to operate in parallel, for example as shown in FIG. 17.

In some embodiments, at least a portion of the fluidic circuit can be detachable from the Organ Cartridge. The detachable fluidic circuit can be pre-attached to the Organ Cartridge and be sterilized as an assembly prior to use.

Any material can be used to construct the Organ Cartridges (or a component thereof) described herein, e.g., depending on the function of each component. By way of example only, the base substrate of the Organ Cartridge can be constructed from any material, e.g., a material that can provide durability, ease of sterilization, minimal risk of contamination, and/or biocompatibility. Such material can be glass, metal, alloy, plastic, polymer, and any combinations thereof.

In some embodiments, the Organ Cartridge can be a Cartridge as described in U.S. Provisional Application No. 61/696,997, filed Sep. 5, 2012, content of which is incorporated herein by reference in its entirety.

In some embodiments, the Organ Cartridges are disposable, or at least one component of the Organ Cartridges is disposable.

In some embodiments, the Organ Cartridge comprises one or more of integrated pumps, valves (e.g. rotary or pneumatic), bubble traps, oxygenators, gas-exchangers (e.g. to remove carbon dioxide), in-line microanalytical functions, and in-line microscopy, e.g., a mini-microscope for in situ monitoring of cells as described in Kim et al., *Lab Chip*. 2012 Oct. 21; 12(20):3976-82, the content of which is incorporated herein by reference in its entirety. Without limitations, using such a Cartridge comprising one or more of the above provides enhanced perfusion control and permits much finer fluidic control and real-time metabolic sensing functions (e.g., $O_2$, pH, glucose, lactate), as well as feedback control capabilities as can be needed to adjust the physical and chemical conditions of the Organ Chip disposed on the Cartridge. In some embodiments, the Organ Cartridge comprise fluidic conduits that are adapted to support the operation of one or more pumps or valves, as would be useful, for example, in the case of rotary peristaltic pumps and valves as described in U.S. Provisional Application No. 61,735,206 titled "Membrane-Based Fluid-Flow Control Devices," filed on Dec. 10, 2012, with pump-heads/valve-heads that can detach from the pump or valves membrane. The content of the above noted U.S. Provisional Application is incorporated herein by reference in its entirety.

In some embodiments, the Organ Cartridge can include automated, sterile valve mechanisms for fluid delivery, sampling and some types of microanalysis on-Cartridge.

In some embodiments, the fluidic circuit can further comprise a fluid control element. Examples of fluid control elements include, without limitations, pumps, pressure transducers, valves, bubble traps, gas exchange membranes, fluid sealing element (e.g., elastomeric O-rings) and sensors (e.g., pH, $O_2$, glucose, lactate, etc.) to ensure proper flow to each Organ Chip. In some embodiments, at least one of the fluid control elements can be in-Cartridge fluid control elements. In some embodiments, at least one of the fluid control elements can be external control elements that are adaptably connected to the Organ Cartridge.

In some embodiments, the Organ Cartridge further comprises at least one sensor or monitor adapted for monitoring or recording a parameter relating to temperature, metabolic activity, health or culture conditions of cells on the at least one organ-chip.

In some embodiment, the sensor or monitor adapted for monitoring comprises at least one electrochemical sensor.

In some embodiments, the organ cartridge comprises at least one valve adapted to selectively connect the sensor or monitor adapted for monitoring with at least one fluidic circuit, e.g., at least one fluidic circuit on the Organ Cartridge.

Figure 30:
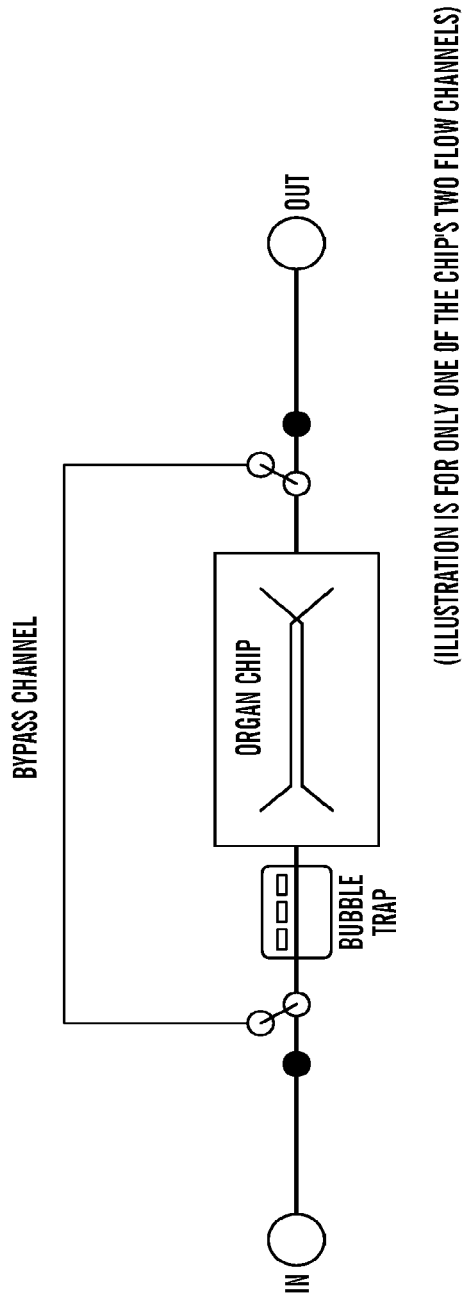
FIG. 30 is a schematic representation of an embodiment of the bypass fluidic circuit in the Organ Cartridge. While the bypass fluidic circuit is shown with reference to an Organ Cartridge, the by-pass fluidic circuit can be implemented in the Organ Cartridge, Cartridge Dock, Organ Farm, or Organ Interrogator. In addition, as shown, the bypass fluidic circuit is only shown for one of the Organ Chip's two flow channels. A similar bypass fluidic circuit can also be used for the second of the Organ Chips' flow channels.

In some embodiments, the Organ Cartridge comprises at least one valve adapted to selectively connect the inlet of the fluidic circuit of the Organ Cartridge with the outlet of the fluidic circuit while disconnecting the connections for the Organ Chip or the port adapted for the Organ Chip positioned or disposed on the Organ Cartridge. This can be useful for clearing any air bubble that can be introduced during connection/disconnection of the Organ Cartridge (e.g., to Organ Chips, other Organ Cartridges, Cartridge Docks, Organ Farm, or Organ Interrogator). In addition, this is also useful for sealing the Organ Cartridge when not connected to Organ Chips, other Organ Cartridges, Cartridge Docks, Organ Farm, or Organ Interrogator. An embodiment of this is depicted in FIG. 30.

In some embodiments, the organ cartridge comprises one of more fluid reservoirs. Without limitations, these reservoirs can hold sensor washing or calibration fluids.

In some embodiments, the fluidic circuit can further comprise a cleaning reservoir. For example, the cleaning reservoir can contain an antiseptic fluid, from which the antiseptic fluid can be pumped to the rest of the fluidic circuit for sterilization purposes.

As show in FIGS. 15A-15E, the fluidic architecture can be implemented using off-the-shelf low-volume valves such as the Nanovolume or Microbore valves from VICI, LabSmith pumps and valves, or the Rheodyne/IDEX manifold system.

In some embodiments, the fluidic circuit/architecture can be implemented using the Cartridges and/or Cartridge Docks described herein which can contain integrated microfluidic perfusion control, valving and in-line microanalytical functions. Without wishing to be bound by a theory, using the Cartridges and/or Cartridge docks can reduce dead volumes, permit finer fluidic control, and/or minimize contamination problems.

The Organ Cartridges comprise at least one fluidic circuit in connection with at least one Organ Chip and/or the corresponding port. In some embodiments, the fluidic circuit can comprise at least two individual flow channels that connect with at least each of the Organ Chips. For example, one of the two individual flow channels can be adapted for an afferent flow (e.g., simulation of arterial flow transport), while the other flow channel can be adapted for an efferent flow (e.g., simulation of venous flow transport). In some embodiments, a multi-way valve can be included, e.g., a 2-way valve, within the fluidic circuit to ensure proper flow direction between the afferent flow and efferent flow channels on the Cartridge Dock.

In some embodiments, the fluidic circuit of the Organ Cartridge can connect to the Organ-Chip using at least one face-sealing raised surface or an O-ring.

In some embodiments, the Organ Cartridge comprises at least one septum in connection with the fluidic circuit for connecting to the fluidic circuit of an Organ Chip, another Organ Cartridge, a Cartridge Dock, an Organ Farm, or an Organ Interrogator.

Figure 18:
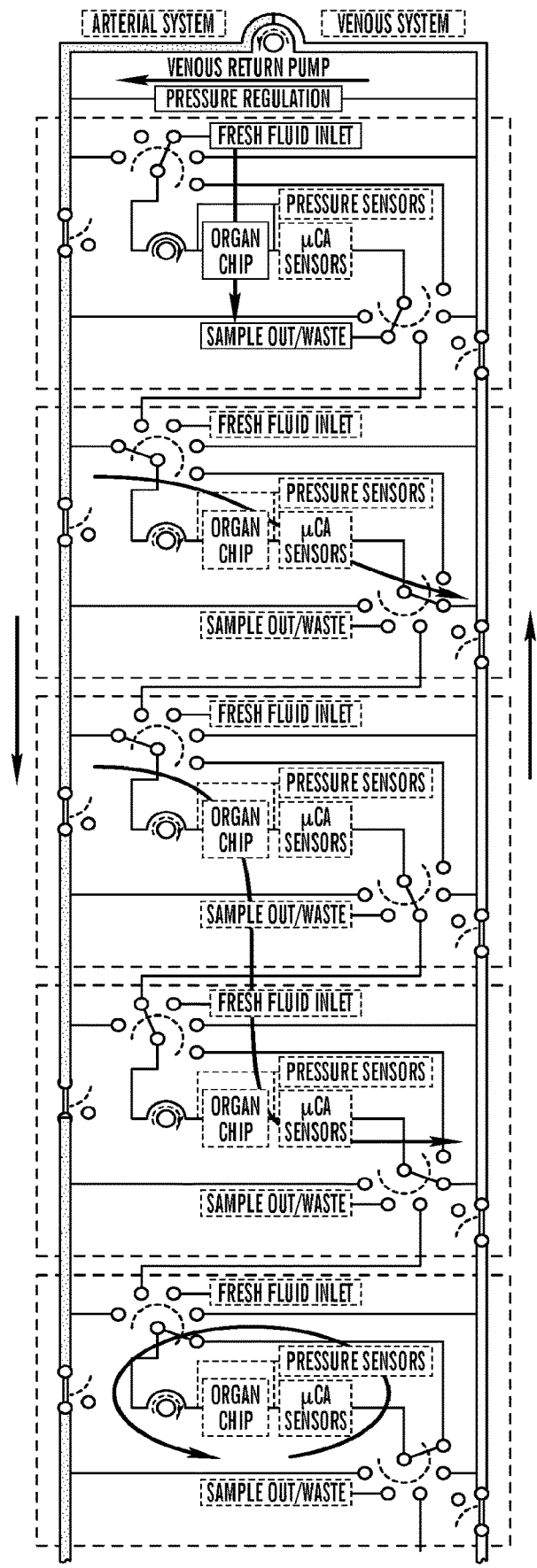
FIG. 18 is a schematic representation of an embodiment showing how fluid can be routed through interconnected Organ Chips using a reconfigurable interconnect system. The Organ Chips can, for example, be perfused using biological media or challenge agent, connected in series or parallel with other Organ Chips, or perfused with recirculating fluid around groups of one or more Organ Chips. Two buses are used, which to a limited extent emulate the in vivo afferent and efferent fluidic system. Fluid can be returned from the efferent bus to the afferent bus either through a specialized conduit (as illustrated) or through one or more Organ Chips (for example, though a Lung-on-Chip). In some embodiment, two or more interconnect systems are used, for example, one for the microvascular pathway and one for the interstitial pathway of the Organ Chips. The interconnect system can be implemented, for example, on the Organ Chip level, on the Organ Cartridge level, as part of a Cartridge Dock, as part of an Organ Farm, and/or as part of an Organ Interrogator. Valves can select the operating mode of the various Organ Chips.

In some embodiments, fluid can be routed through interconnected Organ Cartridges using a reconfigurable interconnects system. The Organ Chips in the Organ Cartridges can, for example, be perfused using biological media or challenge agent. Organ Chips in an Organ Cartridge can be connected in series or parallel with other Organ Chips in the Organ Cartridge. In some embodiments, the Organ Cartridge can be connected in series or parallel with other Organ Cartridges, or Organ Chips perfused with recirculating fluid around groups of one or more Organ Cartridges. Two buses are used, which to a limited extent emulate the in vivo afferent and efferent fluidic system. Fluid can be returned from the efferent bus to the afferent bus either through a specialized conduit or through one or more Organ Cartridges. In some embodiment, two or more interconnect systems can be used, for example, one for the microvascular pathway and one for the interstitial pathway of the Organ Chips disposed on the Organ Cartridge. An exemplary routing of fluids in interconnected Organ Chips is shown in FIG. 18.

In some embodiments, the Organ Cartridge or the fluidic circuit can include at least one multi-way inlet valve that can determine the source of a fluid flow into the inlet of the Organ Cartridge or an inlet of an Organ Chip. In such embodiments, the multi-way inlet valve can be a control inlet valve with at least two ways, at least three ways, at least four ways, at least five ways or more. Examples of inlet fluid sources include, but are not limited to, an upstream Organ Cartridge, an upstream Organ Chip, a supply inlet, the efferent flow channel, the afferent flow channel, a recirculation fluid, and any combinations thereof. The rotary planar valves of FIG. 12C and PCT WO 2012/048261, content of which is incorporated herein by reference, are well suited to accomplish a variety of switching functions, e.g., as illustrated in FIG. 18.

In some embodiments, the Organ Cartridge or the fluidic circuit can include at least one multi-way outlet valve that can direct a fluid flow from the outlet of the Organ Cartridge or an outlet of an Organ Chip to a different outlet destination. In such embodiments, the multi-way outlet valve can be a control outlet valve with at least two ways, at least three ways, at least four ways, at least five ways or more. Examples of the outlet destinations for an outlet fluid can include, without limitation, a downstream Organ Cartridge, a downstream Organ Chip, a fluid-sampling or waste port, the afferent flow channel, the efferent flow channel, a recirculation fluid, and any combinations thereof.

Management of supply and waste fluids allows removal of waste and replenishment of fresh Blood Substitute and drugs using temperature-controlled containers, which can be situated outside of the instrument enclosure, as handled by the Organ Cartridge.

In some embodiments, the Organ Cartridge can provide on-Chip or in-Cartridge perfusion control and microanalytic functions. For example, such a Organ Cartridge can comprise a single integrated unit that holds at least one (e.g., one, two, three, four, five, six, seven, eight, nine, ten or more) Organ Chip and contains Perfusion Controllers and microclinical Analyzers (pCA) (FIGS. 15A-15E), with micropumps, microrotary valves and pCA electrodes, for example, those described in Darby S, Moore M, Wikswo J P, Reiserer R, Friedlander T, Schaffer D K, Seale K T. A Metering Rotary Nanopump for Microfluidic Systems, *Lab on a Chip* 2010, 10: 3218; Velkovsky M, Snider R, Cliffel D E, Wikswo J P. Modeling the Measurements of Cellular Fluxes in Microbioreactor Devices Using Thin Enzyme Electrodes, *Journal of Mathematical Chemistry* 2011, 49: 251; and Eklund S E, Taylor D, Kozlov E, Prokop A, Cliffel D E. A Microphysiometer for Simultaneous Measurement of Changes in Extracellular Glucose, Lactate, Oxygen, and Acidification Rate, *Anal. Chem.* 2004, 76: 519, content of all of which is incorporated herein by reference in their entirety. As a subassembly in the Organ Cartridge, the Perfusion Controller can integrate into the Organ Cartridge a plurality of fluid control elements, such as the microfluidics, valves, membrane oxygenator, gas exchangers to remove excess carbon dioxide, de-bubbler and pumps required to support a single or a plurality of Organ Chips and deliver fluidic samples for either in-Cartridge analysis with the μCA or external analysis by LC/MS or other laboratory techniques.

The valves within the Perfusion Controller can also allow dynamic control of Cartridge-to-Cartridge connections, and allow sterile changes of Cartridge subassemblies. Additionally, Cartridge Docks can support further fluidic routing. By way of example only, the μCA can have at least four components: a disposable, screen-printed electrochemical sensor array that can be in contact with the circulating solutions that perfuse the Organ Chips; a disposable μCA Chip (which provides the microfluidic connections to the sensor array and supports microfluidic valves and a pump); an in-Cartridge μCA valve and pump drive assembly into which the disposable μCA Chip is mounted; and the external μCA Sensor Electronics, which can provide multiplexed sensing of all pCAs in the Organ Interrogator instrument.

As the Perfusion Controller and μCA can both contain customized support microfluidics, pumps, electronics, valving (FIGS. 12 and 13), and instrumentation, they can be configured as appropriate to each individual Organ type. Without wishing to be bound a theory, the integration of the Organ Chips, PC, and μCA into a single plug-and-play unit can offer multiple improved functions including: on-Cartridge sensing of metabolic activity (glucose, lactate, pH, 02 consumption); reduced dead volume from connectors and long lengths of tubing to minimize system response time and perfusion volume and hence increase the sensitivity of the system to limited quantities of metabolites and signaling molecules released or consumed by cells in the Organ Chips; greater ease in sterilization and maintenance of sterility; local control of oxygenation, a finer level of perfusion and metabolic sensing, and the ability to provide feedback control based on the parameters measured in real-time. These functionalities can be important for integration of multiple Organs into a functioning system with long-term stability.

In some embodiments, the Organ Cartridges can be single-use and packaged in a sealed pouch and sterilized. In some further embodiments of this, the single-use Organ Cartridges can be loaded with a least one Organ Chip. Seeding of cell types onto an Organ Chip can be done under sterile conditions within the Organ Cartridge, e.g., when it is plugged into the Cartridge Dock or connected to the Organ Farm. Introduction and extraction of liquids (drug, blood substitute, etc.) during cell culture and testing can be accomplished by needle perforation of a sterile port covered with an elastomeric septum.

Electronic sensing of supply and waste liquids can also be incorporated to inform the operator of run-time capability as well as the need to resupply consumables or remove waste. In FIG. 11, these functions are provided by various system control modules.

In some embodiments, the base substrate can further comprise an electrical connection between the Organ Chips and/or between the Organ Cartridges. (FIG. 11)

In some embodiments, the base substrate can further comprise a pneumatic connection between the Organ Chips and/or between the Organ Cartridges. (FIG. 11)

In some embodiments, the base substrate can further comprise a mechanical connection between the Organ Chips and/or between the Organ Cartridges. (FIG. 11)

In some embodiments, the Organ Cartridges can further comprise at least one microenvironment control unit, e.g., designed to provide an appropriate physiological environment to each Organ Chip. Examples of the microenvironment control units can be designed to control fluid flow (e.g., nutrient, waste, test agent, and/or air, e.g., $CO_2$), temperature, humidity, fluid shear stress, mechanical stimulation, electrical stimulation, and any combinations thereof. In some embodiments, Organ Cartridges can comprise at least one electrical component, e.g., a thermistor.

In some embodiments, a sensing module or technology can be incorporated on an Organ Chip or Cartridge. Front end signal processing including pre-amplification and A/D conversion on-Chip or on-Cartridge can be used to ensure reliable transfer of low-level signals to either the on-board microcontroller or a Master Control Computer.

Figure 14A:
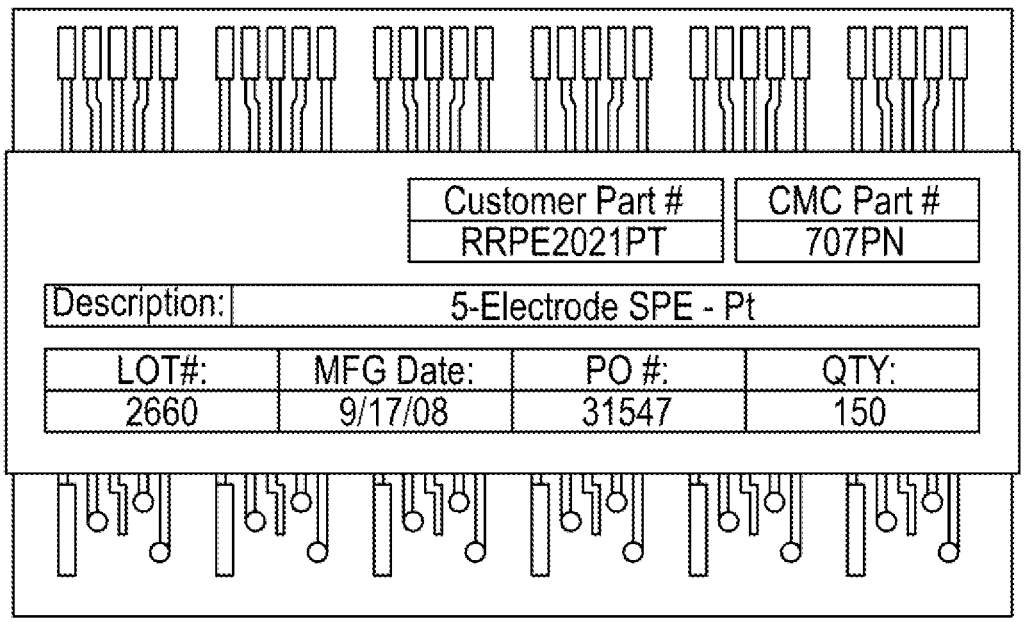
FIG. 14A shows a commercially available Micro-Clinical Analyzer Sensor Array Chip for six chambers with 5 platinum electrodes for Glucose, Oxygen, Lactate, pH sensors, and a counter electrode.
Figure 14B:
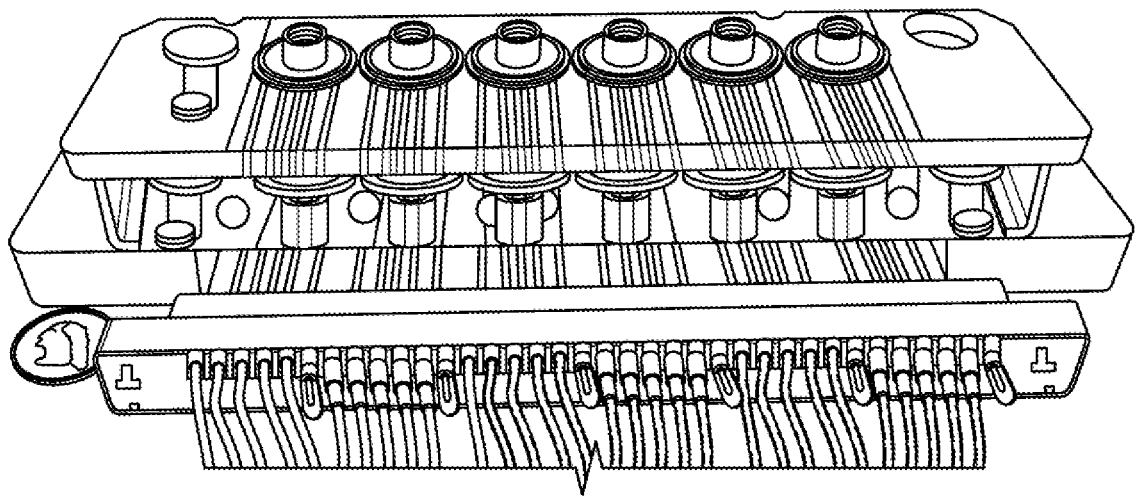
FIG. 14B shows a custom-made microfluidic housing for the Micro-Clinical Analyzer Sensor Array.
Figure 15A:
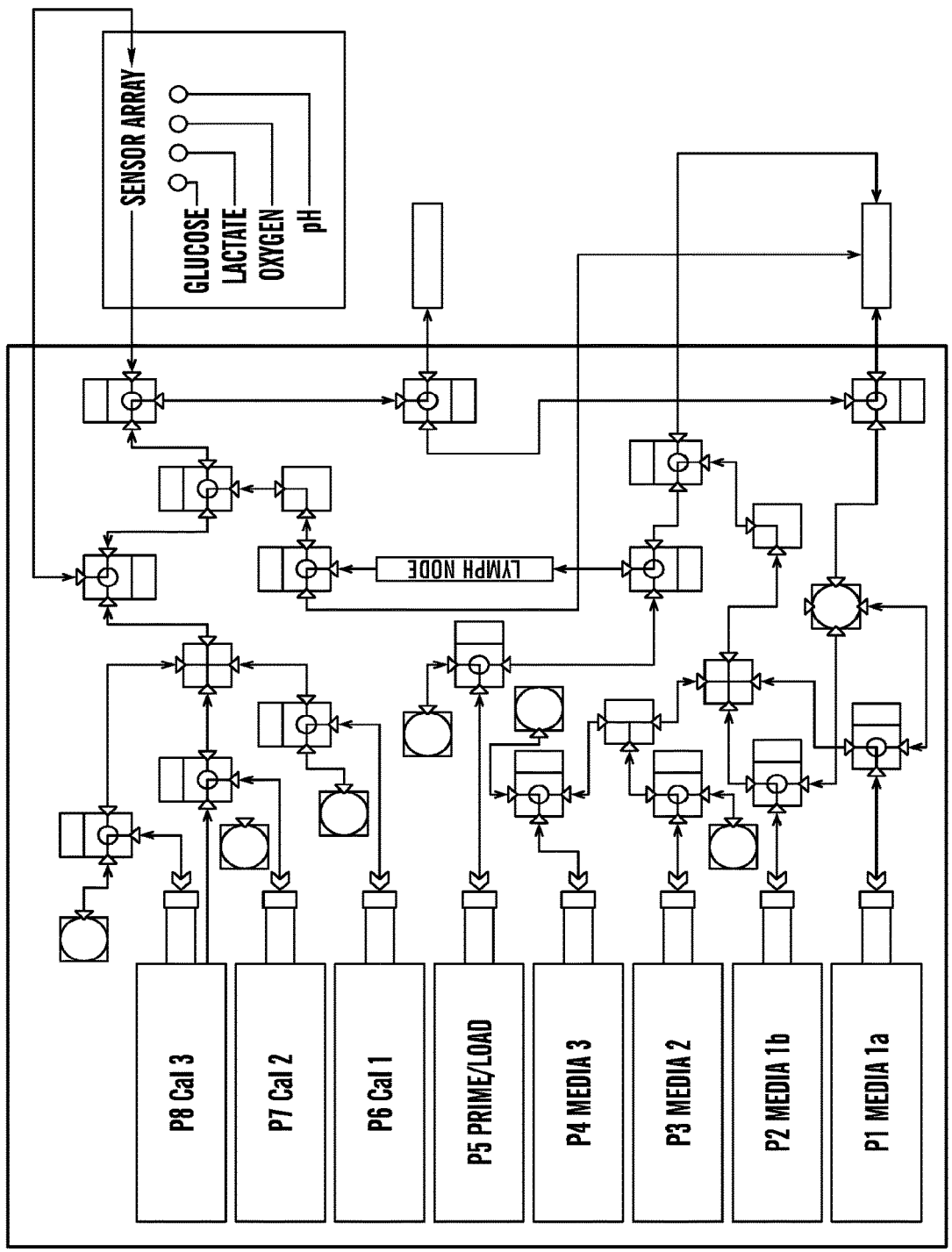
FIGS. 15A-15E show an embodiment of the Organ Cartridge. Included in this design are pumps, valves, and an on-Cartridge Micro-Clinical Analyzer.
Figure 15C:
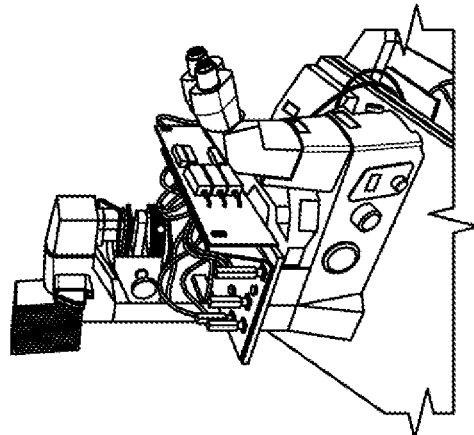
Figure 15E:
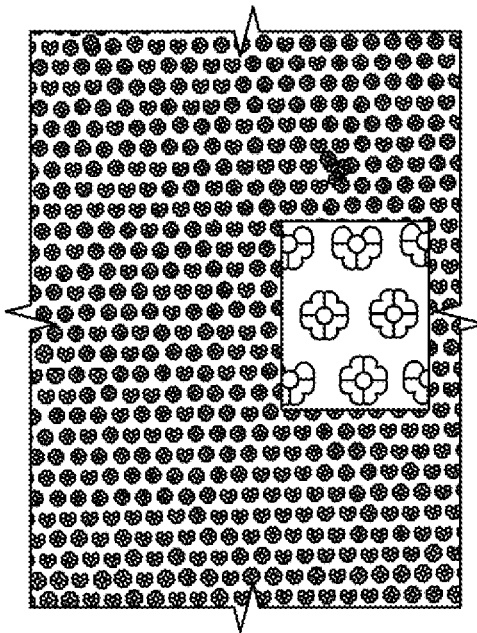
Figure 15B:
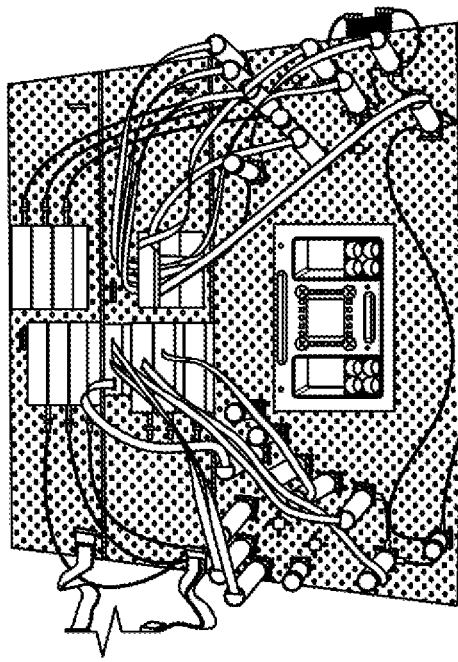
Figure 15D:
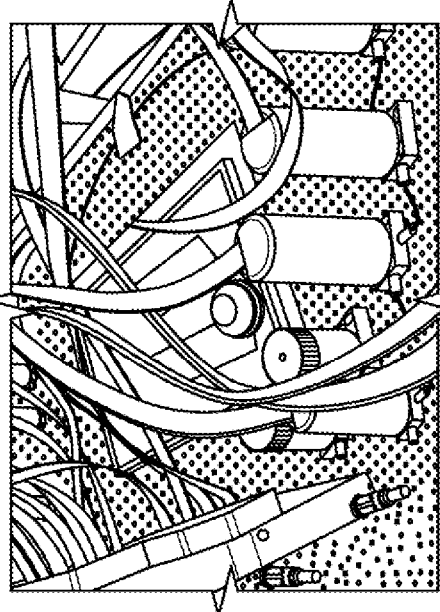
Figure 16E:
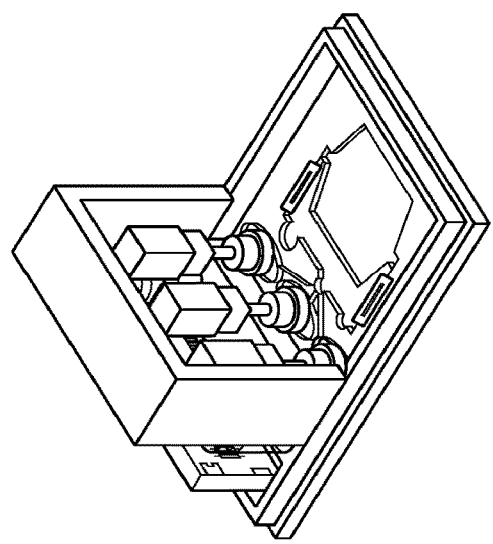
Figure 16D:
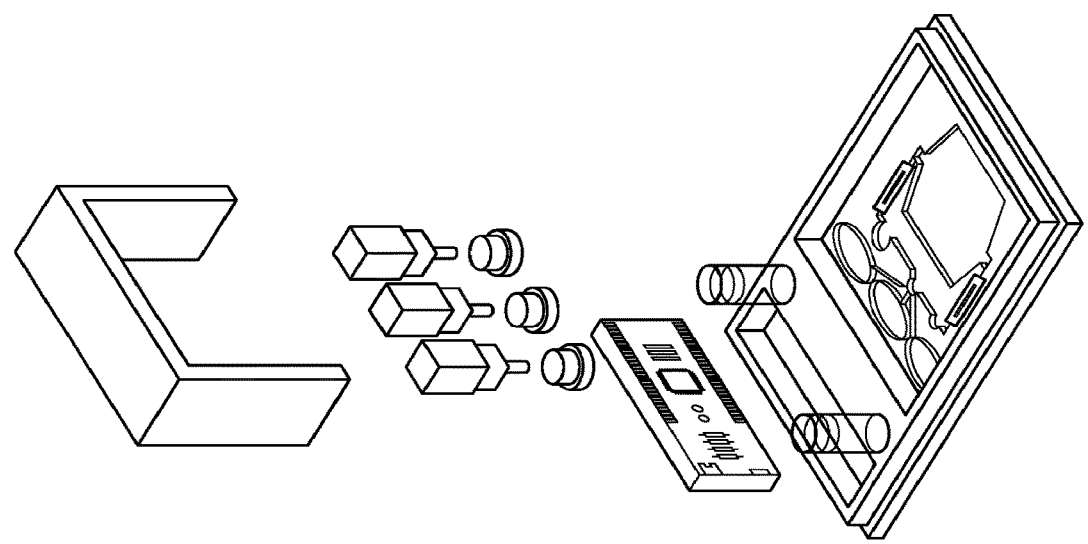

In some embodiments, the Organ Cartridge can further comprise a microclinical analyzer (FIGS. 14 and 15). The micro-clinical analyzer can be in-Cartridge or externally connected to the Organ Cartridge. By way of example only, the micro-clinical analyzer can include an array of sensors (e.g., pH, $O_2$, glucose, lactate, etc.) in contact with a fluid circulating within at least one Organ Chip, one or more pumps and valves, and a fluidic circuit that provides connections to the sensor array and the pumps and/or valves.

In some embodiments, the micro-clinical analyzer can be further connected to an external analytic instrument to perform different kinds of analysis.

In some embodiments, the ports of the fluidic circuit can be covered with an elastomeric septum, e.g., for perforation by a needle when in use to minimize bacterial contamination or water evaporation, as a means to introduce or remove fluid from the circuit.

In some embodiments, the Organ Cartridge can be at least partially enclosed with a moisture- and/or bacteria-impermeable layer to prevent evaporation of water from the Organ Chips and/or contamination of the Organ Chips by bacteria. For example, the moisture- and/or bacteria-impermeable layer can be a BREATHE-EASY™ sealing membrane. BREATHE-EASY™ Sealing Membrane, a disposable, adhesive-backed membrane that is permeable to $O_2$, $CO_2$ and water vapor, can be used to eliminate cross-contamination or microbial infiltration from any ports that need to remain open to air when devices or subassemblies (e.g., Organ Cartridges or Organ Chips) may need to be handled outside of a sterile, laminar flow hood.

In some embodiments, the Organ Cartridge comprises an in-line apparatus or module for imaging. For example, a mini-microscope for in situ monitoring of cells as described in Kim et al., *Lab Chip*. 2012 Oct. 21; 12(20):3976-82, content of which is incorporated herein by reference in its entirety. In some embodiments, the Organ Cartridge can support an external apparatus for imaging. This can include one or more microscopes or other imaging modality adapted to image at least one Organ-Chip. Without limitations, each such microscope can support one or more microscopy modalities, including, for example, brightfield, darkfield, phase-contrast or epifluorescence imaging. In some embodiments, one or more of the microscopes is a Microscope Blade (defined below).

In some embodiments, the Organ Cartridges can be plug-and-play. The term "plug-and-play" as used herein generally refers to the ability of the Organ Cartridges to be plugged into a device or a system (e.g., a Cartridge Dock within an Organ Farm or an Organ-Interrogator, or directly to an Organ Farm or Interrogator), and be readily available for use. In some embodiments, the term "plug-and-play" can also encompass the ability of a computer operating system, e.g., a computer-controlled Cartridge Dock within an Organ Farm or Organ-Interrogator to detect the connection of a new Organ Cartridge or Organ Chip and automatically install the necessary drivers for the operating system to interact with that Organ Cartridge or the Organ Chip disposed thereon.

In some embodiments, the dimensions of the Organ Cartridge can be adjusted for connection and/or use with a Cartridge Dock and/or Organ Farm and/or Organ Interrogator.

In some embodiments where the Organ Cartridge is used with an Organ Farm or an Organ Interrogator, the Organ Cartridge can comprise at least two components—the Cartridge Microfluidics and the Cartridge Drivers (FIGS. 16A-16E). The mechanical design of the Cartridge Drivers is consistent with the designs and specifications of the Farm, Interrogator, Cartridge Dock, Organ Cartridges, and Organ Chips. A particular mechanical design of the Cartridge Drivers can depend on the 3D structure of the instruments and where the Drivers can be physically placed. In some embodiments, the Cartridge Microfluidics are consistent with the Farm and Interrogator fluidic buses, the needs for both parallel perfusion and recirculation of multiple Organs, the serial connection of two Organs, e.g., gut/liver or blood-brain-barrier/brain, and requirements for local recirculation during Organ Chip loading, cell seeding, maintenance, and replacement. Without limitations, the Organ Cartridges can be designed to support one or more of the following functionalities:

- a. The ability to fluidically connect one Organ Cartridge to other such Organ Cartridges, either independently or through the use of a Cartridge-dock which contains similar or different types of Organ structures, for the purpose of simulating and investigating multi-Organ biochemical interactions and responses to drugs, pathogens, and other environmental parameters of physiological relevance.
- b. The ability to monitor and record, via on-Cartridge sensors, certain parameters relating to temperature or metabolic activity that may influence, or be diagnostic of, Organ construct health.
- c. The ability to support optical interrogation of Organ structures via external instrumentation, stand-alone microscopes, or other imaging devices.
- d. The ability to provide stand-alone support for Organ fluid flow under circumstances when the Organ Cartridge is not contained within the Organ incubator 3), for example when the Organ Cartridge is temporarily placed on a stand-alone microscope or being transported between two locations.
- e. The ability to provide regulated thermal control of the Organ construct via on board heaters when the Organ Cartridge in not contained within the Organ incubator 3), for example when the Organ Cartridge is temporarily placed on a stand-alone microscope.
- f. The ability to provide on-board microprocessor controlled variable flow rates of support and/or interrogation fluids to the Organ structure.
- g. The ability to provide measured quantities of specific drugs, chemicals, or biological challenge agents to an Organ structure, via on-board microprocessor control of on-board valves and pumps.
- h. The ability to perform pre-programmed experiment protocols which affect fluid flow, temperature, or the delivery of measured quantities of specific drugs, chemicals or biological challenge agents to the on-board Organ structure.
- i. The ability to wirelessly communicate with any microprocessor contained on the Organ Cartridge for the purpose of
  - i. directing real-time control of pumps and valves
  - ii. downloading of specific experimental protocols to be implemented at a later time
  - iii. directing real-time interrogation of onboard sensors, such as temperature, electrical conductance, or electrochemical devices
  - iv. uploading of log files that detail previously implemented protocols or measurements associated with the on-board Organ construct.
- j. The ability to interface the Organ Cartridge with other instrumentation systems which are capable of providing additional diagnostic, measurement, or control functionality beyond the self-contained features of the Organ Cartridge.
- k. The ability to operate as a self-contained closed loop system which has on-board reservoirs containing required nutrients, pumps which can supply intermittent or continuous perfusion of Organ constructs, and on-board sterile vented waste reservoirs to contain Organ effluent for extended incubation periods.
- l. The ability to trap and dissipate fluid channel air bubbles via use of on-Chip microfluidic bubble traps so that air bubbles of or other gases do not flow downstream and damage Organ construct cells.
- m. The ability to incorporate gas exchange membrane structures into the microfluidic to provide the Organ constructs with appropriate cellular environment.

FIG. 11 shows a schematic representation of an Organ Cartridge (1100) according to an embodiment described herein. As shown, the Cartridges (1100), comprises an Organ Chip (1102) in connection with a module for mechanical control (1104), and two Perfusion Control modules (1106) and two microclinical analyzer (uClinAnalyzer) modules (1108), one for each flow channel of the Organ Chip (1102). Each Perfusion Control module is connected to one channel of the Organ Chip and one uClinAnalyzer module. Also shown are a system control module (1110) in connection with the Cartridge (1100) for controlling the various functions and parameters on the Organ Cartridge, a microscope module (1112), which can be connected to the Cartridge (1100) for monitoring and/or analysis of cells on the Organ Chip (1102); a sample collecting module (1114) in connection with one flow channel of the Organ Chip (1102) and one uClinAnalyzer module (1108); and support systems (1116) comprising modules for flowing fluids (1118) and gases (1120) or recovering waste (1122) from the Organ Chip (1102). In some embodiments, the Organ Cartridge can comprise an optional environmental control module (1124) to control the environment, e.g., temperature, of the Organ Chip (1102).

Some Specific Embodiments of Organ Cartridges

In order for proper function of Organ Chips, they generally require external fluidic interconnections, e.g., with syringe pumps, bubble traps, fluid reservoirs, and valves, which typically require an entire incubator shelf. For example, a minimum of six tubes attached to blunt needles can be required to connect the Organ Chip to these external fluidic infrastructures, which makes handling and removing the device difficult. Additionally, each needle insertion in the Organ Chip can be a point of possible leakage when there is strain on the tube, or a point of failure if the needle becomes clogged when pushed too far into the device.

In order to overcome these challenges, provided herein are Organ Cartridges that interface between Organ Chip(s) and the external fluidic infrastructures in a reliable manner. In some embodiments, the Organ Cartridge is a module that holds one or more Organ Chips and thus allows the Organ Chip(s) to be transferred between instruments using a simple-to-use interface, e.g., to minimize external disturbance to the Organ Chips during the transfer. In some embodiments, the Organ Cartridge can comprise at least one or more fluid-flow control devices, e.g., micropumps, and/or at least one or more analytical systems, e.g., microclinical analyzers, integrated on-board to the Organ Cartridge.

In one embodiment, the Organ Cartridge comprises or integrates at least one (e.g., 1, 2, 3, 4, 5, 6, 7, or more) Organ Chips, at least one (e.g., 1, 2, 3, 4, 5, 6, 7, or more) bubble trap described herein or as incorporated by reference (e.g., a PTFE bubble trap), and at least one (e.g., 1, 2, 3, 4, 5, 6, 7, or more) micropump tubing and septa (e.g., self-healing or self-sealing septa) or functional equivalents thereof (including e.g., quick release Luer Lock fluid input/outputs) in one assembly, where they are all fluidically connected to one another. In some embodiments, the Organ Cartridge can be fluidically connected to an external pumping device (e.g., a peristaltic pump such as a 16-channel peristaltic pump) that is capable of perfusing one or more Organ Chips at once. In some embodiments, the Organ Chips can be configured to be detachable from the Organ Cartridge and work as standalone modules. In some embodiments, the Organ Chips can be built into the Organ Cartridge.

Figure 23:
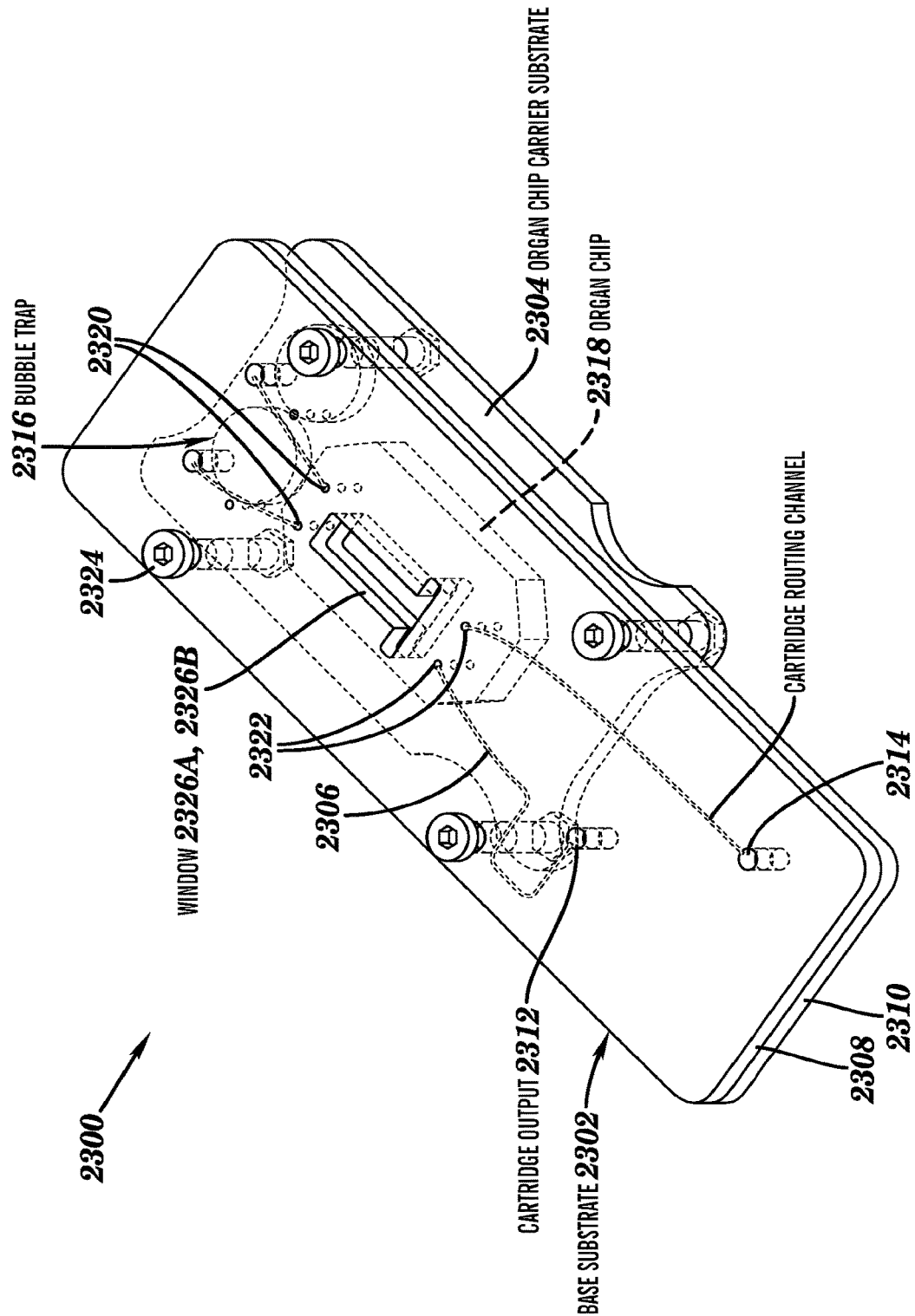
FIG. 23 is a schematic representation showing one embodiment of an Organ Cartridge described herein with an Organ Chip clamped in place.

Referring to FIG. 23, in one embodiment, an Organ Cartridge 2300 can comprise a base substrate 2302 comprising at least one or more fluidic channels 2306 disposed therein and an Organ-Chip carrier substrate 2304 configured to hold at least one or more Organ Chips in place. In one embodiment, the base substrate 2302 can comprise a top substrate 2308 and a bottom substrate 2310 enclosing at least one or more fluidic channels 2306.

Figure 22:
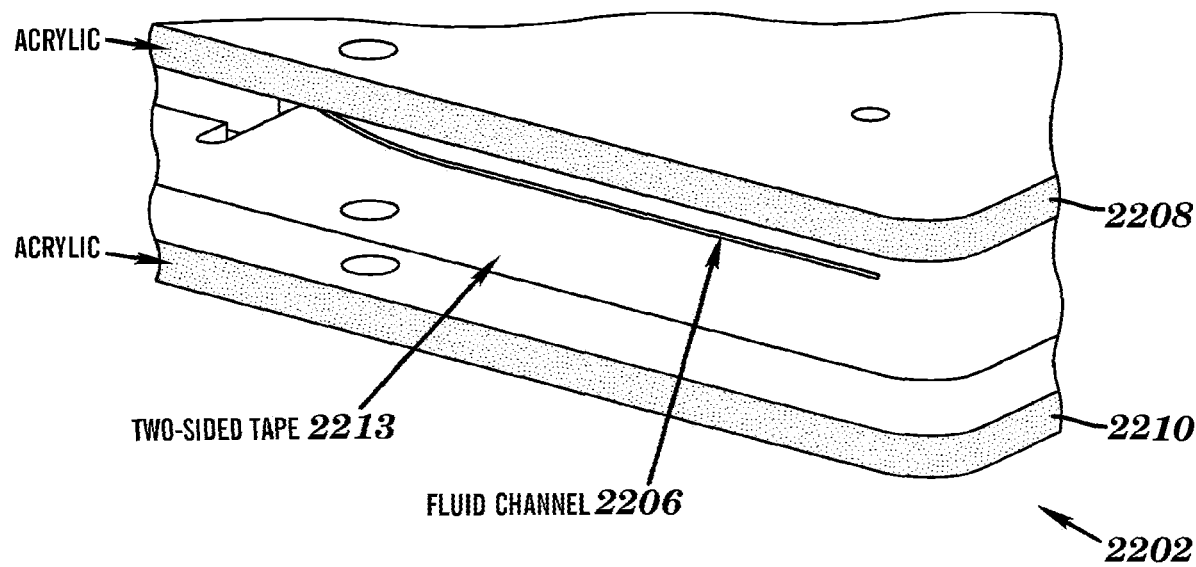
FIG. 22 is a schematic representation of one embodiment of an Organ Cartridge. The Organ Cartridge comprise three layers: two-sided adhesive tape defines the fluid channel side walls and acrylic layers form the top and bottom walls of the channel.

The base substrate 2302 of the Organ Cartridge 2300 can be built by any methods known in the art. For example, in one embodiment, as shown in FIG. 22, the base substrate 2202 (2302) can be built by laser cutting plastic or polymer (e.g., thermosetting plastic or thermoplastic such as acrylic) to form the physical structure or architecture of an Organ Cartridge 2200 (2300), and using double-sided adhesive transfer tape 2213 (e.g., 3M double-sided adhesive transfer tape) to create one or more fluidic channels 2206 (2306). The fluidic channels 2206 (2306) can be cut into the transfer tape 2213, which can be also used to attach top 2208 (2308) and bottom 2210 (2310) substrates (e.g., fabricated from a thermoplastic such as acrylic) together to form a base substrate 2202 (2302) of the Organ Cartridge. The transfer tape 2213 can form the side walls of the fluid channel(s) 2206 (2306) while the top 2208 (2308) and bottom 2210 (2310) substrates (e.g., fabricated from a thermoplastic such as acrylic pieces) can form the top and bottom walls of the fluid channel(s) 2206 (2306).

Depending on the thickness of the transfer tape, the height of the fluid channels 2206 (2306) can vary, e.g., ranging from about 50 μm to about 200 μm. In some embodiments, the height of the fluid channels can be increased, e.g., to reduce pressure requirements of a pump. In one embodiment, the height of the fluid channels 2206 (2306) can be about 150 μm.

Figure 25A:
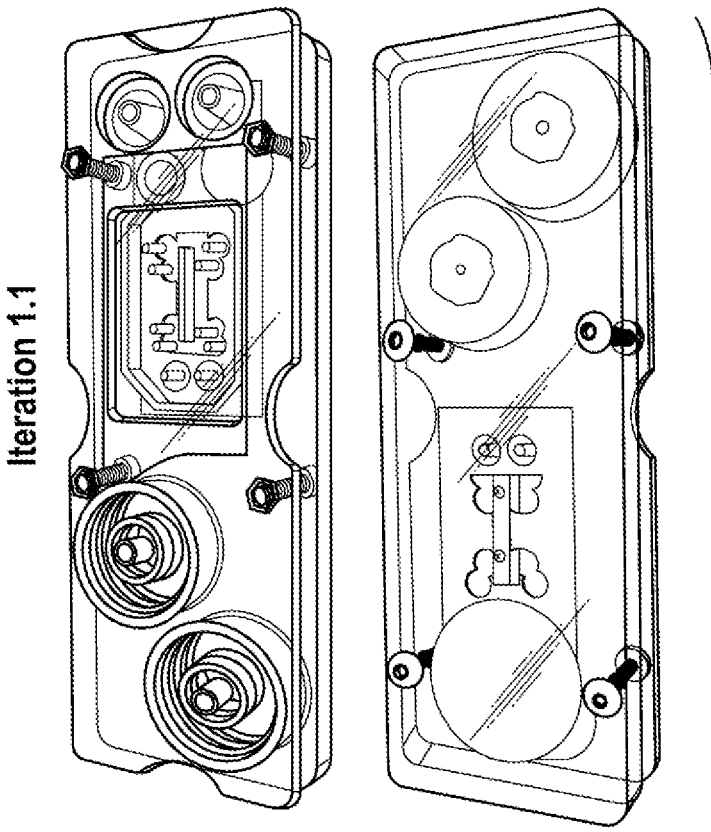
FIG. 25 is a set of photographs showing various embodiments of an Organ Cartridge described herein. Luer Locks were used at the fluidic ports of the Organ Cartridge. The top row shows the bottom perspective view of the Organ Cartridges. The bottom row shows the top perspective view of the Organ Cartridges.
Figure 25A:
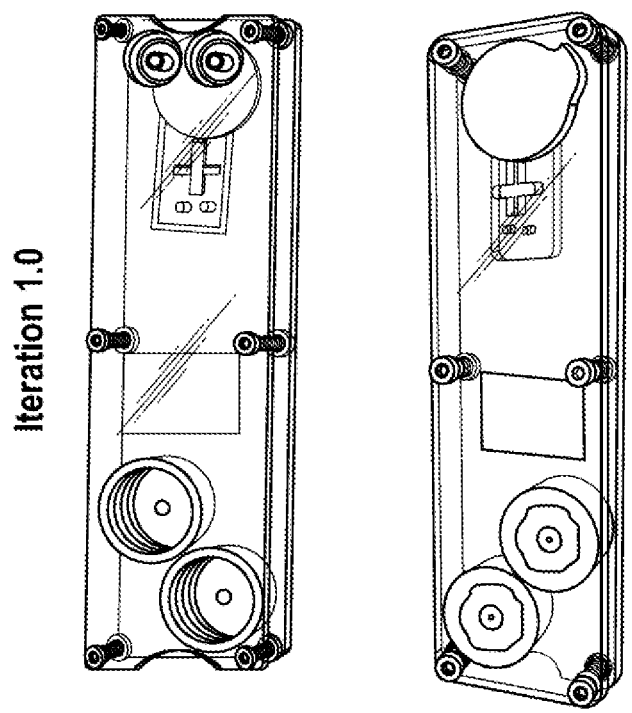
Figure 25B:
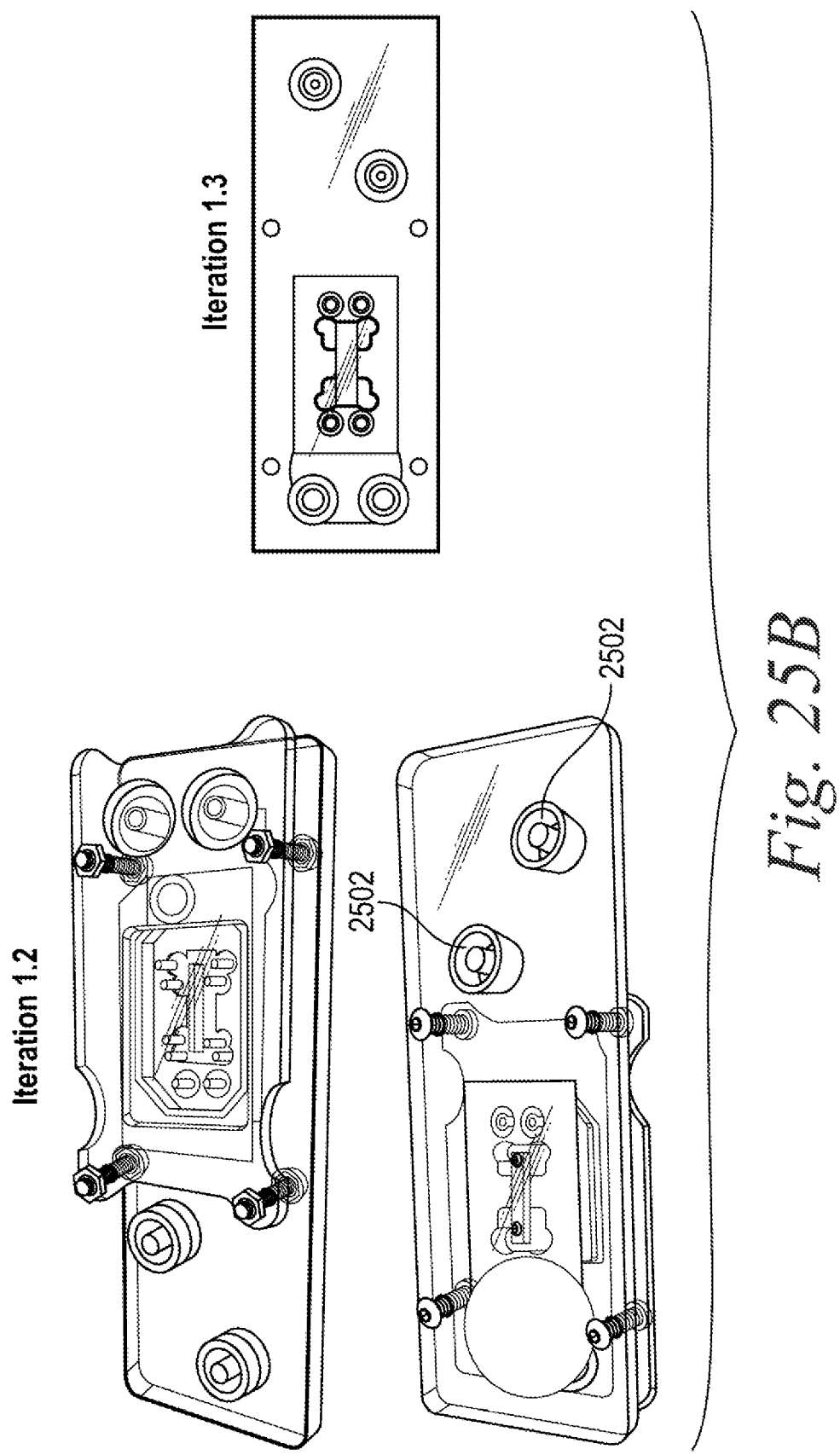
Figure 26A:
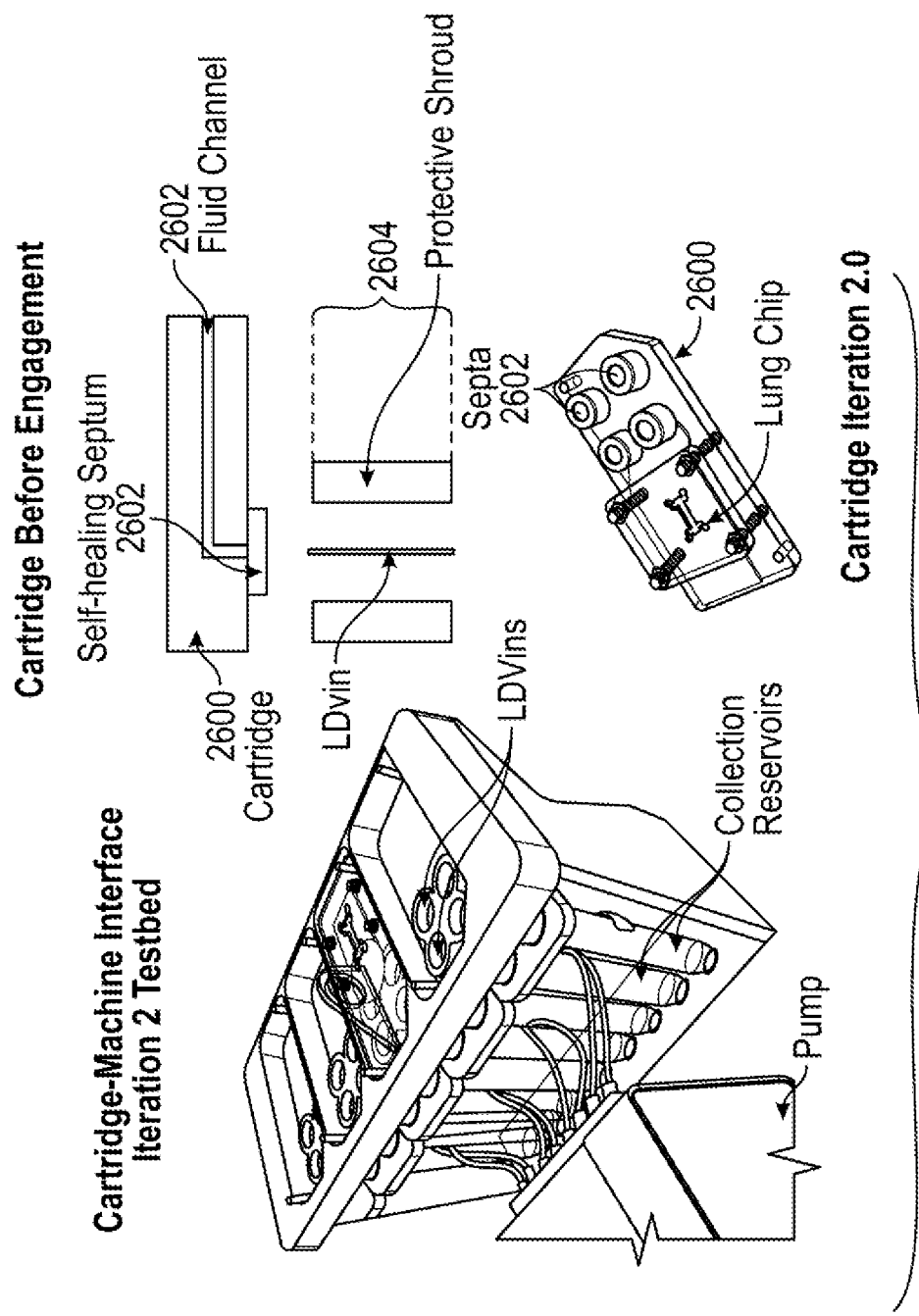
FIG. 26 is a set of images showing other embodiments of an Organ Cartridge described herein. The left image is a photograph showing that a Cartridge Dock can further comprise low dead-volume injection nozzles (LDVin) for Cartridge-machine interface. The top right image is a schematic representation showing an Organ Cartridge with a self-healing septum connected at its fluidic port before engagement with the injection nozzle placed in the Cartridge Dock. The bottom right image is a photograph showing self-healing or self-sealing septa used in place of Luer Locks as shown in FIG. 25. Such embodiments provide plug-and-play functionality.
Figure 26B:
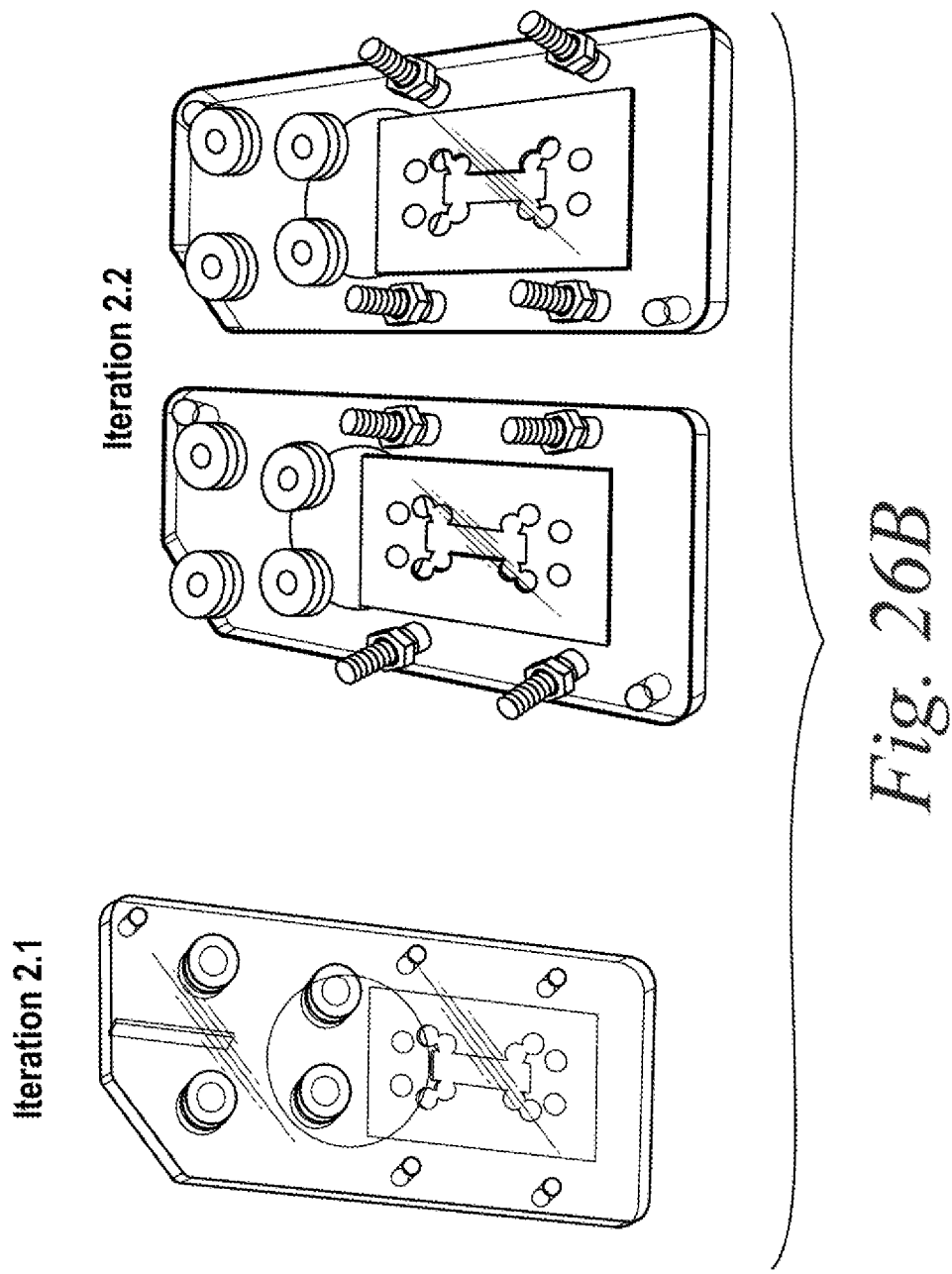

Either one or both of the top 2208 (2308) and bottom 2210 (2310) substrates comprise at least one or more (e.g., at least two, at least three, at least four, least five or more) fluidic ports (e.g., 2312, 2314 as shown in FIG. 23). The fluidic ports 2312, 2314 can be adapted to provide one or more fluidic connections. For example, a fluid connector such as Luer-type connectors (e.g., quick-connect/disconnect Luer Locks 2502 as shown in FIG. 25) or septum-type connectors (e.g., (e.g., self-healing or self-sealing septa 2602 as shown in FIG. 26) can be connected to appropriate fluidic ports, e.g., 2312, e.g., for external fluidic connections, e.g., connection to the tubing from a pumping device (e.g., a peristaltic pump), or to drip into waste containers. When the Organ Cartridge is transferred from one place to another place, e.g., removed from one Cartridge Dock or from an incubator, to another Cartridge Dock or to another system such as analytical system, e.g., for imaging, the tubing connected to the Organ Cartridge can be easily disconnected and fluidically and/or sterilely sealed at the corresponding fluidic ports (e.g., 2312, 2314) with a Luer or septum cap.

Figure 27:
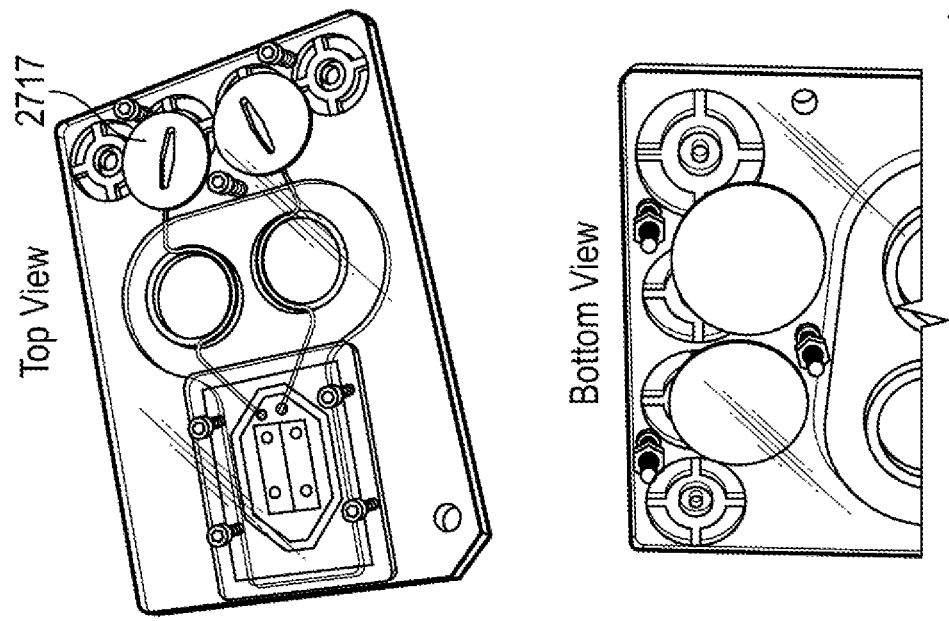
FIG. 27 is a set of photographs showing different perspective views of one embodiment of an Organ Cartridge as well as one Organ Cartridge placed in an exemplary Cartridge Dock described herein. These embodiments comprise a microfluidic component for fluid routing and provide a microfluidic channel that can accept a rotary peristaltic pump's pump-head.
Figure 27:
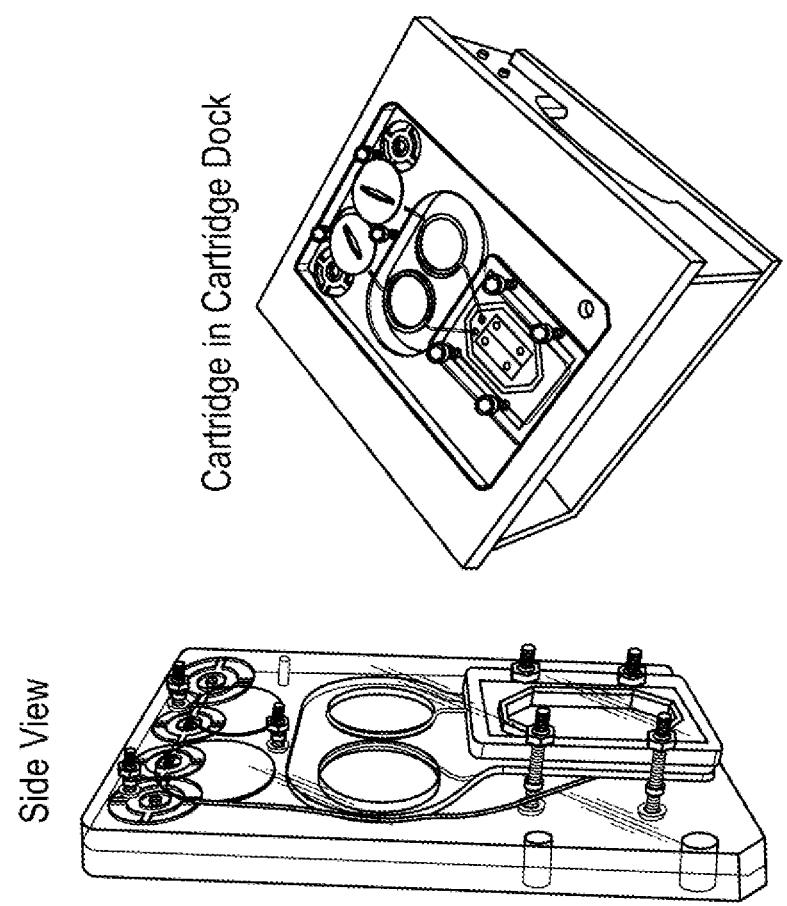

In some embodiments, the base substrate 2302 of the Organ Cartridge can comprise at least one bubble trap described herein or as incorporated by reference (e.g., 2316) fluidically connected into an Organ Chip 2318, as shown in FIG. 23. In some embodiments, a bubble trap 2302 can be integrated into the base substrate 2202 (2302), for example, by placing a gas permeable membrane 2717 (as shown in FIG. 27) between the top substrate 2208 (2308) and the adhesive layer 2213. The input connectors e.g., Luer Locks and/or septa can connect to fluidic channels in the Organ Cartridge that can lead through a bubble trap 2302 and into the Organ Chip input channels and inlets 2320. The output or outlets 2322 of the Organ Chip 2318 can feed into a separate fluid channel, e.g., 2306, in the Organ Cartridge that routes the fluid into one or more outlets 2312, 2314, e.g., adapted to connected to output connectors, e.g., Luer Locks and/or septa.

Depending on the design of an Organ Cartridge, the Organ Chip(s) can be placed and/or secured in the Organ Cartridge accordingly, provided that the placement of the Organ Chips permits fluidic connection to intended components for proper function and/or monitoring cells cultured in the Organ Chips. For example, as shown in FIG. 23, in one embodiment, the Organ Chip 2318 can be fixed to an Organ Cartridge 2300 by attaching to the base substrate 2302 another layer of substrate as an Organ-Chip carrier substrate 2304 (e.g., fabricated from a thermoplastic such as acrylic) that is configured to secure and/or clamp the Organ Chip in place. The Organ-Chip carrier substrate 2304 can be attached to the bottom surface of the base substrate 2302 by any means, e.g., using screws or clamps 2324, to mechanically connect the two layers together with one or more Organ Chips placed in-between.

While FIG. 23 illustrate one Organ Chip 2318 placed in the Organ-Chip carrier substrate 2304, the Organ-Chip carrier substrate 2304 can be adapted to provide a capacity to hold at least one or more Organ Chips 2318 (e.g., 1, 2, 3, 4, 5, or more Organ Chips), e.g., by increasing the dimensions of the Organ Cartridge.

In some embodiments, the mating surface of the Organ Cartridge can have elevated ridges around the fluidic ports that connect to the Organ Chip. This can concentrate the pressure near the fluidic connection, and reduce any chance of leakage. These pressure concentrators can be made, e.g., by selectively laser rastering the Organ Cartridge's mating surface everywhere except for the elevated ridge region.

In some embodiments, the Organ-Chip carrier substrate 2304 can comprise a window 2326A that is cut out around the area where the Organ Chip 2318 is intended to be imaged. This can, e.g., prevent an increase in or reduce the amount of material any optics has to image through.

In some embodiments, the base substrate 2302 (top 2308 and bottom 2310 substrates) of the Organ Cartridge can comprise a window 2326B that is cut out above the functional area of the Organ Chip 2318, e.g., to allow oxygen to oxygen diffusion through the Organ Chip to the cell layer. Additionally or alternatively, the window 2326B in the base substrate 2302 can be placed in aligned with the placement of the window 2326A that is cut out in the Organ-Chip carrier substrate 2304 for visualization and/or imaging of the area of the Organ Chip where is intended to be imaged.

The dimensions and/or design of the window 2326A, 2326B in the base substrate 2302 and Organ-Chip carrier substrate 2304 of the Organ Cartridge 2300 can vary in accordance with needs, e.g., imaging size and/or cell culture region of the Organ Chips. While FIG. 23 illustrates a rectangular-like window 2326A, 2326B cut in the Organ Cartridge, other shapes and/or arrangement of window can also be used in the design of the Organ Cartridge. For example, the window can be in a shape of a square, circle, oval, diamond, polygon, and/or any irregular shape. In some embodiments, the window can be an array of smaller windows, e.g., with a size that permits imaging of a smaller population of cells, e.g., a few cells. In such embodiments, same population of cells or individual cells can be imaged over time through the same smaller windows.

Cartridge-Dock

Figure 19:
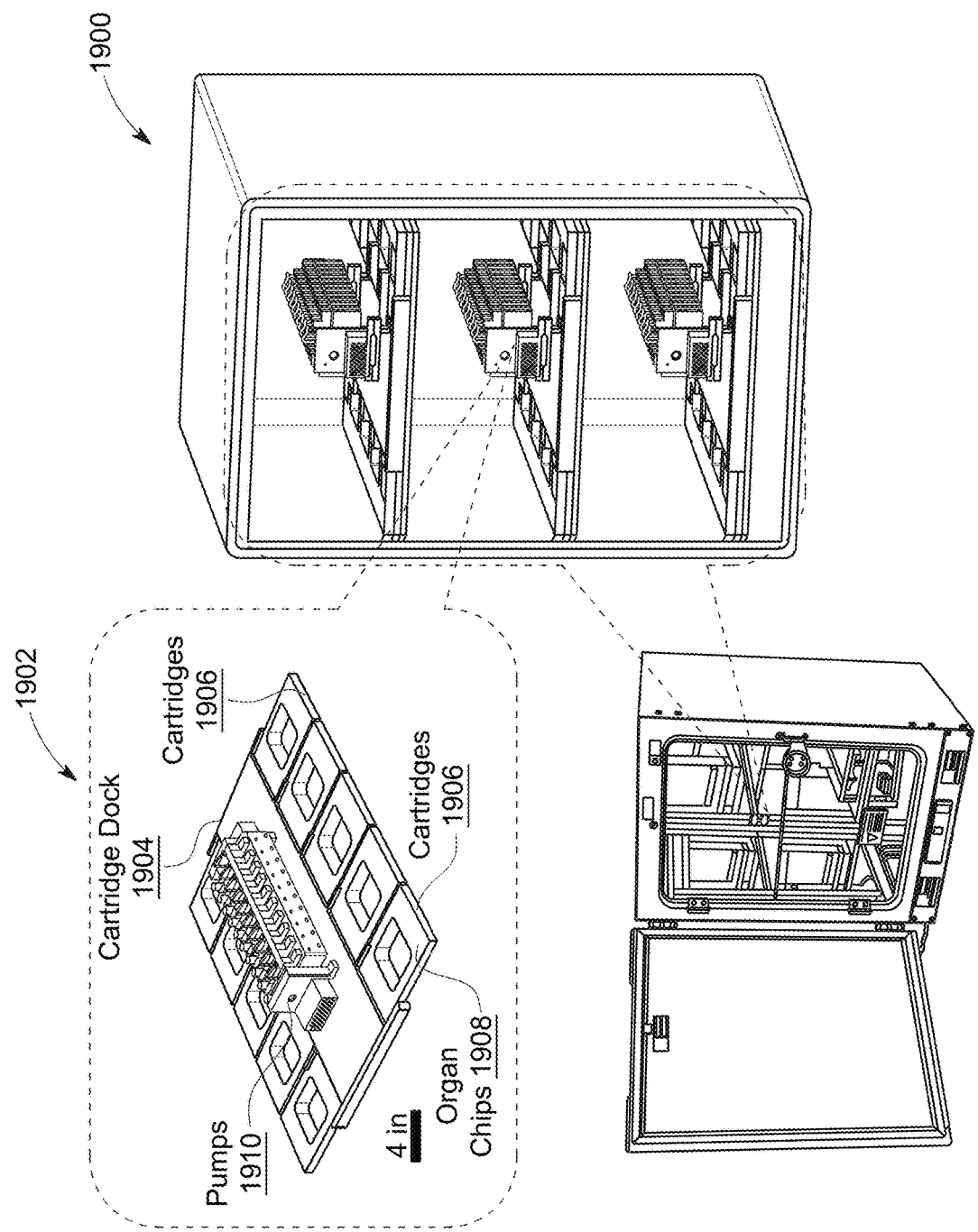
FIG. 19 shows an embodiment of the Organ Farm. Three Organ Cartridges are shown placed within the Organ Farm for initial establishment of a cell culture within the Organ Chips.

While an Organ Cartridge can be connected directly with an Organ Farm and/or Organ-Interrogator directly, a Cartridge Dock can also be used to connect the Organ Cartridge with an Organ Farm and/or Organ-Interrogator. Generally, the Cartridge Dock is a component of the Organ Farm or the Organ Interrogator. The Cartridge Dock can provide fluid, gas and/or electrical connections between the Organ Cartridge and Organ Farm and/or Organ-Interrogator. In addition, the Cartridge Dock can also provide fluid, gas and/or electrical connections between the Organ Cartridge and the control and analytical instrumentation as shown in FIGS. 17-19. Thus, the Cartridge Dock can provide fluid, gas and electrical connections between the Cartridges holding the Organ Chips and the control and analytical instrumentation (FIG. 18).

Alternatively, the Organ Dock can be just a stand for holding the various components, e.g., Organ Cartridges, reservoirs, etc. In such embodiments, the Organ Farm or the Organ Interrogator can provide fluid, gas and electrical connections between the Cartridges holding the Organ Chips and the control and analytical instrumentation.

Without limitations, a Cartridge Dock can be designed to hold any number of Organ Cartridges. For example, a Cartridge Dock can be configured to hold one or more (e.g., one, two, three, four, five, six, seven, eight, nine, ten or more) Organ Cartridges.

Generally, the Cartridge Dock comprises one or more fluidic circuits. The fluidic circuit can be connected to the Cartridge Dock for flowing nutrients, media etc. through the Cartridge Dock or a Cartridge attached to the Cartridge Dock. Without wishing to be bound by a theory, fluidic control of individual Organ Chips within the Cartridge Dock permits use of Organ-specific culture medium to ensure optimal pre-conditioning of the Organ Chips before they are transferred to the Interrogator, where a common medium or Blood Substitute can be utilized. In some embodiments, the Cartridge Dock further comprises a control system for microfluidic handling.

In some embodiments, to ensure sterility, the interface of the Cartridge Dock can be designed with attention to materials of construction and sealing elements, such as elastomeric SEPTA, O-rings, surface finishes, and machine function.

The Cartridge Dock can connect microfluidically, mechanically and/or electrically to common ports on the Cartridge. A Cartridge Dock within an Organ Farm is also referred to as a "Farm module" herein. A Cartridge Dock can be manufactured to connect with any required number of Organ-specific Cartridges. Accordingly, one or more Organ-specific Cartridges can be connected in each Farm culture module. In some embodiments, one or more (e.g., one, two, three, four, five, six, seven, eight, nine, ten, eleven, twelve, thirteen, fourteen, fifteen or more) Organ-specific Cartridges can be connected in each Farm culture module. In one embodiment ten or more Organ-specific Cartridges can be connected in each Farm culture module (FIG. 19). As described herein, each Farm culture module comprises the fluidic circuits and fits the size constraints of standard incubator shelf dimensions; thereby allowing convenient handling of the Cartridges.

In some embodiments, the Cartridge Dock can further comprise a temperature control unit, e.g., as shown in FIG. 11. For example, a temperature control unit can comprise at least thermistor, which can be used to monitor temperature at one or more locations. Additionally, the temperature control unit can comprise a heating element that can be used, e.g., alone or in combination with the thermistors, to maintain temperature of the Organ Chips at 37±0.5° C. or at any other desired temperature.

In some embodiments, the Cartridge Dock can comprise at least one pump and/or pressure sensor for each Organ Chip to modulate an optimum flow specific for the Organ Chip. In some embodiments, systemic venous return pumps with pressure sensors can be used to maintain the desired arterial-venous pressure difference for varying Organ loads. Management of supply and waste fluids can allow removal of waste and replenishment of fresh Blood Substitute and drugs using temperature-controlled containers situated outside of the instrument enclosure. Electronic sensing of supply and waste liquids can also be incorporated to inform the operator of run-time capability as well as the need to resupply consumables or remove waste. It is to be understood that when the Cartridge Dock is acting as just a holder of components, the pump and/or pressure sensor for each Organ Chip to modulate an optimum flow specific for the Organ Chip can be provided by the Organ Farm or the Organ Interrogator.

In some embodiments, the cells can be monitored by using electrochemical sensors to measure the metabolic activity of the cells through changes in pH and the concentration of glucose, lactate, oxygen and other substances as the perfusing media passes over the cells in the Organ Chip.

In some embodiments, the Cartridge Dock can control pressure regulation to balance mismatches between different Organ Chips based on variations in size or design using in-line pumps and rotary or pneumatic valves before or after each Organ, e.g., Organ Chip. Systemic venous return pumps with pressure sensors can maintain the desired arterial-venous pressure difference for varying Organ loads.

Generally, a Cartridge Dock can be configured to allow multiple modes of operation: 1) incubation and pretreatment, allowing one or multiple Organ Chips to be perfused independently with fresh media, blood, Blood Substitute or drug; 2) recirculation through individual Organs (e.g., for pre-activation of Liver enzymes); 3) recirculation of media, blood, or Blood Substitute through two or more, e.g., up to ten, Organs in parallel, to mimic the Organ-Organ physiological coupling in animal or clinical studies; and 4) daisy chaining (connection in series) of one or more Organ Chips to allow the outflow of one Organ Chip to feed directly into another (e.g., Gut-Liver axis interactions) (FIG. 18). A similar level of control and sampling for liquids (and air) flowing through the Interstitial Channels can also be provided in the Interrogator device.

In some embodiments, the Cartridge Dock comprise can comprise one or more separate fluidic bus systems. Fluidic bus system is described in detailed herein below. In some embodiments, the Cartridge Dock can comprise at least two separate fluidic bus systems, for example, corresponding to the Arterial and Venous systems that can connect to either the Microvascular or Interstitial Channels in each Organ Chip (FIGS. 17 & 18). The Arterial system can be involved in the transport of nutrients, fluid medium and/or test agents such as drugs to at least one Organ Chip. The Venous system can be involved in the transport of waste, cell products and metabolites away from at least one Organ Chip.

In some embodiments, fluid can be routed through interconnected Cartridge Docks using a reconfigurable interconnects system. The Organ Chips in the Cartridge Docks can, for example, be perfused using biological media or challenge agent. Organ Chips in a Cartridge Dock can be connected in series or parallel with other Organ Chips in the Cartridge Dock. In some embodiments, the Cartridge Dock can be connected in series or parallel with other Cartridge Docks, or Organ Chips perfused with recirculating fluid around groups of one or more Cartridge Docks. Two buses are used, which to a limited extent emulate the in vivo afferent and efferent fluidic system. Fluid can be returned from the efferent bus to the afferent bus either through a specialized conduit or through one or more Cartridge Docks. In some embodiment, two or more interconnect systems can be used, for example, one for the microvascular pathway and one for the interstitial pathway of the Organ Chips disposed on the Cartridge Dock.

In some embodiments, the fluidics system utilizes peristaltic pumps or vibrating diaphragm or other pumps fitted with pressure transducers to deliver liquids to the Cartridge Dock. The Cartridge Dock, in turn, can feature two parallel fluidic bus systems, corresponding to the Arterial and Venous systems that connect to either the Microvascular or Interstitial Channels in each Organ Chip (FIGS. 17 & 18). The two bus systems (for each Channel) can deliver liquids, gases and aerosols to the Cartridges for perfusion and recirculation in single or multiple Organs. Additional connections between Cartridges in a Cartridge-dock can allow for recirculation within one Cartridge or between Cartridges.

In some embodiments, the Cartridge Dock provides for initial loading of cells into pre-sterilized Organ Chips held within individual Cartridges.

In some embodiments, the cyclic vacuum in the control channels can be modulated by pressure regulators in conjunction with electronically operated flow valves. The pressure in various channels can be monitored by electronic or microfabricated optical pressure transducers. In some embodiments the system is controlled by a dedicated modular microprocessor instrumentation control module within the electronic system architecture, in conjunction with a vacuum pump.

In some embodiments, one or more sensing modules or technologies can be incorporated in the Cartridge Dock (i.e., external to the Cartridge and Organ Chip).

In some embodiments, the Cartridge Dock can further comprise at least one sensor for control of environmental conditions (e.g., temperature, humidity, pH, nutrient, waste, and/or shear stress), appropriate delivery of fluids and/or control of vacuum. Sensors for detection of different environmental conditions, fluid flow and pressure are known to a skilled artisan.

In some embodiments, the Cartridge Dock can include one or more microscopes or other imaging modality adapted to image at least one Organ Chip. Each such microscope can support one or more microscopy modalities, including, for example, brightfield, darkfield, phase-contrast or epifluorescence imaging. In some embodiments, one or more of the microscopes is a Microscope Blade (defined below).

Depending on various target applications, e.g., for use as a disease model or for pharmacokinetics study of a drug, different combinations of Organ Chips can be selected within the Cartridge Dock. For example, in one embodiment, Lung Chips, Heart Chips and Liver Chips can be selected to be disposed on the Organ Cartridges because, without wishing to be bound by theory, they provide functionalities that are most critical for determination of clinically relevant pharmacokinetics (PK)/pharmacodynamics (PD) as well as efficacy and cardiotoxicity (which is the cause of more than 30% of all drug failures).

Without limitations, the Cartridges Dock can be designed to support one or more of the following functionalities:

a. Inter-Organ connectivity and flow control.
b. Systemic delivery of drugs, chemicals, or biological challenge agents to interconnected Organ modules.
c. Direct monitoring of atrial or venous fluid flows.
d. Removal of waste from Organ Chips.
e. Recirculating fluid within the Cartridge Dock, between two or more Organ Cartridges.
f. On demand sampling of fluids from individual Organ modules for external instruments, such as a mass-spectrometer or chromatography system.
g. Detailed time course monitoring of Organ effluent characteristics.
h. An on-board monitoring system including alarms to notify the user if intervention is required.
i. Systemic inter-Organ flow profile protocol controls.
j. Implementation of sensor driven feedback mechanisms to maintain inter-Organ homeostatic systemic behavior.
k. Coordination of all functional aspects of each Organ Cartridge.
l. Compilation and documentation of detailed multi-Organ experiment measurement and control parameters.

Some Specific Embodiments of the Cartridge Dock

Figure 24A:
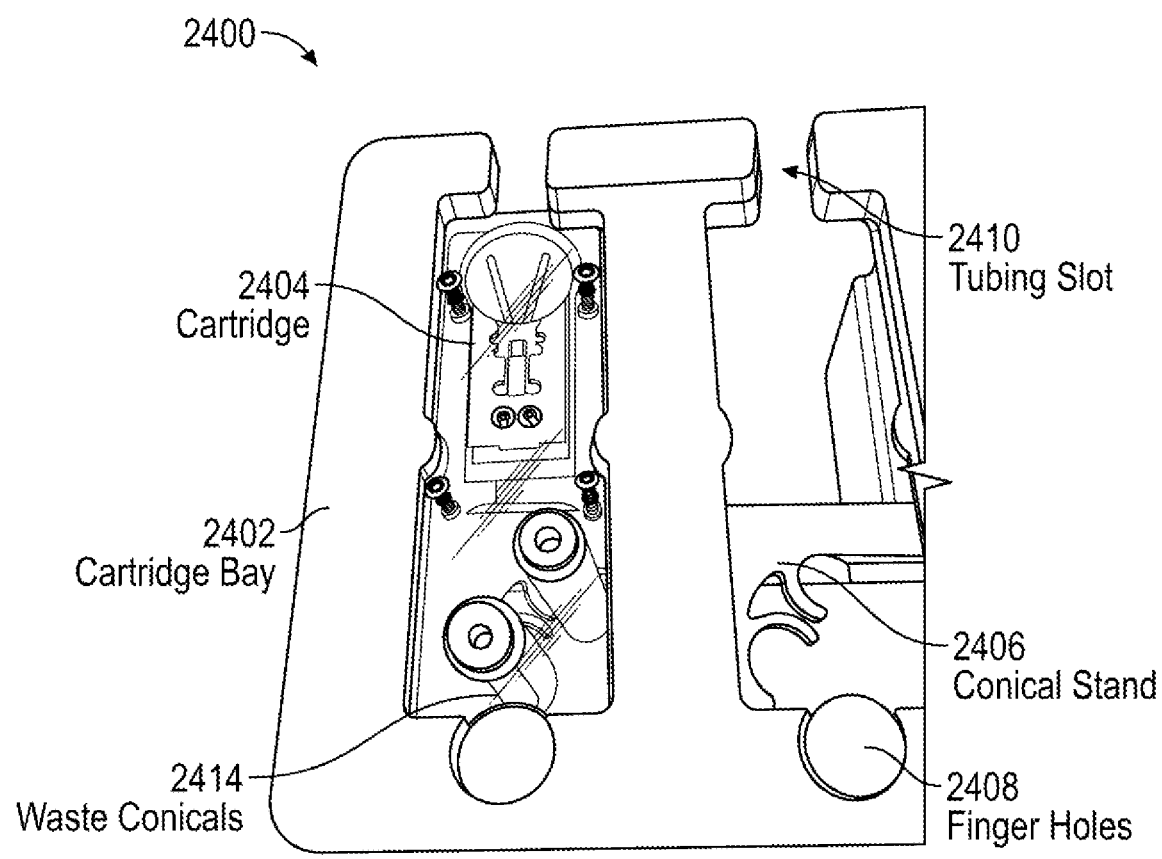
FIGS. 24A-24B are photographs showing exemplary embodiments of a Cartridge Dock described herein.

FIG. 24A shows a picture of a portion of a Cartridge Dock 2400 according to an embodiment of described herein, in which the Cartridge Dock 2400 can comprise two Cartridge bays 2402 with one bay engaged with an Organ Cartridge 2404. The Cartridge bay 2402 can hold the Cartridge assemblies near the peristaltic pump.

In some embodiments, a Cartridge Dock 2400 can comprise at least one or more two Cartridge bays 2402 (e.g., 1, 2, 3, 4, 5, 6, 7, 8, 9, 10 or more bays) for placement of Organ Cartridges 2404.

In some embodiments, the Cartridge Dock 2400 can comprise finger slots 2408, e.g., on the end(s) and/or side(s) of the Organ Cartridge slots 2402 so that an Organ Cartridge can be easily placed or removed from the Cartridge Dock 2400.

In some embodiments, the Cartridge Dock 2400 can comprise tubing slots 2410, on the end(s) and/or side(s) of the Organ Cartridge slots 2402. The tubing slots 2410 can be configured such that tubing can be connected to an Organ Cartridge 2404 before it is placed in the Organ Cartridge slot 2402, or remained connected to the Organ Cartridge 2404 without disconnection from the tubing while being placed in the Organ Cartridge slot 2402.

In some embodiments, the Cartridge Dock 2400 can also act as a stand that holds containers (e.g., tubes such as conical tubes) for the Organ Chip fluid input and/or output. For example, referring to FIG. 24A, in some embodiments, a Cartridge Dock 2400 can comprise at least two levels, e.g., a top level comprising at least one or more Organ Cartridge slots 2402 (e.g., 1, 2, 3, 4, 5, 6, 7, 8, 9, 10 or more slots) for placement of Organ Cartridges 2404; and a lower level configured to provide reservoir stands 2406 for stabilizing containers (e.g., tubes), e.g., waste containers 2414, and/or reagent container, that are fluidically connected to Organ Cartridge(s) and/or Organ Chip(s).

In some embodiments, the reservoir stand 2406 can have one or more recesses that hold syringes (e.g., standard Luer syringes). In some embodiments, the reservoir stand 2406 can also comprise at least one or more tubing slots so that the tubing can be connected before the syringe is placed in the stand. Each syringe can have a Luer or septum valve so that the reservoir can be removed and/or replaced without leaking fluid. The top surface of the syringe can be sealed with a syringe plunger, or with a polymeric membrane (e.g., PTFE membrane) that can allow for gas transfer with the incubator.

Figure 24B:
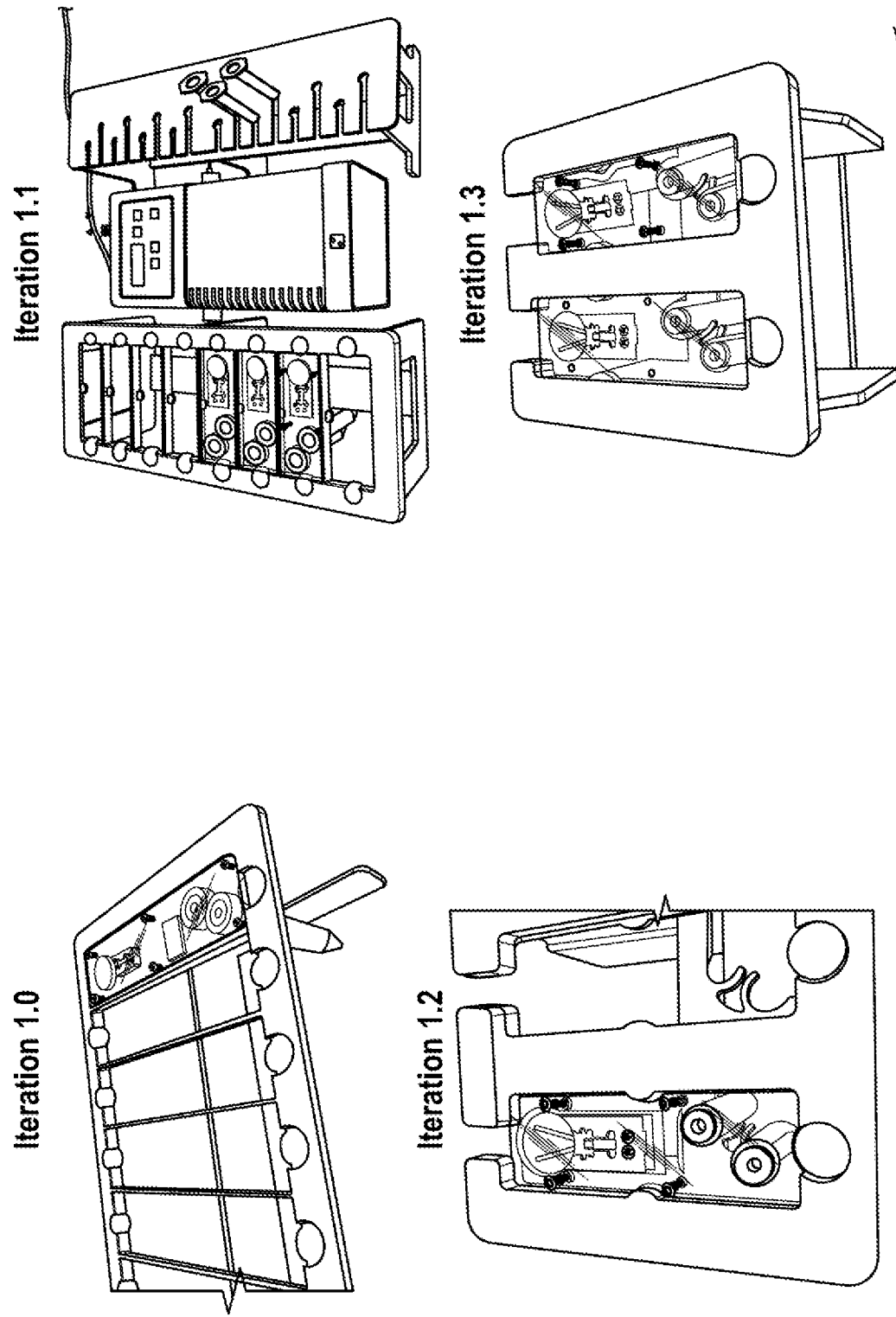

Some other exemplary embodiments of the Cartridge Dock are also shown in FIGS. 24B, 26 and 27. As shown in FIG. 26, in some embodiments, the Cartridge Dock can also provide placements of low dead-volume injection nozzles (LDVin) enclosed within a protective shroud 2604 for Cartridge-machine interface, where the Organ Cartridge can comprise a self-sealing or self-healing septum 2602 adaptably connected to fluidic port(s) of the Organ Cartridge 2600. In these embodiments, users do not have to individually connect and/or disconnect tubes; thus, cells cultured in the Organ Chips are less disturbed by fluidic connection/disconnection events. In addition, the Organ Cartridge can be fluidically and sterilely sealed after removal from the machine and the connector dead volume can be reduced by an order-of-magnitude.

Some other exemplary embodiments of the Cartridge Dock are also shown in FIGS. 24B, 26 and 27.

Fluidic Circuit

The fluidic architecture of Organ Chip, Organ Cartridge, Cartridge Dock, Organ Farm, or Interrogator device can be based on a two flow-channels design (i.e., fluidic bus system) that connects stock fluid reservoirs with biological samples, e.g., cells on the Organ Chips. For example, one of the two individual flow channels can be adapted for an efferent flow (e.g., simulation of arterial flow transport, microvascular or arterial system), while the other flow channel can be adapted for an afferent flow (e.g., simulation of venous flow transport, interstitial channel or venous system). Thus, in some embodiments, the fluidic architecture of the Organ Chip, Organ Cartridge, Cartridge Dock, Organ Farm, or Interrogator device is based on a two bus design—an Afferent Bus (e.g., Arterial System or Microvascular System) and an Efferent Bus (e.g., Venous System or Interstitial System) (FIGS. 17 & 18)—for both the Microvascular and Interstitial Channels.

As discussed herein, two or more Organ Chips can be interconnected and fluid can be routed through interconnected Organ Chips using a reconfigurable interconnect system. The interconnect system can be implemented, for example, on the Organ Chip level, on the Organ Cartridge level, as part of a Cartridge Dock, as part of an Organ Farm, and/or as part of an Organ Interrogator. Valves can select the operating mode of the various Organ Chips. The interconnected Organ Chips can, for example, be perfused using biological media or challenge agent, connected in series or parallel with other Organ Chips, or perfused with recirculating fluid around groups of one or more Organ Chips. Two buses are used, which to a limited extent emulate the in vivo afferent and efferent fluidic system. Fluid can be returned from the efferent bus to the afferent bus either through a specialized conduit (as illustrated) or through one or more Organ Chips (for example, though a Lung-on-chip). In some embodiment, two or more interconnect systems can beused, for example, one for the microvascular pathway and one for the interstitial pathway of the Organ Chips. FIG. 18 shows a schematic representation of an embodiment showing how fluid can be routed through interconnected Organ Chips.

The term "fluidic bus systems" as used herein refers to an interconnected circuit of fluid flow channels connecting various components described herein, e.g., Organ Chips, each of which can be a functional unit of an Organ in a microphysiological system network). The fluidic bus systems can deliver liquids, gases and aerosols for perfusion and recirculation to a single or multiple Organ Chips. The fluidic bus systems can further comprise pumps and pressure sensors to ensure the proper flow through each Organ Chip.

In some embodiments, two or more components described herein (e.g., Organ Chips, Organ Cartridges, Cartridge Docks, Organ Farms, or Interrogator devices) are connected together fluidically, i.e., fluidically connected. As used herein, the term "fluidically connected" refers to two or more components connected in an appropriate manner such that a fluid or a least a portion of a fluid can directly or indirectly pass or flow from one component to a second component. Without limitations, two or more components can be fluidically connected together, for example, using one or more fluid-transfer connecting means (e.g., adaptors, tubing, splitters, valves, and/or channels) between the two or more components. For example, two or more components can be fluidically connected by connecting an outlet of one component to an inlet of another component using tubing, a conduit, a channel, piping or any combinations thereof. In other embodiments, two or more components can be fluidically connected together with one or more other connecting means (e.g., devices, systems, and/or modules that can perform an additional function other than fluid transfer, e.g., but not limited to, trapping air bubbles, filtration, signal detection, and/or imaging) are present between the two or more components. In these embodiments, by way of example only, two or more Organ Chips can be fluidically connected, when the two or more Organ Chips are indirectly connected, e.g., through a biosensor, a filter, and/or an analytical instrument (e.g., via tubing), such that a fluid exiting the previous Organ Chip can be detoured to first flow through the biosensor, filter and/or analytical instrument, e.g., for detection, analysis and/or filtration of the fluid, before it enters the next Organ Chip. In these embodiments, at least a portion of the fluid can pass or flow from one Organ Chip to another Organ Chip.

Also provided herein are novel modular fluid control assemblies between the interfaces of different components, such as between the interfaces of the Organ Chips to Organ Chips, Organ Chips to Organ Cartridges, Organ Chips to Organ Farm, Organ Chips to Organ Interrogator, Organ Cartridges to Organ Cartridges, Organ Cartridges to Organ Farm, Organ Cartridges to Organ Interrogator, and the like. These interfaces provide pumps and valves capable of delivering precise small volume amounts of fluid at controlled flow rates to Organ Chips. These miniature microfluidic fluid control assemblies utilizing a planar fluid channel design that allows minimization of interconnect volumes and precise control of the extremely low fluid flow rates needed for Organ on a Chip constructs. In addition to the low volume planar design feature, these assemblies include one or more of the following design features:

a. Electrical actuation via stepper motors or geared dc motors equipped with rotary encoders for the pumping selecting of fluids b. Elastomeric pump and valve components that respond to localized pressure delivered by the motor assembly
c. A mechanism to deliver localized pressure to portions of fluidic channels in order to create either peristaltic pump action or localized on/off fluidic switch actuation via small balls or rollers that press against an elastomer.
d. A mechanism to control the localized pressure or tensioning delivered by the ball or roller.
e. A system for providing adequate alignment of the balls or rollers with the fluidic channel.
f. A technique for computing the motor shaft rotation angle required to move a specific ball or roller over a specific portion of a microfluidic channel in order to achieve fluidic on/off control.
g. A system to enable minimum labor to replace the Organ Chip or fluid head assemblies.

In some embodiments, the fluid control assemblies utilize a Rotary Planar Peristaltic Micropump and Rotary Planar Valve (RPPM and RPV) technologies (FIGS. 12 & 13), as described in PCT Publication No. WO2012/048261. These technologies provide microfluidic control capability at ~$1/10^{th}$ the cost of stand-alone commercial syringe and peristaltic pumps and microfluidic valve arrays. This can also support the switching modes for both the Perfusion Controller and pCA, since the screen-printed electrochemical sensor array from Vanderbilt Institute for Integrative Biosystems Research and Education (VIIBRE) (FIG. 14) can also be integrated in the Perfusion Controller. Without limitations, the Perfusion Controller can allow automated sample collection for liquid chromatography-mass spectrometry (LC-MS) and ion mobility-mass spectrometry (IM-MS) systems. Alternatively, other valve and pump technologies can be used to implement pumps and valves as needed to implement one or more of the functions described above.

In some embodiments, the systems described herein utilize Rotary Peristaltic Micropumps and Valves as described in U.S. Provisional Application No. 61/735,206 titled "Membrane-Based Fluid-Flow Control Devices," filed on Dec. 10, 2012, the content of which is incorporated herein by reference in its entirety.

In some embodiments, the fluidic conduits that are adapted to support the operation of one or more pumps or valves, as would be useful, for example, in the case of rotary peristaltic pumps and valves as described in U.S. Provisional Application No. 61/735,206 titled "Membrane-Based Fluid-Flow Control Devices," filed on Dec. 10, 2012, with pump-heads/valve-heads that can detach from the pump or valves membrane.

The Organ Chip, Organ Cartridge, or Cartridge Dock can be equipped with a five-position valve that selects whether its input will come from an upstream Organ Chip, Organ Cartridge, or Cartridge Dock, from a fresh fluid inlet, from either of the two buses, or from local recirculation. Similarly, each Organ Chip, Organ Cartridge, or Cartridge Dock's output can be directed using another five-position valve to a downstream Organ Chip, Organ Cartridge, or Cartridge Dock, a fluid-sampling or waste port, either of the two buses, or on-Organ Chip, Organ Cartridge, or Cartridge Dock recirculation. Additional two-position valves can ensure the proper flow direction in each of the buses, and can be used to divide the Organ Farm or Interrogator into two separate subsystems.

In some embodiments, the connective interfaces of the different components (e.g., Organ Chip, Organ Cartridge, Cartridge Dock, Organ Farm or Interrogator can be designed to have minimal dead volume and/or to prevent wetting or accumulation of liquid on areas adjacent to the flow path.

When the system is configured to reperfuse individual or groups of Organs, e.g., Organ Chips, the valves can be switched intermittently to introduce small volumes of fresh fluids (e.g., in order to replenish nutrients) while simultaneously passing the same volume of fluid out through the waste port; this outflow will also permit sampling for chemical analysis. Importantly, the dual bus architecture allows one to temporarily isolate an Organ Chip or Cartridge in order to treat it with a drug while allowing the other Organ Chips or Cartridges to bypass it and continue interacting. Furthermore, this architecture permits the Interrogator's fluidic system to be divided into several independent subsystems of physiologically relevant Organs, enabling multiple or replicate experiments on the same Interrogator simultaneously. The plug-and-play nature of the Organ Chips and Cartridges allows one to change the order of the Organ Chips (e.g. Organs), which can facilitate isolation of selected Organ Chips from others.

In some embodiments, a multi-way valve can be included, e.g., a two-way valve, within the fluidic circuit to ensure proper flow direction between the efferent flow and afferent flow channels. When the fluidic circuit is configured to reperfuse individual or groups of Organ Chips or Cartridges, the valves can be switched intermittently to introduce small volumes of fresh fluids (e.g., in order to replenish nutrients) while simultaneously passing the same volume of fluid out through the waste port; this outflow will also permit sampling for chemical analysis. Importantly, the dual flow channels can allow one to temporarily isolate a Organ Cartridge and/or an Organ Chip in order to treat it with a drug while allowing the other Organ Cartridges and/or other Organ Chips to bypass it and continue interacting. Furthermore, this dual flow channel can allow the Interrogator's fluidic system to be divided into several independent subsystems of physiologically relevant Organs, enabling multiple or replicate experiments on the same Interrogator simultaneously. The plug-and-play nature of the Cartridges allows one to change the order of the Organs-Chips (e.g. Organs), which can facilitate isolation of selected Organ Chips (e.g. Organs) from others.

In some embodiments, the fluidic circuit can include at least one multi-way inlet valve that can determine the source of a fluid flow into the inlet of the Organ Cartridge or the inlet of an Organ Chip. In such embodiments, the multi-way inlet valve can be a control inlet valve with at least two ways, at least three ways, at least four ways, at least five ways or more. Examples of inlet fluid sources include, but not limited to, an upstream Organ Cartridge, an upstream Organ Chip, a supply inlet, the efferent flow channel, the afferent flow channel, a recirculation fluid, and any combinations thereof.

Similarly, in some embodiments, the Organ Cartridge or the fluidic circuit can include at least one multi-way outlet valve that can direct a fluid flow from the outlet of the Organ Cartridge or the outlet of an Organ Chip to a different outlet destination. In such embodiments, the multi-way outlet valve can be a control outlet valve with at least two ways, at least three ways, at least four ways, at least five ways or more. Examples of the outlet destinations for an outlet fluid can include, without limitation, a downstream Organ Cartridge, a downstream Organ Chip, a fluid-sampling or waste port, the efferent flow channel, the afferent flow channel, a recirculation fluid, and any combinations thereof.

In some embodiments, the fluidic circuit can further comprise a fluid control element. Examples of fluid control elements include, without limitations, pumps (e.g., miniaturized pumps), pressure transducers, valves (e.g., rotary valves or pneumatic or other valves that provide closed loop control), bubble traps, gas exchange membranes, fluid sealing element (e.g., elastomeric O-rings and septa) and sensors (e.g., pH, $O_2$, glucose, lactate, etc.) to ensure proper flow to each Organ Chip.

In some embodiments, the fluidic circuit can further comprise a cleaning reservoir containing an antiseptic fluid, from which the antiseptic fluid can be pumped to the rest of the fluidic circuit, including the fluid contact surfaces of the Organ Chips, orga-Cartridges, Cartridge Docks, Organ Farm, and Organ-Interrogator for sterilization purposes. The cleaning reservoir can be configured so that the surfaces adjacent to the fluidic interfaces can be exposed to the antiseptic solution as well as the normally wetted surfaces. Additionally, alternate application of vacuum and clean sterile water can be used to flush away residual antiseptic solution.

In some embodiments, the ports of the fluidic circuit can be covered with an elastomeric septum, e.g., for perforation by a needle when in use to minimize bacterial contamination or water evaporation.

In some embodiments, the fluidic circuit can comprise one (e.g., one, two, three, four, five or more) bubble traps.

In some embodiments, at least a portion of the fluidic circuit can be in-Cartridge, i.e., integrated with the base substrate of the Organ Cartridge.

In other embodiments, at least a portion of the fluidic circuit can be detachable from the Organ Cartridge. For example, the detachable fluidic circuit can be pre-attached to the Organ Cartridge and be sterilized, e.g., using any known method in the art, such as using gamma irradiation, as an assembly prior to use. In other embodiments, at least a portion of or the entire fluidic circuit can be sterile, single-use disposable manifold elements.

Blood Substitutes

Each of the different human cell types representing the different Organ systems can be tested and cultured using different cell culture media and supplements. A key challenge for the successful integration of the different Organ Chips in their respective Organ Cartridges into the Cartridge Dock is the use of a common medium or universal Blood Substitute that can be perfused through the entire system and maintain viability and differentiated functions of all relevant linked Organ Chips. Accordingly, the Blood Substitute is any flowable media which provides all of the chemicals, nutrients, cytokines and trophic factors required by individual Organs, as well as physiologically relevant "vascular connections" and blood composition to mimic effects on PK/PD observed in humans. For example, in some embodiments, the Blood Substitute contains one or more plasma binding proteins. Without wishing to be bound by a theory, mimicking the plasma protein binding capacity of blood can help in more closely mimicking drug behavior. Generally only unbound drug is available to pass across membranes, and successful recapitulation of protein binding of drugs can improve PK/PD extrapolation.

In some embodiments, the Blood Substitute contains white blood cells.

As only a handful of different media compositions (e.g. DMEM, EBM-2, WEM, Iscove's, RPMI-1640) and supplements are shared by the different Organs described herein, one can mix different combinations of these media and their respective supplements required by the Organs being studied. However, the system incorporates an endothelium-lined Microvascular Channel that forms a vascular permeability barrier (junctional boundary) and a basement membrane between the endothelium and the parenchymal cells in a separate Interstitial Channel. This novel feature permits perfusing the Organ Chips with medium containing high levels of human serum or plasma similar to that found in human blood. Additionally, one can also use complete or partial (e.g., diluted) human blood samples.

Organ-Farm

In one aspect, provided herein is an Organ Farm. An Organ Farm is an instrument or a system that supports long term culturing of cells on one or more Organ Chips, i.e., the Organ Farm provides means for plating, culturing and maintaining living cells within an Organ Chip that is present in the Organ Farm. The Organ Farm comprises a controlled temperature, humidity, and gas environment capable of supporting one or more Organ Cartridges or individual Organ Chip assemblies each of which can be designed to create favorable fluidic, gas exchange, and nutrient conditions to foster growth and maintain the viability of multi-cell constructs which have biological properties similar to individual human or animal Organs.

An Organ Farm allows initial plating, preconditioning, and extended culture of individual Organ Chips perfused by Organ Cartridges in a multiplexed format for preconditioning the Organ mimics. Without limitations, preconditioning an Organ mimic can include optimally differentiating and forming multilayered tissue constructs. Such preconditioned Organ later can be used in an Organ Interrogator system described herein. The Organ Farm can also be used for experimenting with one or more Organ Chips. For example, perfused media can include a drug.

Generally, the Organ Farm is an instrument that can regulate medium flow to multiple Organ Chips to maintain their viability in long-term culture, for example, greater than four weeks. The Organ Farm can be placed within an incubator, e.g., a tissue culture incubator) to provide controlled temperature and $CO_2$, or these capabilities can be provided outside of an incubator by the Organ Farm instrument itself, using other Farm formats Generally, the Organ Farm comprises: (a) an apparatus or module for perfusing one or more Organ Chips with appropriate biological media using prescribed conditions; and (b) a sensor or monitor adapted for monitoring at least one environmental variable, e.g., temperature, gas mixtures (e.g., $CO_2$ content), and the like of the one or more Organ Chips.

Without limitation, the environmental variables can be controlled using pumps, valves, heating or cooling elements, etc. Perfusion can be by means of a fluidic circuit present in the Organ Farm for flowing nutrients, media etc. therethrough. As an example only, an Organ Chip in the Organ Farm can be perfused using one or more fluidic circuits comprised in the Organ Farm, which circuit can be connected directly or indirectly to the Organ Chip, e.g., an Organ Chip connected directly to the fluidic circuit of the Organ Farm or an Organ Chip disposed on a Organ Cartridge, which can be present in a Cartridge Dock.

In some embodiments, the Organ Farm can further comprise a control system for microfluidic handling in the microfluidic circuit. The Organ Farm can also provide reservoirs, for media and waste connected to the fluidic circuit. This can be useful for supporting a sufficient duration of unattended operation.

The Organ Farm can also provide one or more interfaces for attaching and detaching one or more Organ Chips, Organ Cartridges, and/or Cartridge Docks therefrom. This interface can provide inlet and outlet ports for fluidically connecting the fluidic circuit of the Organ Chip, Organ Cartridge, and/or Cartridge Dock to the fluidic circuit of the Organ Farm. Thus, in some embodiments, the Organ Farm further comprises a plurality of interfaces for attaching and detaching said Organ Chips to the instrument In one embodiment, the Organ Farm comprises a thermally regulated housing (e.g., a tissue culture incubator), wherein the thermally regulated housing comprises: (a) at least one fluidic circuit having an inlet and an outlet, in connection with at least one Organ Chip; and (b) a means for monitoring of cells on the at least one Organ Chip. The Organ Chip can be connected to the fluidic circuit of the Organ Farm either directly, through the fluidic circuit of a Organ Cartridge having the Organ Chip disposed thereon, or through the fluidic circuit of a Cartridge Dock having the Organ Chip disposed thereon (either directly or via a Organ Cartridge).

In some embodiments, the Organ Farm comprises: (a) a thermally regulated housing: (b) a plurality of Organ Chips disposed in the thermally regulated housing; (c) a fluidic circuit having at least one fluidic circuit having an inlet and an outlet, in connection with at least one of the plurality of Organ Chips; and (d) a means for monitoring of cells on at least one of the plurality of Organ Chips.

An Organ Farm can accommodate any number of Organ Chips, as restricted only by the size of the Organ Farm and enclosed Organ Chips (with or without a Organ Cartridge or Cartridge Dock). Generally, any the number Organ Chips can be housed within the Organ Farm. For example, an Organ Farm can accommodate from 1 to about 100 Organ Chips or Cartridge Docks comprising Organ Cartridges having one or more Organ Chips disposed thereon. In some embodiments, the Organ Farm can accommodate from about 1 to about 25, e.g., (e.g., 1, 2, 3, 4, 5, 6, 7, 8, 9, 10, 11, 12, 13, 14, 15, 16, 17, 28, 19, 20, 21, 22, 23, 24 or 25) Cartridge Docks. In one embodiment, three Cartridge Docks are housed within the thermally regulated housing shown in FIG. 19. In some embodiments, an Organ Farm contains at least one Cartridge Dock comprising an Organ Chip (FIG. 19).

In addition to the Cartridge Dock, the Organ Farm can also comprise sensors or monitors adapted for monitoring cells, e.g. cell viability and morphology. Such sensors and monitors can include optical methods (such as simple phase contrast microscopy), transepithelial electrical resistance (TEER) and the like. In some embodiments, the Organ Farm contains a microscope, which supports one or more imaging modalities including, for example, brightfield, darkfield, phase-contrast or epifluorescence imaging. In some embodiments, an Organ Farm contains a single Microscopy Blade. This allows for optical imaging of individual Organs to ensure continued viability and can provide a quick estimate of tissue growth and Organization. Although not necessary, the Farm can be equipped to provide simultaneous imaging of multiple Chips using the same number of Microscope Blades as the number of Organ Chips to be imaged simultaneously.

In some embodiments, imaging can be carried out with in-line microscopic imaging capabilities, e.g., a mini-microscope for in situ monitoring of cells as described Kim et al., *Lab Chip.* 2012 Oct. 21; 12(20):3976-82, content of which is incorporated herein by reference in its entirety.

In some embodiments, the Organ Farm provides for initial loading of cells into pre-sterilized Organ Chips held within individual Cartridges. In some embodiments, the Organ Farm provides for the addition or removal of one or more Organ Chips, Organ Cartridges, or Cartridge Docks without compromising sterility of adjacent modules.

In some embodiments, the Organ Farm provides means for monitoring cells in one or more Organ Chips present therein using electrochemical sensors to measure the metabolic activity of the cells through changes in pH and/or concentration of glucose, lactate, oxygen, or other substances as the perfusing media passes over the cells in the Organ Chip.

In some embodiments, the Organ Farm further comprises a means for actuating mechanical or electrical function of an Organ Chip enclosed in the Organ Farm.

In some embodiments, the Organ Farm is an incubator, e.g., a tissue culture incubator, with controlled temperature and $CO_2$ that can regulate medium flow to maintain long-term, for example, greater than four weeks, culture of different Organ Chips. In addition to using standard tissue culture incubators, other Farm formats can also be employed.

FIG. 19 is a photograph of an Organ Farm according to an embodiment described herein. The Organ Farm comprises an Organ Farm module (1902) in an incubator (1900). *The Farm module* (1902) comprises a Cartridge Dock (1904) having one or more Organ Cartridges (1906) attached to the Cartridge Dock (1904). *As shown each Organ Cartridge* (1906) *comprises an Organ Chip* (1908). As shown, the Farm module also comprises one or more pumps (1910) in connection with the Cartridge Dock and fluidically connected to the Organ Cartridge (1906) and/or the Organ Chip (1908).

Figure 28A:
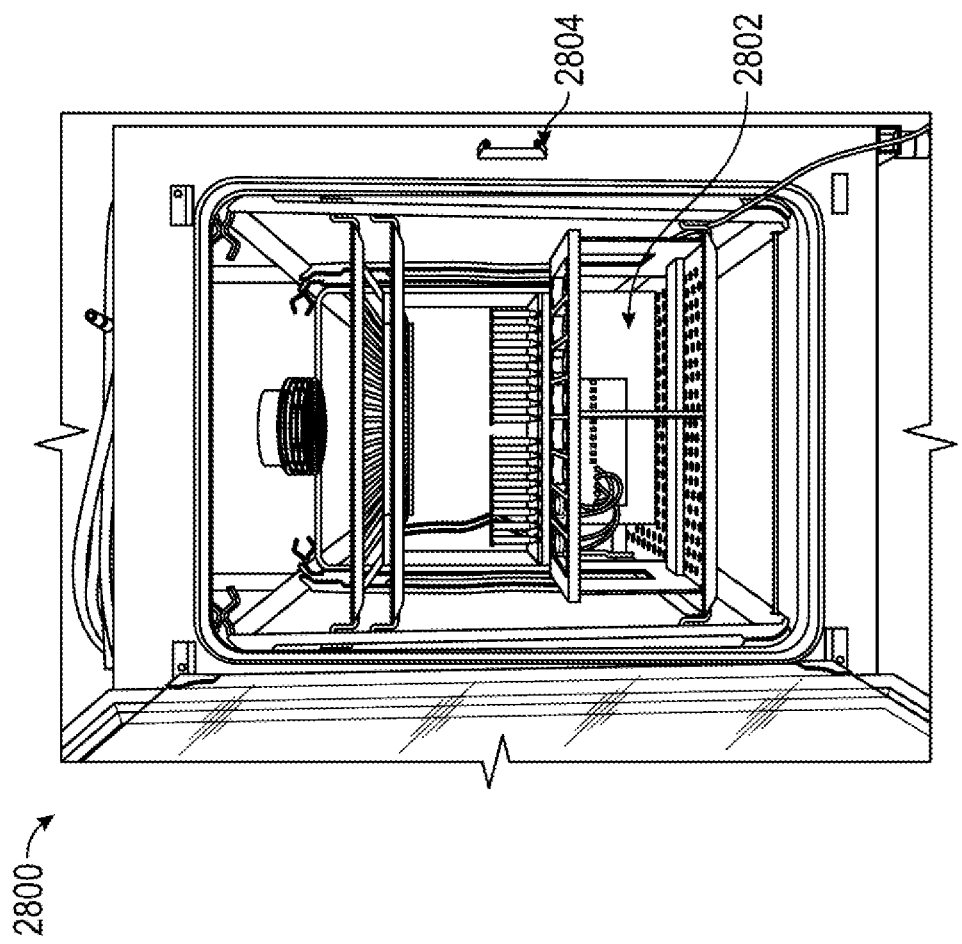
FIGS. 28A-28B are photographs showing an exemplary embodiment of an Organ Farm described herein and a module thereof.
Figure 28B:
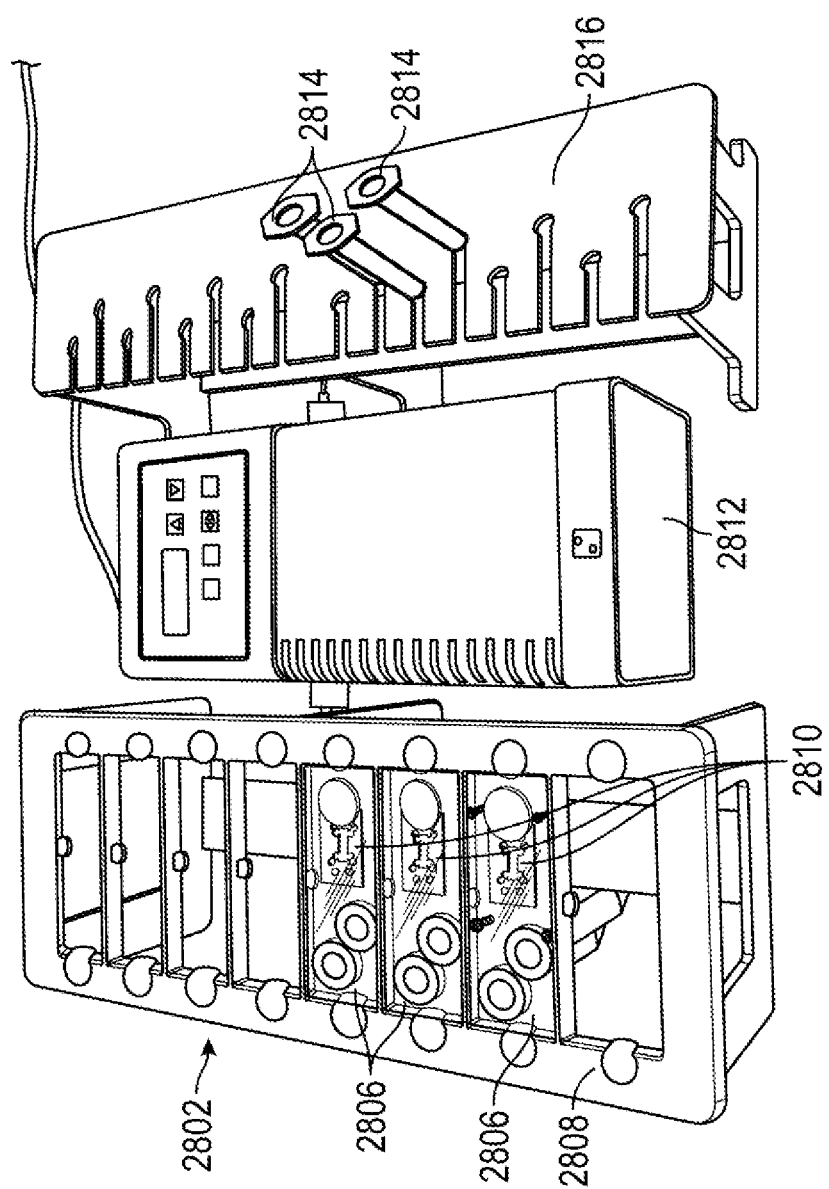

FIG. 28A is a photograph of an Organ Farm (2800) according to an embodiment described herein. As seen in FIG. 28A, the Organ Farm comprises a Farm module (2802) in an incubator (2804). Details of the Farm module (2802) are shown in FIG. 28B. The Farm module (2802) has three Organ Cartridges (2806) engaged in a Cartridge Dock (2808). Each of the Organ Cartridge (2806) has an Organ Chip (2810) disposed thereon. The Organ Cartridges (2806) are fluidicially connected to a 16-channel ISMATEC peristaltic pump (2812) and the two syringe reservoirs (2814) in the syringe reservoir stand (2816). The Cartridge, Organ Chip, 16-channel peristaltic pump, Cartridge bay, and reservoir bay are all integrated onto one incubator shelf as the first iteration of an Organ "FARM". This allows for a higher number of Organ Chip experiments in a single incubator. Fluidic connections can be made quickly and consistently during Cartridge handling, bubbles generated by off-gassing or fluidic connect/disconnects are removed by the bubble trap, and fluid output is captured by conveniently removable conicals.

Master Controller Computer

Flow of fluids and nutrients in an Organ Chip, Organ Cartridge, Cartridge-dock, Organ Farm, and/or Interrogator can be controlled individually by a Master Controller Computer. Accordingly, in some embodiments, the fluidics control system of each Organ Chip, Organ Cartridge, Cartridge Dock, Organ Farm, or Interrogator can be configured as independent subsystems.

In some embodiments, the Farm and Cartridge Dock can be controlled by a stand-alone computer-based system, and for example a Master Controller Computer, that provides Organ-specific flow of nutrients, appropriate valving, monitoring of the cellular samples, and recording functions that identify the history of individual Organ Chips, as well as control of temperature, moisture and carbon dioxide when not incorporated within a commercial tissue culture incubator.

In some embodiments, the Farm may provide stimulation to the Organ Chips, including mechanical (e.g. "breathing"), electrical (e.g. pacemaking) or optical (e.g. optogenetics). In some embodiments, the Farm may record sensor data, including for example data derived from microscopy, micro-clinical analyzers, pressure sensors, liquid-level sensors etc.

In some embodiments, user interface to the Master Controller Computer is by a desktop- or laptop-based computer, e.g., a PC.

In some embodiments, the Master Controller Computer is a microcontroller embedded into either the Cartridge Dock or each Organ Cartridge.

In some embodiments, a Master Controller Computer is used for periodic calibration of the electrochemical sensor arrays and/or controlling the valving and pumping operations. Such electrochemical sensor arrays and valving and pumping operations are needed to perform the electrochemical measurements, and to dispense fluids for external analysis to ensure long-term viability and functionality of the Organ mimics.

In some embodiments, a Master Controller Computer can be used to provide signals that establish valve and pump control conditions to fluidically connect two or more Organ Chips in parallel within their respective Organ Cartridges and Cartridge-dock. For example, two or more Organ Chips can be connected in series or parallel either transiently or continuously.

The various components of the Interrogator device can be controlled individually or by a Master Controller Computer. When used, the Master Controller Computer communicates with independent subsystem controllers. Generally, the subsystem controllers perform autonomous management of local sensing and actuation functions. This allows for a modular approach to the control architecture. Additionally, off-the-shelf subsystems can be interfaced to the intended bus structure to facilitate migration to custom subsystems. Subsystems of the Interrogator can communicate with each other and the controller at a multitude of data and data rates. In some embodiments, the Master Controller Computer and the independent subsystem controllers can communicate with each other fly.

In some embodiments, a Master Controller Computer is used to sequence a set of operations of settings over time, for example, as would be used in the course of a multi-step experiment. In some embodiments, a Master Controller Computer can be used to record data derived from various sensors, including for example data generated by microscopy, micro-clinical analyzers, electrophysiology sensors. In some embodiments, a Master Controller Computer can be used to provide inputs to the Organ Chips that include electrical stimulation, optical stimulation (for example, for optogenetics), mechanical actuation, etc.

As discussed herein the Organ Farm can provide fluid, gas and electrical connections between the Organ Chips and the control and analytical instrumentation.

An Organ Farm can microfluidically, mechanically and electrically connect to an Organ Chip either directly or via an Organ Cartridge. In some embodiments, the Organ Farm can comprise a temperature control unit. For example, a temperature control unit can comprise one or more thermistors that can be used to monitor temperature at one or more locations. Additionally, the temperature control unit can comprise a heating element that can be used, e.g., alone or in combination with the thermistors, to maintain temperature of the Organ Chips at 37±0.5° C. or at any other desired temperature.

In some embodiments, the Organ Farm can comprise at least one pump and/or pressure sensor for each Organ Chip to modulate an optimum flow specific for each Organ Chip. In some embodiments, systemic venous return pumps with pressure sensors can be used to maintain the desired arterial-venous pressure difference for varying Organ loads. Management of supply and waste fluids can allow removal of waste and replenishment of fresh Blood Substitute and drugs using temperature-controlled containers situated outside of the instrument enclosure. Electronic sensing of supply and waste liquids can also be incorporated to inform the operator of run-time capability as well as the need to resupply consumables or remove waste.

In some embodiments, the cells can be monitored by using electrochemical sensors to measure the metabolic activity of the cells through changes in pH and the concentration of glucose, lactate, oxygen and other substances as the perfusing media passes over the cells in the Organ Chip.

In some embodiments, the Organ Farm can control pressure regulation to balance mismatches between Chips based on variations in size or design can be provided using in-line pumps and rotary or pneumatic valves before or after each Organ, e.g., Organ Chip. Systemic venous return pumps with pressure sensors can maintain the desired arterial-venous pressure difference for varying Organ loads.

Generally, an Organ Farm can be configured to allow multiple modes of operation: 1) incubation and pretreatment, allowing one or multiple Organ Chips to be perfused independently with fresh media, blood, Blood Substitute or drug, 2) recirculation through individual Organs (e.g., for pre-activation of Liver enzymes), 3) recirculation of media, blood, or Blood Substitute through two or more, e.g., up to twenty, Organs in parallel, to mimic the Organ-Organ physiological coupling in animal or clinical studies, and 4) daisy chaining (connection in series) of one or more Organs to allow the outflow of one Organ to feed directly into another (e.g., Gut-Liver axis interactions). A similar level of control and sampling for liquids (and air) flowing through the Interstitial Channels can also be provided in the Interrogator device.

In some embodiments, the fluidics system utilizes peristaltic pumps or vibrating diaphragm or other pumps fitted with pressure transducers to deliver liquids to the Organ Farm. The Organ Farm, in turn, can feature two parallel fluidic bus systems, corresponding to the Arterial and Venous systems that connect to either the Microvascular or Interstitial Channels in each Organ Chip. The two bus systems (for each Channel) can deliver liquids, gases and aerosols to the Cartridges for perfusion and recirculation in single or multiple Organs. Additional connections between Cartridges in a Cartridge Dock can allow for recirculation within one Cartridge or between Cartridges.

In some embodiments, the Organ Farm provides for initial loading of cells into pre-sterilized Organ Chips held within the Organ Farm.

In some embodiments, the cyclic vacuum in the control channels can be modulated by pressure regulators in conjunction with electronically operated flow valves. The pressure in various channels can be monitored by electronic or microfabricated optical pressure transducers. In some embodiments the system is controlled by a dedicated modular microprocessor instrumentation control module within the electronic system architecture, in conjunction with a vacuum pump.

In some embodiments, a sensing module or technologies can be incorporated in the Organ Farm (i.e., external to the Organ Chip or the Organ Cartridge).

In some embodiments, the Organ Farm can further comprise at least one sensor for control of environmental conditions (e.g., temperature, humidity, pH, nutrient, waste, and/or shear stress), appropriate delivery of fluids and/or control of vacuum. Sensors for detection of different environmental conditions, fluid flow and pressure are known to a skilled artisan.

Microscope Blades

Figure 20:
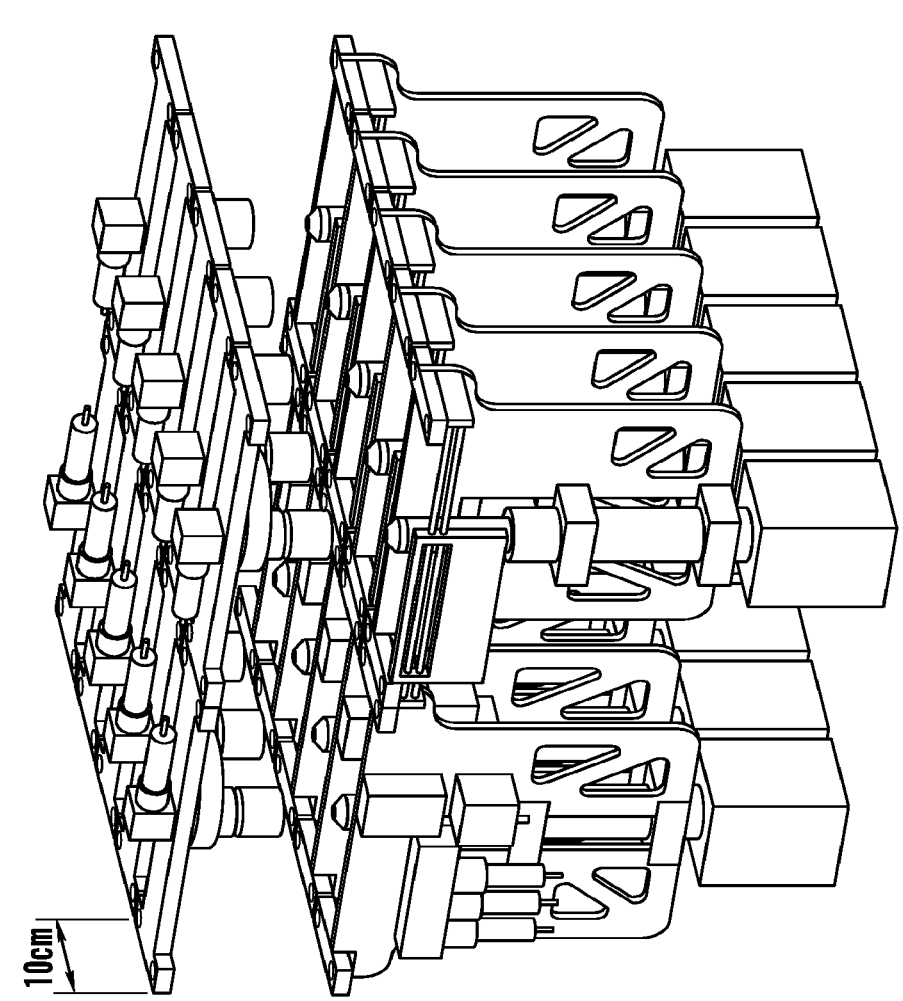
FIG. 20 is a schematic representation of the Microscope Blade concept (left) and an assembly of ten Microscope Blades (right).
Figure 20:
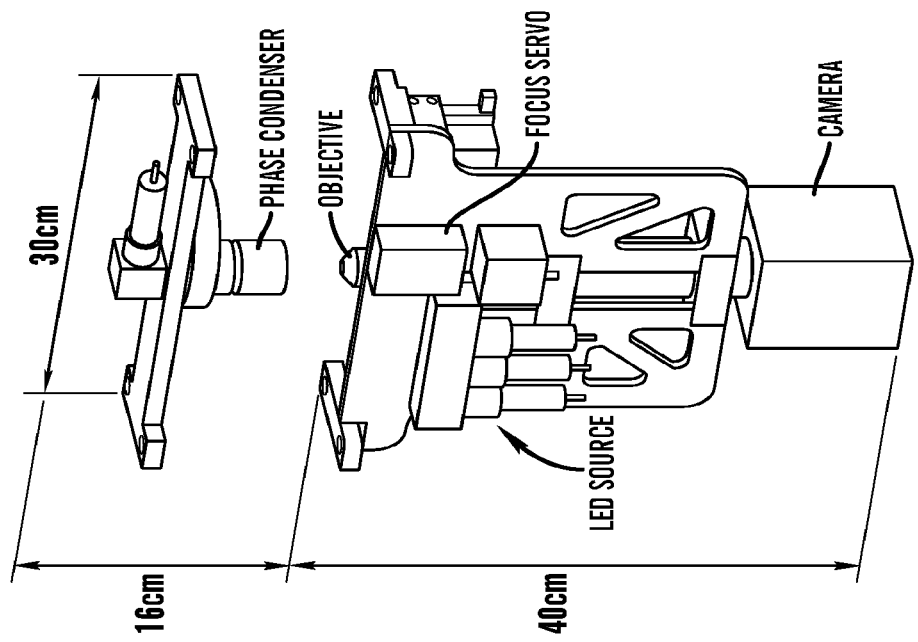

Each of these Microscopy Blades can support one or more microscopy modalities, including for example brightfield, darkfield, phase-contrast or epifluorescence imaging, and features a stackable form factor, so that the Organ Farm or Interrogator can be populated with Microscopy Blades incrementally as needed (FIG. 20). Accordingly, in some embodiments, the Microscopy Blades are built onto a motorized platform, so that the complete microscopy system can be scanned in two dimensions as a unit. In some embodiments, the Microscopy Blade itself comprises a motorized platform. Without wishing to be bound by a theory, this design permits imaging of multiple positions along the length of each Organ as well as several replicate lanes in each Cartridge without the complexity involved in motorizing each blade individually. Alternatively, Microscopy Blades could be motorized individually or in groups in one or multiple axes. In some embodiments, each Microscopy Blade includes its own focus control, which can for example make use of electromagnetic motors, piezoelectric motors, sonic motors, voicecoils or any combination thereof.

In some embodiments, the fluorescence filter within the Microscope Blades can be mounted on a motorized stage.

In some embodiments, fluorescence excitation and brightfield/phase illumination can be provided by LED or other electrooptical modules. Using LED modules can eliminate the need for mechanical shutters and provides improved thermal stability and lower thermal loads than, for example, an incandescent or arc lamp.

In some embodiments, autofocus capability can be implemented in software as known in the art or using hardware-based focus controllers Organ-Interrogator In another aspect, provided herein is an Organ-Interrogator system or device. As discussed herein, the Organ-Interrogator can be used for assessing cell viability and function in situ on each Organ Chip, and can contain a network of valves and ports that allow media samples to be withdrawn from the system to allow off-Chip assays of cell products (e.g., using LC/MS, nESI IM-MS, UPLC-IM-MS or other conventional analytical methodologies). An Interrogator device can be used to determine biological effects (e.g., but not limited to, toxicity, and/or immune response) of active agents one or more Organs.

Generally, the Organ Interrogator is an Organ Farm comprising a plurality of Organ Chips, which are interconnected. The Organ Interrogator can include at least one valve or port that allows media sample to be withdrawn from at least one of the Organ Chips in the device. The Organ Chip can be connected to the instrument either directly, by an Organ Cartridge having the Organ Chip disposed thereon, or through a Cartridge Dock having the Organ Chip disposed thereon (either directly or via an Organ Cartridge).

In some embodiments, the Organ-Interrogator is a device that comprises: (a) a plurality of Organ Chips which are interconnected; (b) an apparatus for perfusing Organ Chips in the device with appropriate biological media, the fluid originating at the outlet of one or more Organ Chips (including recirculation), and/or one or more challenge agents using prescribed conditions; (c) an apparatus for controlling the temperature of (and optionally gas mixture provided to) said Organ Chips; (d) a plurality of interfaces for attaching and detaching said Organ Chips to the device; and (e) at least one valve or port that allows media sample to be withdrawn from at least one of the Organ Chips.

Examples of active agents that can be used include, but are not limited to, cells (including, e.g., but not limited to, bacteria and/or virus), proteins, peptides, antigens, antibodies or portions thereof, enzymes, nucleic acids, siRNA, shRNA, aptamers, small molecules, antibiotics, therapeutic agents, molecular toxins, nanomaterials, particulates, aerosols, environmental contaminants or pollutants (e.g., but not limited to, microOrganisms, Organic/inOrganic contaminants present in food and/or water, and/or air pollutants), and any combinations thereof. In some embodiments, the in vitro microphysiological system can be used to evaluate active agents that are effective in treating a disease or disorder in an Organ, but might be toxic to other Organ systems.

In one embodiment, the Interrogator device can be used to carry out dynamic analysis of drug efficacy, toxicity and PK within an individual Organ and any selected combination of linked Organs for in culture. Without limitations, dynamic analysis of drug efficacy, toxicity and PK within an individual Organ and any selected combination of linked Organs can be conducted for at least one, at least two, at least three, at least four, at least five, at least six or more weeks in culture.

As discussed herein the Organ Interrogator can provide fluid, gas and electrical connections between the Organ Chips and the control and analytical instrumentation.

An Organ Interrogator can microfluidically, mechanically and electrically connect to an Organ Chip either directly or via an Organ Cartridge. In some embodiments, the Organ Interrogator can comprise a temperature control unit. For example, a temperature control unit can comprise one or more thermistors that can be used to monitor temperature at one or more locations. Additionally, the temperature control unit can comprise a heating element that can be used, e.g., alone or in combination with the thermistors, to maintain temperature of the Organ Chips at 37±0.5° C. or at any other desired temperature.

In some embodiments, the Organ Interrogator can comprise at least one pump and/or pressure sensor for each Organ Chip to modulate an optimum flow specific for each Organ Chip. In some embodiments, systemic venous return pumps with pressure sensors can be used to maintain the desired arterial-venous pressure difference for varying Organ loads. Management of supply and waste fluids can allow removal of waste and replenishment of fresh Blood Substitute and drugs using temperature-controlled containers situated outside of the instrument enclosure. Electronic sensing of supply and waste liquids can also be incorporated to inform the operator of run-time capability as well as the need to resupply consumables or remove waste.

In some embodiments, the cells can be monitored by using electrochemical sensors to measure the metabolic activity of the cells through changes in pH and the concentration of glucose, lactate, oxygen and other substances as the perfusing media passes over the cells in the Organ Chip.

In some embodiments, the Organ Interrogator can control pressure regulation to balance mismatches between Chips based on variations in size or design can be provided using in-line pumps and rotary or pneumatic valves before or after each Organ, e.g., Organ Chip. Systemic venous return pumps with pressure sensors can maintain the desired arterial-venous pressure difference for varying Organ loads.

Generally, an Organ Interrogator can be configured to allow multiple modes of operation: 1) incubation and pre-treatment, allowing one or multiple Organ Chips to be perfused independently with fresh media, blood, Blood Substitute or drug, 2) recirculation through individual Organs (e.g., for pre-activation of Liver enzymes), 3) recirculation of media, blood, or Blood Substitute through two or more, e.g., up to twenty, Organs in parallel, to mimic the Organ-Organ physiological coupling in animal or clinical studies, and 4) daisy chaining (connection in series) of one or more Organs to allow the outflow of one Organ to feed directly into another (e.g., Gut-Liver axis interactions). A similar level of control and sampling for liquids (and air) flowing through the Interstitial Channels can also be provided in the Interrogator device.

In some embodiments, the fluidics system utilizes peristaltic pumps or vibrating diaphragm or other pumps fitted with pressure transducers to deliver liquids to the Organ Interrogator. The Organ Interrogator, in turn, can feature two parallel fluidic bus systems, corresponding to the Arterial and Venous systems that connect to either the Microvascular or Interstitial Channels in each Organ Chip. The two bus systems (for each Channel) can deliver liquids, gases and aerosols to the Cartridges for perfusion and recirculation in single or multiple Organs. Additional connections between Cartridges in a Cartridge Dock can allow for recirculation within one Cartridge or between Cartridges.

In some embodiments, the Organ Interrogator provides for initial loading of cells into pre-sterilized Organ Chips held within the Organ Interrogator.

In some embodiments, the cyclic vacuum in the control channels can be modulated by pressure regulators in conjunction with electronically operated flow valves. The pressure in various channels can be monitored by electronic or microfabricated optical pressure transducers. In some embodiments the system is controlled by a dedicated modular microprocessor instrumentation control module within the electronic system architecture, in conjunction with a vacuum pump.

In some embodiments, a sensing module or technologies can be incorporated in the Organ Interrogator (i.e., external to the Organ Chip or the Organ Cartridge).

In some embodiments, the Organ Interrogator can further comprise at least one sensor for control of environmental conditions (e.g., temperature, humidity, pH, nutrient, waste, and/or shear stress), appropriate delivery of fluids and/or control of vacuum. Sensors for detection of different environmental conditions, fluid flow and pressure are known to a skilled artisan.

Depending on various target applications, e.g., for use as a disease model or for pharmacokinetics study of a drug, different combinations of Organ Chips can be selected within the Organ Interrogator. For example, in one embodiment, Lung Chips, Heart Chips and Liver Chips can be selected to be disposed on the Organ Cartridges because, without wishing to be bound by theory, they provide functionalities that are most critical for determination of clinically relevant pharmacokinetics (PK)/pharmacodynamics (PD) as well as efficacy and cardiotoxicity (which is the cause of more than 30% of all drug failures).

Figure 21:
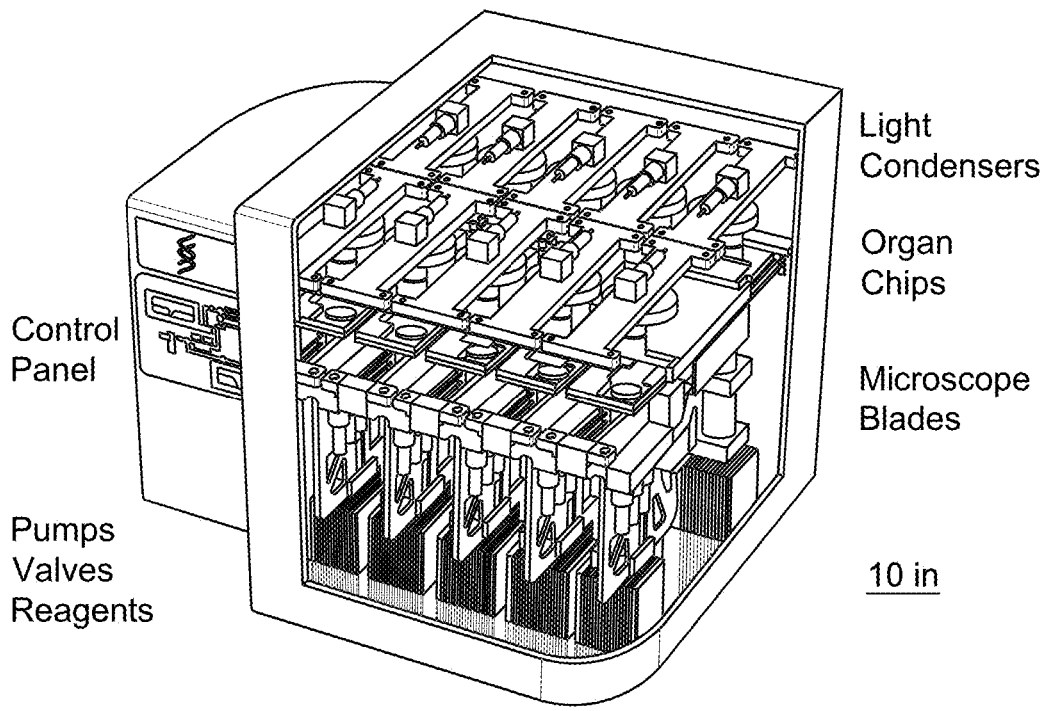
FIG. 21 is a schematic representation of an embodiment of the Organ Interrogator with a Cartridge-dock being examined by several Microscope Blades.

Various subsystems of the Organ Farm or Interrogator can be enclosed in a housing unit (enclosure) which can provide structure and interfaces for the integrated subsystems, including Organ Chips, Cartridges, Cartridge Docks, Microscope Blades, and the electronic, fluidic, and vacuum interface hardware (FIG. 21). Electronic hardware (printed circuit boards, Master Controller, and Interface Computer) can be external to the enclosure. Having the electronic hardware out of the enclosure provides easy access and better temperature management. In some embodiments, the chassis and main function assemblies are within the enclosure.

The universal Blood Substitute supply, oxygenation, vacuum, waste, liquid samples, electrical power, and data communication can be communicated from the instrument to external environment and analytical equipment (e.g., LC/MSMS or UPLC IM-MS, or nESI-IM-MS) via dedicated sterile ports. Thus, the instrument enclosure can comprise all necessary interfaces with bulkhead connectors or pass-throughs as appropriate, and where appropriate compartments, brackets, racks, or hangers for external system elements. Without limitations, an enclosure can be formed of any suitable material, including, but not limited to, metal (e.g. sheet metal), plastic, or a combination thereof.

In some embodiments, the enclosure comprises one or more inlet ports and one or more outlet ports for injecting or flowing a gas or air through the enclosure. The inlets can comprise one or more filters, e.g., HEPA filters, to reduce or eliminate any contaminates that may be present in the gas or air. An inlet port can be used to inject or force warm air through the enclosure to control the environment, e.g., temperature and atmospheric conditions, in the enclosure. The forced air is dry, so that no condensation forms on the optics or fluid-regulation components within the enclosure. Additionally, a humid environment is also not required, as the Cartridges can be enclosed with a moisture-impermeable layer to prevent evaporation of water from the Organ Chips. An inlet port can also be used for injecting controlled pulses of $CO_2$. When $CO_2$ is pulsed through the enclosure, the inlet port comprises one or more HEPA filters.

In some embodiments, the Organ Farm or Interrogator comprises one or more ports for collecting samples. The sample ports can be connected directly to a Cartridge-dock, Organ Chip, or to a fluidic circuit.

In some embodiments, the Organ Farm or Interrogator uses off-the-shelf components to provide environmental, fluidic, electrical and mechanical control of individual Organ Chips housed within Cartridges (FIGS. 11, 15 & 16).

In some instances, it may be desirable to sterilize one or more subsystems of the Organ Farm or Interrogator. Accordingly, the entire fluidic pathway from supply reservoirs to the Cartridge, and the waste and sampling lines, can be sterile, single-use disposable manifold elements. These fluidic circuits can be pre-attached to the Cartridge during manufacture, and sterilized as an assembly using gamma irradiation. Alternatively, ethylene oxide gas sterilizations can also be used. The fluid contact surfaces of the Organ Chip, Organ Cartridge, Cartridge Dock and all fluidic passages can be cleaned by mounting a cleaning Cartridge, through which an antiseptic solution is pumped. The cleaning Cartridge can be configured so that the surfaces adjacent to the fluidic interfaces are exposed to the antiseptic solution as well as the normally wetted surfaces.

Alternate application of vacuum and clean sterile water can be used to flush away residual antiseptic solution. Without wishing to be bound by a theory, this approach was found to be effective in a Baxter/Millipore system for home peritoneal dialysis. Additionally, BREATHE-EASY™ Sealing Membrane, a disposable, adhesive-backed membrane that is permeable to $O_2$, $CO_2$ and water vapor, or another such membrane can be used to eliminate cross-contamination or microbial infiltration from any ports that need to remain open to air when devices or subassemblies have to be handled outside of a sterile, laminar flow hood. Further, 90% ethanol can be used to sterilize biologically active surfaces, such as enzyme-coated glucose, lactate, pH, or $O_2$ sensors.

In some embodiments, the Organ Farm or Interrogator comprises HEPA-filtered positive pressure to prevent entry of contaminated particles or spores into the Cartridge loading area.

For access to internal components, hinged covers can be included on the enclosure. For control of temperature and ambient air flow, the hinged covers can have gaskets. In some embodiments, the covers can incorporate transparent panels. This allows visualization of internal elements without opening or removing panels.

Without limitation, an enclosure can be formed of any suitable material. Accordingly, in some embodiments, the enclosure is formed from a metal (e.g., sheet metal) or plastic, or a combination thereof.

In some embodiments, the Organ Farm or Interrogator comprises a microfluidic aerosol drug delivery device. Microfluidic aerosol drug delivery devices are described, for example, in U.S. Provisional Patent Application No. 61,483,837 filed May 9, 2011, the content of which is incorporated herein by reference in its entirety. The aerosol drug delivery device can be connected to the Organ Chip.

In some embodiments, the Organ Farm or Interrogator comprises one or more (e.g., one, two, three, four, five, six, seven, eight, nine, ten, eleven, twelve, thirteen, fourteen, fifteen or more) microscopes. In some embodiments, these microscopes are Microscope Blades. The number of Microscope Blades in the Organ Farm or Interrogator can be the same as the number of Organ Chips to be monitored simultaneously. In one embodiment, the Organ Farm or Interrogator comprises ten Microscope Blades, one for each Organ Chip.

In some embodiments, the Organ Farm or Interrogator comprises one or more (e.g., one, two, three, four, five, six, seven, eight, nine, ten, eleven, twelve, thirteen, fourteen, fifteen or more) Cartridge-docks for Organ Chips or Organ Cartridges and integrated control systems for microfluidic nutrient and air flow, thermal regulation, $CO_2$, humidity, fluid shear stress, cyclic mechanical strain and electrical stimulation and to maintain differentiated Organ functions for long-term culture, as well as simultaneous real-time imaging and biochemical and electrophysiological analysis of Organ Chips held within the Organ Farm or Interrogator.

In some embodiments, the active agent (e.g., drugs), and/or fresh medium, blood or Blood Substitute can be introduced into the "Arterial" port, while samples and waste fluids is removed from the "Venous" outflow port (FIG. 17).

In some embodiments, the Organ Farm or Interrogator permits programmable control. Such a programmable control can be implemented using in-line pumps to isolate or recirculate flow in any individual Organ Chip (e.g., precondition liver Chip with a P450 inducer) or combination of Organ Chips (e.g., link Gut to Liver) in any desired order. An exemplary Fluidic Architecture is shown in FIG. 18 illustrating how fluid can be routed through interconnected Organ Chips using a reconfigurable interconnect system. The Organ Chips can, for example, be perfused using biological media or challenge agent, connected in series or parallel with other Organ Chips, or perfused with recirculating fluid around groups of one or more Organ Chips. Two buses are used, which to a limited extent emulate the in vivo afferent and efferent fluidic system. Fluid can be returned from the efferent bus to the afferent bus either through a specialized conduit (as illustrated) or through one or more Organ Chips (for example, though a Lung-on-chip). In some embodiment, two or more interconnect systems are used, for example, one for the microvascular pathway and one for the interstitial pathway of the Organ Chips. The interconnect system can be implemented, for example, on the Organ Chip level, on the Organ Cartridge level, as part of a Cartridge Dock, as part of an Organ Farm, and/or as part of an Organ Interrogator. Valves can select the operating mode of the various Organ Chips.

Analytical functions can be carried out in-line or off-line as the need be. In some embodiments, one or more, up to all, non-optical analytical functions can be carried out off-line in the Organ Interrogator device.

The Organ Farm or Interrogator can comprise apparatus or monitors adapted for monitoring of one more Organ responses. In some embodiments, the Organ Farm or Interrogator can monitor one or more (e.g., one, two, three, four, five, six, seven, eight, nine, ten or more) different Organ responses with the aid of time-lapse optical microscopy. Because in some cases imaging configurations can differ between Organ types, and to enable time-lapse imaging cycles (5 minutes for most Organs; shorter for muscle contraction), each Organ Chip can be provided with its own low-cost custom microscopy module, e.g., a Microscopy Blade.

The fluidics control system in the Organ Farm or Interrogator can be configured as independent subsystems for each Organ Chip, Organ Cartridge, or Cartridge Dock, or as one master system for all of the Organ Chips, Organ Cartridges, or Cartridge Docks. In some embodiments, the fluidics system utilizes peristaltic or vibrating diaphragm or other pumps fitted with pressure transducers to deliver liquids to the Organ Chip, Organ Cartridge or Cartridge Dock.

The Organ Farm or Interrogator can comprise two parallel fluidic bus systems, corresponding to the Arterial and Venous systems that connect to either the Microvascular or Interstitial Channels in each Organ Chip (FIG. 18). The two bus systems (for each Channel) can deliver liquids, gases and aerosols to the Cartridges for perfusion and recirculation in single or multiple Organ Chips.

In some embodiments, the Organ Farm or Interrogator comprises one or more sensing modules or technologies (e.g., sensors) for assaying and control of one or more of environmental conditions, appropriate delivery of fluids, and vacuum. Environmental conditions to be assayed or controlled can include, but are not limited to, pH, $O_2$ levels, $CO_2$ levels, glucose levels, lactate levels, humidity level, and ion concentrations. Additional conditions can include temperature, flow rates, pressure, fluid shear stress, mechanical strain, and electrical strain.

Without wishing to be bound by a theory, Organ Farm or Interrogator allows one to apply physiologically relevant levels of chemical, electrical and mechanical strains to the Organ mimics. For example, physiologically relevant levels of cyclic mechanical strain can be provided to the Lung Chip and other relevant Organ Chips by vacuum channels adjacent to, but not in fluidic communication with, the tissue construct support membranes (FIG. 3), as previously described by the inventors (2). In another example, Heart, Skeletal and Airway muscle tissues can be subjected to controlled electrical stimulation via platinum electrodes microfabricated into the channels of the Organ Chip devices.

The Organ Farm or Interrogator can be designed to be compatible with the Organ Chips, Organ Cartridge, and/or Cartridge Docks described herein.

Without limitations, the Interrogator can provide appropriate environmental support and facilitate control and measurement functionality for one or more Organ Chips enclosed therein. The Interrogator can be designed to provide the detailed technology for studying multi-Organ interactions and in this context can provide one or more of the following functionalities:

a. Microscopic optical interrogation of individual Organ modules through the use of Microscope Blades or similar optical technology.
b. Support of long-term cell culture.
c. Experimental control of Organ Cartridges or Cartridge-docks.
d. Interfacing a Master Control Computer to the enclosed Organ Cartridges or Cartridge-docks.
e. Off-line support of liquid chromatography, mass spectroscopy or other waste sample analysis.
f. High-level control of nutrients, air flow, CO2, humidity, fluid shear stress, cyclic and mechanical strain, or electrical stimulation of the enclosed Organ Chips.

System Integration

The various subsystems described herein, e.g., Organ Farm, Interrogator device, Organ Cartridges and Organ Chips, can be integrated into one system to provide a Microphysiological Platform.

In one embodiment of the Microphysiological Platform, all Organs can be cultured in parallel as individual Organs (FIGS. 2 and 18), and all Organs connected to the same module receive common medium, which can be specially formulated to promote tissue formation, if necessary, i.e., before transfer to the Interrogator where a shared Blood Substitute (see below) can be utilized.

In some embodiments, the Organ Farm or Interrogator provides multiple Organ Chips for pharmacological studies.

Prediction and Validation

An Interrogator device described herein can be used to characterize the effects of drugs and other test compounds on different Organs. By way of example, an Interrogator device described herein can be used to characterize the effects of drugs that have available human clinical data in Organ Chips representing ten or more human Organ systems, both individually and in combination (FIG. 21). For validation studies, drugs can have a range of mechanisms of actions, toxicities and clearance mechanisms relevant to the Organ Chips selected. For example, drugs can be selected from those shown in Table 1, which have a range of mechanisms of actions, toxicities and clearance mechanisms relevant to a selected set of Organ Chips, e.g., Lung, Heart and Liver Chips, and their metabolism and clearance should alter as additional Organ Chips are added over time (e.g., drugs that undergo renal clearance would produce different results in a system without a kidney Chip). This drug set can also allow one to explore the major routes of drug administration, including oral, intravenous (i.v.) and transdermal, as well as aerosol in the future (being developed in parallel with support from FDA/NIH), key PK mechanisms for clearance (renal, liver) and drug-drug interactions' inhibition and/or induction of CYP450 enzymes, such as CYP3A4, and drug transporters, such as Pgp), and critical barrier functions (e.g., BBB, Skin, Gut). Additional compounds can serve as potential back-ups in cases where there are any technical or functional issues identified with any of the drugs in the initial set.

By way of example only, the cells within an Organ Chip in the Interrogator can be exposed to an active agent (e.g. a drug) by flowing a fluid containing the active agent through a channel of the Organ Chip or an integrated system of different Organ Chips (e.g. in the Interrogator), such that the fluid is in contact with the cells. In some embodiments, the cells within the Organ Chip can be exposed to an aerosol by flowing a gaseous fluid containing the aerosolized microdroplets of a drug through a channel of an Organ Chip or an integrated system of different Organ Chips such that the gaseous fluid is in contact with the cells. Cell response in one or more Organ Chips can then be measured after or monitored over a period of time. Examples of cell response can include, but are not limited to, viability, proliferation, respiration, metabolism, movement of the cells (e.g., migration, contractile motions), differential expression of biomarkers, and/or production and/or release of certain molecules by the cells. Any methods known in the art can be utilized for detecting or measuring a cell response, e.g., immunostaining, microscopy, immunoassays, PCR, and/or ECG measurements.

In some embodiments where the cells are collected from a subject, a treatment regimen (e.g., a therapeutic agent and/or dosage that works best, among others, for the subject) can be selected and/or optimized by culturing the subject-specific cells in the Organ Chips Interrogator systems described herein, exposing the cells to different therapeutic agents and/or dosages, and monitoring the cellular response to various combinations.

In some embodiments, the cells can be observed by microscopy for morphological changes. In some embodiments, the contractile motion of the cells can be measured by ECG measurements. In some embodiments, the cells can be stained for a target protein, e.g., a biomarker, and then observed under a microscope. In some embodiments, the cells can be collected from the Organ Chips for further analysis, such as RNA, DNA and/or protein analysis. In some embodiments, the culture medium conditioned by the cells can be collected for further analysis, such as RNA, DNA and/or protein analysis. One of skill in the art can readily perform various assays for detecting or measuring different kinds of cell responses.

Initial drug validation of an Interrogator device can be done with four compounds, e.g., terfenadine, fexofenadine, ketoconazole and isoproterenol, that elicit relevant responses from each of the three Organ Chips (Lung, Heart, Liver) individually, and in combination. This allows detection of effects of changes in PK/PD and toxicity that have been shown to be due to drug metabolism and drug-drug interactions in the liver (e.g., CYP450 inhibition of ketoconazole). Clinical doses for in vitro studies can be extrapolated from mathematical models. The mathematical models can also be used for helping dose range finding studies. Dose range finding studies can be carried out with individual Organs in the Farm initially, and then the Interrogator, to establish appropriate doses using relevant physiological measurements for Organ-Organ physiological coupling studies. For example, with terfenadine, one can correlate the free plasma levels that cause prolongation of QT interval in a subject with the prolongation of field potential duration using equivalent concentrations in the heart Chip.

TABLE 1

| Drug category & Compounds | | Mechaism of | Efficacy Target | | Clearence Mechanism | Administration | |
|---|---|---|---|---|---|---|---|
| Category | Drug/Vaccine | Action | Organ | Organ Toxicity | (for PK) | Route | Period |
| Safe + Effective | Fexofenadine | Antihistamine | Lung | | Liver, no BBB (PGP substrate) | Oral | All |
| | Ketoconazole | Antifungal | Fungi/absorbs over skin | Liver DDI, tests | Liver | Transdermal/Oral | All |
| | Ibuprofen | Antiinflammatory | Multiple | | Liver | Oral | Alt. |
| | Albuterol | beta-2 agonist | Smooth muscle | | Liver | Aerosol | Alt. |
| | Sildenafil | PDE-3 inhibitor | Smooth muscle | | Liver | Oral | Alt. |
| | Tamiflu | antiviral agent; influenza A + B | Lung, viral infection | Brain; tox in children <1 yr | Liver; Renal | Oral | Alt. |
| Safe + Ineffective | Nesiritide | B-type natriuretic peptide | Smooth muscle | | Proteolysis, Renal | I.V. | 1-3 |
| | Latrepirdine | Antihistamine | Brain | | (Crosses BBB) | Oral | Alt. |
| | Denufosol | P2Y2 agonist | Lung | | Aerosol | Aerosol | Alt. |
| Unsafe + Effective (*example of a drug thought to be safe in preclinical testing, later found to be unsafe in humans) | Terfenadine* | Antihistamine | Lung | Heart arrhythmia | Liver; DDI in Liver; no BBB | Oral | All |
| | Isoproterenol | Beta receptor agonist (1 & 2) | Heart, Smooth muscle, Lung | Heart | Renal | I.V., Aerosol | All |
| | Cisplatin | Anticancer | Lung/tumor | Kidney, Heart, Gut, BM, BBB | Renal | I.V. | 1-3 |
| | Amiodarone | Heart ion channels | Heart | Lung, liver | Liver | I.V. Oral | 1-3 |
| | Cerivastatin | Statin | Liver | Skeletal muscle, Kidney, Liver | Liver | Oral | 2-3 |
| | Doxorubicin | Anticancer | Tumor | Heart, gut, bone marrow, skin | Liver, Renal | I.V. | Alt. |
| | Troglitazone* | PPAR-gamma activator | Skeletal muscle/fat | Liver | Liver | Oral | Alt. |
| | Propoxyphene* | Opiod | Brain | Heart, gut | Liver, Renal | Oral | Alt. |
| Unsafe + Ineffective | Cefazolin | Antibacterial | Antibacterial | Lung, Kidney | Renal | I.V., Oral | 1-3 |
| | Vesnarinone | PDE-3 inhibitor | Heart | Heart | Liver | Oral | Alt. |
| | Xigris (activated protein C) | Coagulation cascade | Severe sepsis | Serious bleeding | Plasma, Kidney, Liver | I.V. | Alt. |

One can easily validate integrated Platform performance by testing the effects, clearance, distribution and cardiotoxicity of the unsafe/effective antihistamine, terfenadine (a.k.a. Seldane) and its safe/effective active metabolite, fexofenadine (a.k.a. Allegra) in the microfluidically linked Lung, Heart and Liver Chips. In some embodiments, efficacy of antihistamines can be measured using Lung Chips which comprise human mast cells and measuring histamine release. Terfenadine is a prime example of a compound that was initially thought to be safe and was a billion-dollar drug before rare, unexpected deaths were observed in patients, leading to its removal from the market. Terfenadine is rapidly metabolized by the liver CYP3A4 enzyme to fexofenadine. The metabolite which is now FDA-approved is safe and effective; however, terfenadine itself is cardiotoxic at higher doses in humans (due to hERG bLock, QT prolongation, and lethal arrhythmias) when levels remain high due to drug-drug interactions when patients receive other medications that inhibit CYP3A4 activity, such as the antifungal ketoconazole (safe/effective). Without wishing to be bound by a theory, one of skill in the art can identify this type of cardiotoxicity in vitro using an Organ Interrogator described herein. However, these drugs only produce cardiotoxicity by altering electrical conduction responses, and thus, to demonstrate the physiological mimicry of cardiac contractile function by the Heart Chip, one can also study isoproterenol (effective/unsafe), which can stimulate contractility, increase beating rate, and shorten the cardiac action potential. Thus, using the set of the four indicated drugs, one can evaluate and validate an Interrogator device against two of the four categories: safe/effective (fexofenadine, ketoconazole) and unsafe/effective (terfenadine, isoproterenol), as well as a key drug that was initially thought to be safe based on preclinical data, but later found to be unsafe in humans (terfenadine).

A different combination of Organ Chips in an Interrogator device can be used to study effects of drugs. For example, the presence of a Kidney Chip in the Interrogator system provides a unique model to study metabolism-transporter interplay, which is a key determinant of in vivo PK and transporter-based drug-drug interactions that play a major role in determining toxicity in humans. Importantly, these interactions cannot be studied in animal models due to marked species differences in regulation of CYP450 enzymes and transporters (e.g., PXR). Isoproterenol is also primarily metabolized and excreted by the kidney in humans, which can alter the responses and clearance behavior seen in an Interrogator device without a Kidney Chip.

A Gut Chip can allow one to characterize barrier tissue and absorption. In some embodiments, absorption through the Gut Chip can be modeled with oral formulations of terfenadine and fexofenadine.

An Interrogator device described herein can be used to characterize the physiological responses (efficacy, toxicity and PK/PD) of the same drugs to different linked Organ Chip combinations over time. For example, additional drugs can be used for studying the remaining safe/ineffective and unsafe/ineffective categories outlined in Table 1, and characterize the physiological responses (efficacy, toxicity and PK/PD) of the same drugs to different linked Organ Chip combinations over time.

For example, the antibiotic Cefazolin (unsafe/ineffective) that has lost efficacy due to developed resistance in many strains, and that produces pulmonary blood clots and nephrotoxicity, can be evaluated in Lung and Kidney Chips. The anti-cancer drug, cisplatin (unsafe/effective) can also be studied to determine if one can detect its dose-limiting side effects of gut, kidney and heart toxicity; efficacy also can be measured by placing human tumor cells in relevant Organs. The antiarrhythmic amiodarone (unsafe/effective) can also be evaluated for its arrhythmia-suppressing effects in the Heart Chip, and for toxicity in the Lung and Liver Chips. Nesiritide (safe/ineffective), which is a safe B-type natriuretic peptide-based smooth and vascular muscle dilator that recently failed a large clinical trial for efficacy in relieving dyspnea in heart failure patients; as it is primarily eliminated by the kidney, one can expect different results when a Kidney Chip is integrated into the Interrogator system or not.

Cerivastatin (unsafe/effective) can be evaluated in the Liver and Skeletal Muscle Chips to measure its effects on cytotoxicity as a correlate for its major toxicities in vivo (rhabdylomysis) and liver toxicity. Because a kidney Chip can be integrated in the Platform, one can also evaluate the effects of increased myoglobin in shared circulation, and evaluate whether these levels can produce damage in the Kidney Chip as seen in vivo.

The same compounds can also be studied for additional toxicities on target effects on any additional Organ Chips. For example, terfenadine and fexofenadine can be tested to evaluate their effects on skin (co-cultured with mast cells in a model of ectopic dermatitis) and on barrier function of our Blood-Brain Barrier Chip (because they are substrates for the Pgp efflux drug transporter that actively pumps them out of brain). The absorption of ketoconazole across a Skin Chip also can be measured, and one can determine whether its absorption produces testicular toxicity, as measured by inhibition of steroidogenesis.

In another example, the side effects of bone marrow suppression by cisplatin can be evaluated using the Bone Marrow Chip.

One can also integrate aerosol delivery into the Lung Chip and can evaluate PK and efficacy of aerosol delivery of drugs, such as isoproterenol, in the Lung and Airway Smooth Muscle Chips, as well as cardiac side effects in the Heart Chip. One can also integrate a Lung Bronchial Epithelial Chip into the system.

Additionally, approaches similar to those described herein can used to explore different routes of administration with different combinations of Organ Chips over time to obtain the most information possible given the parameters one can vary, and the measurements one can carry out using the Human Organ Chip Microphysiological Platform described herein.

In another embodiment, efficacy of the antihistamines can be measured by including human mast cells (isolated from fresh human lung specimens from cadavers or from bronchopulmonary lavage, or the human HMC-1 mast cell line) in the Lung Chip and measuring terfenadine/fexofenadine-induced mast cell degranulation using LC/MS and antibody assays. Prolongation of field potentials in MTFs within the Heart Chip can be measured using a modified multielectrode array contained within the electrophysiological chamber (FIGS. 5A-5C). To mimic drug-drug interactions that lead to changes in PK and subsequent terfenadine toxicity, one can co-administer terfenadine with ketoconazole or pre-treat the Liver Chip for hours to one day before integrating the multi-Organ systems. One can utilize sampling and off-platform analysis to quantify levels of fexofenadine and terfenadine in the platform described herein using LC-MS, ultraperformance liquid chromatography (UPLC) IM-MS, or nanoelectrospray (nESI) IM-MS and the effective/safe drug fexofenadine can be used a negative control. Cardiotoxicity can be assessed by measuring changes in electrical conduction and heart contractile force generation in MTFs in the Heart Chip (4). In addition, one can use microfluorimetry with calcium-sensitive dyes (Fluo-4) to monitor effects on intracellular calcium, a key component of cardiac excitation-contraction coupling and a determinant of contractile magnitude, and measure effects on release of troponin and lactate dehydrogenase (LDH), as well as mitochondrial membrane integrity in cardiac cells using biochemical and microscopic analysis off-line. Additional endpoints for toxicity and inflammation in all Organs can include measuring release of reactive oxygen species (ROS) and ICAM-1 expression in endothelium, as well as immune cell adhesion and diapedesis using microfluorimetry, as we have in the past (2). Classic endpoints of liver toxicity can be measured, including apoptosis, lipid accumulation, mitochondrial membrane integrity, cellular ATP, glutathione, and LDH. CYP450 activity also can be measured using standard probe substrates (e.g., testosterone) assays and LC/MS as described elsewhere (5, 6), as it is critical for the drug-drug interactions.

Bronchodilator effects can be evaluated by measuring changes in diastolic tension and changes in cAMP in airway smooth muscle MTFs in the Lung Airway Chip. Efficiencies of drug delivery across different barriers (e.g., Gut, Skin, BBB, aerosol in the Lung) can be determined by measuring levels in the circulating Blood Substitute using LC/MS off-line relative to delivering the same amount of compound i.v. in this model system.

One can also measure basic Organ Chip functions on-Chip using the MicroClinical Analyzer (pCA) to quantitate changes in glucose, pH, lactate, and $O_2$ in real-time. Transient suspension of flow into the Chip can increase the magnitude of the changes in these concentrations and hence improve the accuracy of their determination and also allow determination of the rates at which these substances are being consumed or produced, i.e., the fluxes of these substances. Importantly, this analytical device can be easily modified to detect different critical substrates (e.g., LDH, ATP, glutathione) over time by immobilizing relevant enzymes or ligands on its microelectrodes. Effects on drug clearance and PK/PD can be determined when drugs are administered i.v. with or without flow to the Liver Chip, by measuring changes the levels of parent compound and metabolites within fluids collected from the waste port using LC/MS. One can use the substrate depletion method (14) in which the in vitro half-life ($t_{1/2}$) of the parent compound is determined by regression analysis of the percent parent disappearance vs. time curve. Intrinsic clearance can be calculated and scaled to in vivo predictions based on published models (15), and then made available for computational modeling studies such as those conducted by CFD Research Corporation (CFDRC).

The Platform described herein can be used to develop PK/PD models and computational methods to gain insights from data obtained from the Platform to predict similar drug responses in humans. Modeling can also be used to help identify and solve potential problems that may be encountered as one integrates multiple Organ Chips; it also can help in optimizing system controls within the Platform.

An iterative process can be used to evaluate and refine endpoints as one progressively builds the complexity of the integrated human-on-a-Chip Microphysiological Platform. One can use a combination of on-Platform and off-Platform measurements and assays to obtain the crucial data required for these modeling efforts. For example, one can use existing computer modeling tools, such as CoBi from CFDRC, to extrapolate in vitro data (e.g. half-lives, clearance, tissue distribution, and metabolic and elimination pathways) obtained from the Platform to in vivo conditions. High fidelity models can be developed and used to optimize Interrogator instrument design as well as for model validation, and reduced (multi-compartmental) models can be used for development of PK, PD and Tox simulations.

CFDRC has already used its core CoBi tools for high fidelity and multi-compartmental PK modeling for in vivo (human, rat, mouse) and in vitro conditions in several projects with the Department of Defense and the pharmaceutical industry. The existing models include physiological-based 3D and reduced order computational models of several Organs including lung (16), liver (16) and heart (18), which can be adapted to model PK/PD in the Platform system described herein.

These models can be used to simulate integrated physiological performance of Organs as well as physiologically based PK (PBPK) and PD of the drugs shown in Table 2. The PK model can be used to calculate drug metabolism rates, rate of metabolite formation, and coupled with the physiology model to represent membrane and tissue physiology (e.g. heart rate, autoregulation, vasodilation, vascular permeability, tissue perfusion, etc.) and relevant biological processes (metabolic pathways, release and modulation of immune cytokines, oxidative stress, apoptosis, and physiological properties).

To develop a drug cardiotoxicity model, one can use data obtained from cardiophysiological measurements in the Heart Chip (bioenergetics, contractility, electrophysiology) in normal and stressed states in vitro, in the presence or absence of different drugs with or without connection to Lung and Liver Chips. The cardiotoxicity model can account for corresponding action mechanisms (e.g., inhibition of HERG K+ channels by terfenadine causing conduction defects), and link it to sudden cardiac death observed in humans. HERG K+ channel turnover rates can be modified as a function of local terfenadine concentrations to properly reflect its inhibitory activity on K+ channel function.

Models of physiology and PBPK for additional Organs can be developed and integrated into a predictive virtual multi-Organ physiological system. For example, addition of a Gut Chip can allow examination and modeling of the interplay between drug metabolizing enzyme activity and drug transporters in the Gut and Liver (key determinant of PK and toxicity in vivo), and addition of the Kidney Chip can permit validation of renal clearance for the PK/PD model. Effects of barrier function (e.g. gut, skin, BBB) also can be studied, and local drug concentrations produced by different delivery routes across these barriers (versus i.v. route) can be obtained from the developed PK models. Additionally, computer-based PBPK models, such as CoBi-based PBPK models, can be used to correlate and extrapolate in vitro PK/PD data to in vivo conditions in humans.

Without wishing to be bound by a theory, mathematical models of individual Organ Chips can account for device geometry, cell/tissue properties, fluid-solid biomechanics, perfusion, epi/endothelial transport, diffusion, drug-binding, and cellular biology. The PK models can require solution of additional convection/diffusion/reaction transport equations of free/bound drugs, adsorption on surfaces (e.g., air/mucus), transport across barriers, binding to ECM and cell membranes, and intracellular distribution/processing. CFDRC has a database of physicochemical properties (solubility, diffusion and partition coefficients, protein binding, etc.) for several drugs including those disclosed herein.

In some embodiments, two time scales can be simulated: the hydro-mechanics (sec/min) to model Organ performance and perfusion, and the biological (hrs/days) to analyze cell/tissue responses during cultivation, stressing and exposure. Each Organ and the connecting infrastructure (tubes, valves, pumps, sensors, actuators) can be represented with reduced order models and used for system level simulations, model based controls, in vitro PBPK simulations, and data extrapolation to a human PBPK model.

While no comparable Platform exists in the current state-of-the-art, systems and components described herein provide a number of advantages. For example, Lung Chips undergo breathing motions, which have been shown to be critical for observing human-relevant pathophysiological responses and drug toxicities. Heart Chips can beat and can measure changes in diastolic tension, which is very hard to do in isolated muscle. Liver Chips can mimic oxygen tension-dependent zonation of the liver that is critical for human hepatoxicity. Kidney Chips exhibit low baseline expression of KIM-1, which is an FDA-approved marker of renal toxicity that is commonly expressed constitutively at high levels, and hence these Chips can be used for in vitro toxicity studies. Gut Chips can support growth of living intestinal bacteria that are critical for absorption and metabolism of some drugs, without compromising barrier function. Most commercial clinical analyzer instruments used for measuring relevant cellular products, such as glucose, lactate, pH, and $O_2$, have been optimized for measuring electrolytes in mL volumes of blood plasma and have detectors with large surface areas and hence large dead space. Simple glucose sensors abound, but are not readily interfaced and do not have long-term stability or calibration. The Molecular Devices Cytosensor Microphysiometer, manufactured for 15 years beginning in the early 1990's, could measure only pH, albeit with milli-pH sensitivity, 15 sec time response and several μL volumes enclosing ~$10^5$ cells. Measuring only pH is insufficient to detect many metabolic changes in cells, since multiple mechanisms lead to acidification.

Inventors have added glucose, lactate and $O_2$ sensors to the Cytosensor using expensive commercial potentiostats, and then replaced these potentiostats with an economical, custom unit. Cytosensors can be replaced with custom microfluidics and screen-printed electrodes. This miniaturized and more sensitive instrument is the MicroClinical Analyzer that can be incorporated into the Platform described herein.

The invention can be described by one or more of the numbered paragraphs:
1. An Organ Cartridge, wherein the Organ Cartridge comprises a base substrate which includes
   a. a holder and microfluidic connections for at least one Organ-Chip or one port adapted for the Organ-Chip disposed thereon; and
   b. at least one fluidic circuit having an inlet and an outlet, in connection with the at least one Organ Chip or the corresponding port.

2. The Organ Cartridge of paragraph 1, wherein the Organ Cartridge fluidically connects to, the Organ-Chip, a second Organ Cartridge, an Organ-Farm, or an Organ-Interrogator.
3. The Organ Cartridge of paragraph 2, wherein the Organ Cartridge connects directly to the second Organ Cartridge, the Organ-Farm, or the Organ-Interrogator.
4. The Organ Cartridge of paragraph 2, wherein the Organ Cartridge connects to the second Organ Cartridge, the Organ-Farm, or the Organ-Interrogator via a Cartridge-dock.
5. The Organ Cartridge of any of paragraphs 1-4, wherein the Organ Cartridge further comprises at least one sensor adapted for monitoring or recording a parameter relating to temperature, metabolic activity, health or culture conditions of cells on the at least one Organ-Chip.
6. The Organ Cartridge of paragraph 5, wherein the at least one sensor comprises at least one electrochemical sensor.
7. The Organ Cartridge of paragraph 5 or 6, wherein the Organ Cartridge comprises at least one valve adapted to selectively connect the at least one sensor with at least one fluidic circuit.
8. The Organ Cartridge of any of paragraphs 5-7, wherein the Organ Cartridge comprises one of more reservoirs containing sensor washing or calibration fluids.
9. The Organ Cartridge of any of paragraphs 1-8, wherein the at least one Organ-Chip disposed on the Organ Cartridge can be optically interrogated by external instrumentation, stand-alone microscopes, in-line imaging, or other imaging devices.
10. The Organ Cartridge of any of paragraphs 1-9, wherein the Organ Cartridge comprises a microscope integrated into the Organ Cartridge.
11. The Organ Cartridge of any of paragraphs 1-10, wherein the Organ Cartridge comprises a means of thermal regulation of the at least one Organ-Chip disposed thereon.
12. The Organ Cartridge of any of paragraphs 1-11, wherein the Organ-Cartridge comprises at least one microprocessor.
13. The Organ Cartridge of any of paragraphs 1-12, wherein the Organ Cartridge comprises at least one microprocessor adapted for controlling flow of a fluid through the at least one Organ-Chip.
14. The Organ Cartridge of any of paragraphs 1-13, wherein the Organ Cartridge comprises at least one microprocessor adapted for controlling the amount of a drug, chemical, or biological challenge agent delivered to the at least one Organ Chip.
15. The Organ Cartridge of any of paragraphs 12-14, wherein the microprocessor is adapted for wireless communication with an external controller.
16. The Organ Cartridge of any of paragraphs 1-15, wherein the Organ Cartridge is adapted for interfacing with an external diagnostic, measurement, or control instrument.
17. The Organ Cartridge of any of paragraphs 1-16, wherein the Organ Cartridge comprises at least one bubble trap.
18. The Organ Cartridge of any of paragraphs 1-17, wherein the Organ Cartridge is a self-contained system comprising one or more on-board reservoirs containing nutrients; and at least one on-board waste reservoir adapted to contain effluent from the at least one Organ-Chip.
19. The Organ Cartridge of any of paragraphs 1-18, wherein the Organ Cartridge comprises one or more fluidic conduits adapted to support the operation of one or more pumps.
20. The Organ Cartridge of any of paragraphs 1-19, wherein the Organ Cartridge comprises one or more pumps connected to one or more of the at least one fluidic circuits.
21. The Organ Cartridge of any of paragraphs 1-20, wherein the Organ Cartridge comprises one or more fluidic conduits adapted to support the operation of a valve.
22. The Organ Cartridge of any of paragraphs 1-21, wherein the Organ Cartridge comprises one or more valves in connection with one or more of the at least one fluidic circuits.
23. The Organ Cartridge of any of paragraphs 1-22, wherein the Organ Cartridge is adapted for selecting the fluid in one of more of the at least one fluidic circuits.
24. The Organ Cartridge of any of paragraphs 1-23, wherein the Organ Cartridge is adapted for recirculating fluid in one or more of the at least one fluidic circuits.
25. The Organ Cartridge of any of paragraphs 1-24, wherein the Organ Cartridge comprises a plurality of Organ Chips disposed thereon.
26. The Organ Cartridge of any of paragraphs 1-25, wherein the Organ Chip is integrated into the Organ Cartridge.
27. The Organ Cartridge of any of paragraphs 1-26, wherein at least one fluidic circuit comprises a manifold or microfluidic channel.
28. The Organ Cartridge of any of paragraphs 1-27, wherein at least one fluidic circuit connects to the Organ-Chip using at least one face-sealing raised surface or an O-ring.
29. The Organ Cartridge of any of paragraphs 1-28, wherein the Organ Cartridge comprises at least one septum for providing fluidic connections.
30. The Organ Cartridge of any of paragraphs 1-29, wherein the Organ Cartridge comprises: a holder and microfluidic connections for at least one Organ-Chip or one port adapted for an Organ-Chip disposed thereon; at least one fluidic circuit having an inlet and an outlet, in connection with the at least one Organ Chip or the corresponding port, wherein the inlet and the outlet independently comprise a Luer Lock and wherein the at least one fluidic circuit connects to the Organ-Chip using at least one face-sealing raised surface or an O-ring; and at least one bubble trap in connection with the at least one fluidic circuit and the Organ Chip disposed on the Organ Cartridge.
31. The Organ Cartridge of any of paragraphs 1-30, wherein the Organ Cartridge comprises: a holder and microfluidic connections for at least one Organ-Chip or one port adapted for an Organ-Chip disposed thereon; at least one fluidic circuit having an inlet and an outlet, in connection with the at least one Organ Chip or the corresponding port; at least one pump in connection with the at least one fluidic circuit; at least one valve in connection with the at least one fluidic circuit; at least Micro-Clinical Analyzer in connection with the at least one fluidic circuit; and at least one Perfusion Controller in connection with the at least one fluidic circuit.
32. A Cartridge-dock, wherein the Cartridge-dock comprises a base substrate which includes:

a. a holder and connections for at least one Organ Cartridge of any of paragraphs 1-31; and
b. at least one fluidic circuit having an inlet and an outlet, in connection with one or more of the at least one Organ Cartridge.

33. The Cartridge-dock of paragraph 32, wherein the Cartridge-dock fluidically connects two or more Organ Cartridges.
34. The Cartridge-dock of any of paragraphs 32-33, wherein the Cartridge-dock comprises a sensor or monitor adapted for monitoring of fluid flow or pressure in the at least one fluidic circuit.
35. The Cartridge-dock of any of paragraphs 32-34, wherein the Cartridge-dock comprises a sensor or monitor adapted for monitoring the chemical or physical properties or composition of fluid in the at least one fluidic circuit.
36. The Cartridge-dock of any of paragraphs 32-35, wherein the Cartridge-dock comprises an apparatus or module for delivering a biological challenge to at least one of the Organ-Chips.
37. The Cartridge-dock of paragraph 36, wherein the biological challenge is an active agent (e.g., a drug), stimulator, inhibitor, modulator, trophic factor, toxin or a chemical.
38. The Cartridge-dock of any of paragraphs 32-37, wherein the Cartridge-dock comprises an apparatus or module for removing waste from at least one of the Organ-Chips.
39. The Cartridge-dock of any of paragraphs 32-38, wherein the Cartridge-dock comprises an apparatus or module for recirculating a fluid within the Cartridge-dock, within one or more Organ Cartridges disposed on the Cartridge-dock, or within one or more Organ-Chips disposed on the Cartridge-dock.
40. The Cartridge-dock of any of paragraphs 32-39, wherein two of more of the Organ-Chips are fluidically connected in parallel, series, or any combinations thereof.
41. The Cartridge-dock of paragraphs 39 or 40, wherein the Cartridge-dock comprises a module or apparatus for reconfiguring the fluid recirculation or fluidic connection.
42. The Cartridge-dock of any of paragraphs 39-41, wherein the Cartridge-dock comprises at least one afferent fluidic bus and at least one efferent fluidic bus.
43. The Cartridge-dock of any of paragraphs 32-42, wherein the Cartridge-dock comprises an apparatus or module for sampling or extracting a fluid from at least one of the Organ-Chip.
44. The Cartridge-dock of any of paragraphs 32-43, wherein the Cartridge-dock comprises a sensor or monitor adapted for time-course monitoring of effluent characteristics of at least one Organ-Chip.
45. The Cartridge-dock of any of paragraphs 32-44, wherein the Cartridge-dock comprises a microscope adapted to image at least one Organ-Chip.
46. The Cartridge-dock of any of paragraphs 32-45, wherein the Cartridge-dock comprises an on-board monitoring system.
47. The Cartridge-dock of paragraph 46, wherein the on-board monitoring system comprises an alarm to notify a user.
48. The Cartridge-dock of any of paragraphs 16-26, wherein the Cartridge-dock comprises a sensor adapted for feedback mechanism to maintain inter-Organ homeostatic systemic behavior.
49. An instrument for long-term culturing of a plurality of Organ-Chips; the instrument or device comprising: (a) a plurality of interfaces for attaching and detaching one or more Organ Chips to the instrument; (b) a means of perfusing the one or more Organ-Chips attached to the instrument with appropriate biological media using prescribed conditions; and (c) a means of controlling the temperature of (and optionally gas mixture provided to) said Organ-Chips.
50. The instrument of paragraph 49, wherein the instrument further comprises a sensor or monitor adapted for monitoring state and/or progress of cells on said one or more Organ-Chips.
51. The instrument of paragraph 49 or 50, wherein the instrument comprises one or more microscopes or other imaging modality adapted to image at least one Organ-Chip.
52. The instrument of paragraph 51, wherein at least one of the one or more microscopes or other imaging modality is a microscope blade
53. The instrument of paragraph 51, wherein at least one of the one or more microscopes or other imaging modality is an in-line microscope
54. The instrument of any of paragraphs 51-53, wherein the one or more microscopes or other imaging modality can be added or removed independently.
55. The instrument of paragraph 49-54, wherein the instrument further comprises an apparatus or module for actuating a mechanical or electrical function in at least one Organ-Chip.
56. The instrument of any of paragraphs 49-55, wherein the instrument comprises at least one first reservoir for holding media and at least one second reservoir for holding waste.
57. The instrument of any of paragraphs 49-56, wherein the instrument further comprises a sensor or monitor adapted for monitoring of fluid flow or pressure in the one or more Organ-Chips.
58. The instrument of any of paragraphs 49-57, wherein the instrument comprises a sensor or monitor adapted for monitoring the chemical or physical properties or composition of fluid in the at least one fluidic circuit.
59. The instrument of any of paragraphs 49-58, wherein the instrument comprises an apparatus or module for delivering a biological challenge to at least one of the Organ-Chips.
60. The instrument of paragraph 59, wherein the biological challenge is an active agent (e.g., a drug), stimulator, inhibitor, modulator, trophic factor, toxin or a chemical.
61. The instrument of any of paragraphs 49-60, wherein the instrument comprises an apparatus or module for removing waste from at least one of the Organ-Chips.
62. The instrument of any of paragraphs 49-61, wherein the instrument comprises an apparatus or module for recirculating a fluid within a Cartridge-dock, within one or more Organ Cartridges disposed on a Cartridge-dock, or within one or more Organ-Chips disposed in the instrument.
63. The instrument of any of paragraphs 49-62, wherein two of more of the Organ-Chips are fluidically connected in parallel, series, or any combinations thereof.
64. The instrument of paragraphs 62 or 63, wherein the Cartridge-dock comprises an apparatus or module for reconfiguring the fluid recirculation or fluidic connection.

65. The instrument of any of paragraphs 62-64, wherein the Cartridge-dock comprises at least one afferent fluidic bus and at least one efferent fluidic bus.
66. The instrument of any of paragraphs 49-65, wherein the instrument comprises an apparatus or module for sampling or extracting a fluid from at least one Organ-Chip.
67. The instrument of any of paragraphs 49-66, wherein the instrument comprises a sensor or monitor adapted for time-course monitoring of effluent characteristics of at least one Organ-Chip.
68. An in vitro microphysiological system comprising two or more Organ-Chips, wherein the Organ-Chips are fluidically connected in parallel, series, or any combinations thereof.
69. The microphysiological system of paragraph 68, wherein the microphysiological system comprises at least ten Organ-Chips.
70. The microphysiological system of paragraph 68 or 69, wherein each Organ Chip mimics a different Organ or functional unit of an Organ.
71. The microphysiological system of any of paragraphs 68-70, wherein the microphysiological system comprises two or more Organ Chips, wherein at least one Organ Chip mimics a first aspect of an organ and at least one Organ Chip mimics a second aspect of the same organ.
72. The microphysiological system of any of paragraphs 68-71, wherein the microphysiological system comprises two or more Organ Chips, wherein at least one Organ Chip mimics a small airway of the lung and at least one Organ Chip mimics an alveolar-capillary interface of a lung.
73. The microphysiological system of any of paragraphs 68-72, wherein the Organ-Chips are disposed on an Organ Cartridge of any of paragraphs 1-31.
74. The microphysiological system of any of paragraphs 68-73, wherein the Organ-Chips are disposed on a Cartridge-dock of any of paragraphs 32-48.
75. The microphysiological system of any of paragraphs 68-74, wherein the Organ-Chips are in the instrument of any of paragraphs 49-67.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

REFERENCES

1. Report on "Animal Models for Assessing Countermeasures to Bioterrorism Agents"-*National Research Council* [US] 2011.
2. Huh D, Matthews B D, Mammoto A, Montoya-Zavala M, Hsin H Y, and Ingber D E. Reconstituting Organ-level lung functions on a Chip. *Science* 2010, 328: 1662.
3. Feinberg A W, Feigel A, Shevkoplyas S S, Sheehy S, Whitesides G M, Parker K K. Muscular thin films for building actuators and powering devices. *Science* 2007, 317:1366.
4. Grosberg A, Alford P W, McCain M L, Parker K K. Ensembles of engineered cardiac tissues for physiological and pharmacological study: Heart on a Chip. *Lab on a Chip* 2011, 11:4165.
5. Edward L, LeCluyse, Alexandre E, Hamilton G A, Viollon-Abadie C, Coon D J, Jolley S, and Richert L. Isolation and Culture of Primary Human Hepatocytes, In: Helgarson C, ed., *Basic Cell Culture Protocols: Methods in Molecular Biology—Third Edition*, Humana Press, 2004.
6. Hamilton G, Laethem R M, Jolley S L, Gilbert D, Coon D J, Webster L, LeCluyse E L. The effects of culture conditions on the expression of drug-metabolizing enzymes in primary human hepatocytes. *Drug Metabolism Reviews* 2002 1: 103.
7. Mooney, D, Hansen, L, Farmer, S, Vacanti, J, Langer R, Ingber, D E. Switching from differentiation to growth in hepatocytes: control by extracellular matrix. *J. Cell Physiol.* 1992; 151:497.
8. Singhvi R, Kumar A, Lopez G, Stephanopoulos G N, Wang D I C, Whitesides G M, Ingber D E. Engineering cell shape and function. *Science* 1994, 264:696.
9. Carlson M W, Alt-Holland A, Egles C, and Garlick J A. Three-Dimensional Tissue Models of Normal and Diseased Skin. *Current Protocols in CellBiology* 19.9.1-19.9.17, December 2008 Published online December 2008 in Wiley Interscience (www.interscience.wiley.com).

10. Lejeune H, Sanchez P, Saez J M. Enhancement of long-term testosterone secretion and steroidogenic enzyme expression in human Leydig cells by co-culture with human Sertoli cell-enriched preparations. *Int J Androl.* 1998 21:129.
11. Darby S, Moore M, Wikswo J P, Reiserer R, Friedlander T, Schaffer D K, Seale K T. A Metering Rotary Nanopump for Microfluidic Systems, *Lab on a Chip* 2010, 10: 3218.
12. Velkovsky M, Snider R, Cliffel D E, Wikswo J P. Modeling the Measurements of Cellular Fluxes in Microbioreactor Devices Using Thin Enzyme Electrodes, *Journal of Mathematical Chemistry* 2011, 49: 251.
13. Eklund S E, Taylor D, Kozlov E, Prokop A, Cliffel D E. A Microphysiometer for Simultaneous Measurement of Changes in Extracellular Glucose, Lactate, Oxygen, and Acidification Rate, *Anal. Chem.* 2004, 76: 519.
14. Obach R S and Reed-Hagen A E. Measurement of michaelis constants for cytochrome P450-mediated biotransformation reactions using a substrate depletion approach. *Drug Metab Dispos.* 2002, 30:83.
15. Riley R J, McGinnity D F, Austin R P. A unified model for predicting human hepatic, metabolic clearance from in vitro intrinsic clearance data in hepatocytes and microsomes. *Drug Metab Dispos.* 2005 33:1304. (Epub 2005 Jun. 2.)
16. Ding H, Jiang Y, Furmanczyk M, Przekwas A, Reinhardt J M, Simulation of human lung respiration process Using 3-D CFD with Macro Air Sac System Model, Soc. for Modeling and Simulation Int. Conf, New Orleans, Jan. 23-27, 2005.
17. Rani H P, Sheu T W, Chang T M, Liang P C, Numerical investigation of non-Newtonian microcirculatory blood flow in hepatic lobule, *J Biomechanics* 2006, 39: 551.
18. Sukumar R, Athavale M M, Makhijani V B, Przekwas A, Application of computational fluid dynamics techniques to blood pumps, *Artificial Organs* 1996, 20: 529.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

What is claimed is:

1. A device, comprising Sertoli and Leydig cells on a first side of a membrane, and endothelial cells on a second side of said membrane.
2. The device of claim 1, wherein said Sertoli and Leydig cells are human cells.
3. The device of claim 1, wherein said membrane is an ECM-coated membrane.
4. The device of claim 3, wherein said ECM-coated membrane is coated with laminin.
5. The device of claim 3, wherein said ECM-coated membrane is coated with type IV collagen.
6. The device of claim 1, wherein said endothelial cells are human endothelial cells.
7. A method comprising:
    a) providing Sertoli and Leydig cells on a first side of a membrane in a first channel, and endothelial cells on a second side of said membrane in a second channel; and
    b) culturing said cells.
8. The method of claim 7, wherein said Sertoli and Leydig cells are human cells.
9. The method of claim 7, wherein said membrane is an ECM-coated membrane.
10. The method of claim 9, wherein said ECM-coated membrane is coated with laminin.
11. The method of claim 9, wherein said ECM-coated membrane is coated with type IV collagen.
12. The method of claim 1, wherein said endothelial cells are human endothelial cells.

* * * * *